(12) United States Patent
Tang et al.

(10) Patent No.: US 10,871,491 B2
(45) Date of Patent: *Dec. 22, 2020

(54) USE OF CIRCULATING CELL BIOMARKERS IN THE BLOOD FOR DETECTION AND DIAGNOSIS OF DISEASES AND METHODS OF ISOLATING THEM

(71) Applicant: Creatv MicroTech, Inc., Potomac, MD (US)

(72) Inventors: Cha-Mei Tang, Potomac, MD (US); Daniel Adams, Basking Ridge, NJ (US)

(73) Assignee: CREATV MICROTECH, INC., Potomac, MD (US)

( * ) Notice: Subject to any disclaimer, the term of this patent is extended or adjusted under 35 U.S.C. 154(b) by 195 days.

This patent is subject to a terminal disclaimer.

(21) Appl. No.: 15/506,439

(22) PCT Filed: Aug. 25, 2015

(86) PCT No.: PCT/US2015/046782
§ 371 (c)(1),
(2) Date: Feb. 24, 2017

(87) PCT Pub. No.: WO2016/033103
PCT Pub. Date: Mar. 3, 2016

(65) Prior Publication Data
US 2018/0238893 A1 Aug. 23, 2018

Related U.S. Application Data

(60) Provisional application No. 62/166,492, filed on May 26, 2015, provisional application No. 62/138,744, filed on Mar. 26, 2015, provisional application No. 62/131,051, filed on Mar. 10, 2015, provisional application No. 62/041,540, filed on Aug. 25, 2014.

(51) Int. Cl.
| | | |
|---|---|---|
| *G01N 33/574* | (2006.01) | |
| *C12Q 1/6886* | (2018.01) | |
| *C12N 5/09* | (2010.01) | |
| *G01N 33/569* | (2006.01) | |

(52) U.S. Cl.
CPC ..... *G01N 33/57492* (2013.01); *C12N 5/0694* (2013.01); *C12Q 1/6886* (2013.01); *G01N 33/56983* (2013.01); *C12Q 2600/112* (2013.01); *C12Q 2600/118* (2013.01); *C12Q 2600/158* (2013.01); *G01N 2800/085* (2013.01)

(58) Field of Classification Search
None
See application file for complete search history.

(56) References Cited

U.S. PATENT DOCUMENTS

| | | |
|---|---|---|
| 7,993,826 B2 | 8/2011 | Giesing et al. |
| 8,551,425 B2 | 10/2013 | Goldkorn et al. |
| 2006/0178833 A1 | 8/2006 | Bauer et al. |
| 2014/0315295 A1 | 10/2014 | Makarova et al. |

FOREIGN PATENT DOCUMENTS

| | | |
|---|---|---|
| WO | 2007/089911 | 8/2007 |
| WO | 2009/092068 | 7/2009 |
| WO | 2010/028160 | 3/2010 |
| WO | 2010/047682 | 4/2010 |
| WO | 2010/111388 | 9/2010 |
| WO | 2011/002649 | 1/2011 |
| WO | 2011/139445 | 11/2011 |
| WO | 2013/181532 | 12/2013 |

OTHER PUBLICATIONS

Leers et al., "A Three-Color/Five-Parameter Flow Cytometric Study on Peripheral Blood Samples", Am J Clin Pathol, 129: 649-656 (2008).
Caillou et al., "Tumor-Associated Macrophages (TAMs) Form an Interconnected Cellular Supportive Network in Anaplastic Thyroid Carcinoma", PLoS ONE, 6(7): e22567 (2011).
Wang et al., "Identification and Characterization of Circulating Prostate Carcinoma Cells", Cancer, 88(12): 2787-2795 (2000).
Zhang et al., "Alternatively Activated RAW264.7 Macrophages Enhance Tumor Lymphangiogenesis in Mouse Lung Adenocarcinoma", Journal of Cellular Biochemistry, 107: 134-143 (2009).
Duluc et al., "Tumor-associated leukemia inhibitory factor and IL-6 skew monocyte differentiation into tumor-associated macrophage-like cells", Blood, 110(13): 4319-4330 (2007).
Morgan et al., "Molecular Profiling of Giant Cell Tumor of Bone and Osteoclastic Localization of Ligand for Receptor Activator of Nuclear Factor KB", American Journal of Pathology, 167(1): 117-128 (2005).
Extended European Search Report dated Mar. 8, 2016, issued in corresponding European Application No. 13797578.5.
Extended European Search Report issued Sep. 17, 2018 in European Application No. 18179948.7.
International Search Report and Written Opinion for PCT/US2013/043610, dated Nov. 1, 2013.
Faber et al. Activated macrophages containing tumor marker in colon carcinoma: immunohistochemical proof of a concept. Tumor Biol. ePub Dec. 2, 2011, vol. 33, No. 2, pp. 435-441.
Krombach et al. Cell Size of Alveolar Macrophages: An Interspecies Comparison. Environmental Health Perspectives Sep. 1997, vol. 105, Supplement 5, pp. 1261-1263.
Schmid et al. Myeloid cell trafficking and tumor angiogenesis. Cancer Lett 2007. 250(1):1-8.
Amani et al., Flow Cytometric Analysis of Tumor Associated Macrophages in Invasive Ductal Carcinoma of Breast 2005, 2(2):117-122.

(Continued)

Primary Examiner — Andrea S Grossman
(74) Attorney, Agent, or Firm — Wenderoth, Lind & Ponack, L.L.P.

(57) ABSTRACT

A new sensitive cell biomarker of solid tumors and viral infection is identified in blood. This biomarker can be used to determine presence of carcinomas, sarcomas, and viruses, rapid determination of treatment response, early detection of cancer, early detection of cancer recurrence, and may be used to determine therapy.

15 Claims, 54 Drawing Sheets

(56) References Cited

OTHER PUBLICATIONS

Zhang et al., "Early Lung Cancer Diagnosis by Biosensors", Int. J. Mol. Sci., 14: 15479-15509 (2013).
International Search Report and Written Opinion of the International Searching Authority, dated Jan. 19, 2016 in corresponding International application No. PCT/US15/46782.
Extended European Search Report dated Jan. 30, 2018 in European Application No. 15836011.5.
Adams et al., "Circulating giant macrophages as a potential biomarker of solid tumors", Proceedings National Academy of Sciences PNAS, 111; 9, 3514-3519 (2014).

USE OF CIRCULATING CELL BIOMARKERS IN THE BLOOD FOR DETECTION AND DIAGNOSIS OF DISEASES AND METHODS OF ISOLATING THEM

BACKGROUND

Field of the Invention

The present invention generally relates to the discovery and characterization of biomarkers in blood and other body fluids that can be used to screen a subject for the presence of solid tumors, aid in selecting a course of cancer therapy, monitor the efficacy of cancer treatments, and detect and monitor viral infections in a subject, cancer screening, early detection of cancer recurrence, among other important goals. The biomarkers of the invention may be used alone or in combination with circulating tumor cells, free plasma and serum DNA cancer markers, cancer-associated protein markers and other biomarkers.

Related Art

When tumor cells break away from primary solid tumors, they penetrate into the blood or lymphatic circulation, and ultimately leave the blood stream and enter other organ or tissue to form metastasis. 90% of cancer-related deaths are caused by the metastatic process. The most common metastatic sites are the lung, liver, bone and brain. Tumor cells found in the circulation are called circulating tumor cells (CTCs). Many research publications and clinical trials show that CTCs have clinical utility in (i) providing prognostic survival and cancer recurrence information through the enumeration of CTCs in the blood stream, and (ii) providing treatment information through examination of protein expression levels, and the occurrence of gene mutations and translocations in the CTCs. However, CTCs are not consistently associated with the development and/or presence of cancer in a subject, even in stage IV cancer patients.

There are medical conditions in addition to cancer that can be diagnosed through the detection of certain cell types in bodily fluids. In particular, cells indicative or characteristic of certain medical conditions may be larger and/or less flexible than other cells found in selected bodily fluids. Accordingly, by collecting such larger and/or less flexible cells from a sample of a bodily fluid, it may be possible to diagnose a medical condition based on the cells collected.

The identification and characterization of biomarkers in blood and other body fluids that can be used to screen a subject for medical conditions would provide additional tools to a clinician. The present invention is directed to this and other important goals.

SUMMARY

The present invention is directed to and discloses a type of cell with unique characteristics that is found in the blood of cancer patients having solid tumors, including carcinoma, sarcoma, neuroblastoma and melanoma. The cell, termed "circulating Cancer Associated Macrophage-Like cell" (CAML), is described herein and shown to be associated with the presence of solid tumors in a patient. Five morphologies associated with CAMLs have been characterized and described (Adams, D., et al., Circulating giant macrophages as a potential biomarker of solid tumors. *PNAS* 2014, 111(9):3514-3519 and WO 2013/181532). CAMLs are shown through the data presented herein to have clinical utility in that they can be used as a biomarker for a variety of medical applications. CAMLs have been found consistently in the peripheral blood of subjects having stage I to stage IV cancer of epithelial origin by microfiltration using precision microfilters. Additional CAML morphologies, found in blood of cancer patients, are presented herein.

Medical applications associated with CAMLs include, but are not limited to, use of the cell as a biomarker to provide a diagnosis of cancer, in particular, in the early detection of cancer, in the early detection of cancer relapse or recurrence, and in the determination of cancer mutation. CAMLs can also be used as a biomarker in determining appropriate courses of therapy; in particular, the cells can be used in a rapid determination of effectiveness of chemotherapy and radiation therapy treatment response.

CAMLS may be used independently as a cancer marker, or in combination with CTCs, cell-free DNA, proteins and other biomarkers to provide a more complete understanding of the patient's disease.

More specifically, and in a first embodiment, the present invention is directed to methods of screening a subject for cancer, comprising detecting CAMLs in a biological sample from a subject. In particular aspects, when CAMLs are detected in the biological sample, the subject is identified as potentially having a solid tumor, such as carcinoma, sarcoma, neuroblastoma or melanoma, among others. In other aspects, when CAMLs are detected in the biological sample, the subject is identified as having a solid tumor, such as carcinoma, sarcoma, neuroblastoma or melanoma, among others. The identification of the specific type of cancer can be performed by standard methods, such as staining for cancer markers. One of the useful attributes of CAMLs is that they can undergo quenching and re-staining, and therefore a large number of cancer cell markers can be assayed using the same sample of cells. The identification of the specific type of cancer can therefore also be performed by staining for cancer markers and then re-staining the same cells for additional markers. In certain aspects, the methods encompassed by this embodiment also include detecting circulating tumor cells (CTCs) and/or white blood cells (WBCs) bound to CTCs in the biological sample. In particular aspects of this embodiment, the subject is a subject suspected of having cancer. In particular aspects of this embodiment, a treatment decision is made based on the outcome of the method. In particular aspects of this embodiment, the method further comprises administering an anti-cancer therapeutic to the subject when the subject is identified as having a solid tumor.

In a second embodiment, the invention is directed to methods for diagnosing cancer in a subject, comprising detecting CAMLs in a biological sample from a subject, wherein when CAMLs are detected in the biological sample, the subject is diagnosed with cancer. The identification of the specific type of cancer can be performed by standard methods, such as staining for cancer markers. The identification of the specific type of cancer can also be performed by staining for cancer markers and then re-staining the same cells for additional markers. In certain aspects, the methods encompassed by this embodiment also include detecting CTCs and/or WBCs bound to CTCs in the biological sample, wherein when one or more of CAMLs, CTCs and WBCs bound to CTCs are detected in the biological sample, the subject is diagnosed with cancer. In particular aspects of this embodiment, a treatment decision is made based on the outcome of the method. In particular aspects of this embodiment, the method further comprises administering an anti-cancer therapeutic to the subject when the subject is diagnosed with cancer.

In a third embodiment, the invention is directed to methods for detecting recurrence of cancer in a subject, comprising detecting CAMLs in a biological sample from a subject previously treated for cancer, wherein when CAMLs are detected in the biological sample, recurrence of cancer is detected. The identification of the specific type of cancer can be performed by standard methods, such as staining for cancer markers. The identification of the specific type of cancer can also be performed by staining for cancer markers and then re-staining the same cells for additional markers. In certain aspects, the methods encompassed by this embodiment also include detecting CTCs and/or WBCs bound to CTCs in the biological sample, wherein when one or more of CAMLs, CTCs and WBCs bound to CTCs are detected in the biological sample, recurrence of cancer is detected. In particular aspects of this embodiment, a treatment decision is made based on the outcome of the method. In particular aspects of this embodiment, the method further comprises administering an anti-cancer therapeutic to the subject when recurrence of cancer is detected.

In a fourth embodiment, the invention is directed to methods for confirming a diagnosis of cancer in a subject, comprising detecting CAMLs in a biological sample from a subject diagnosed with cancer, wherein when CAMLs are detected in the biological sample, a diagnosis of cancer is confirmed in the subject. In certain aspects, the methods encompassed by this embodiment also include detecting CTCs and/or WBCs bound to CTCs in the biological sample, wherein when one or more of CAMLs, CTCs and WBCs bound to CTCs are detected in the biological sample, a diagnosis of cancer is confirmed in the subject. In particular aspects, the initial cancer diagnosis is via mammography, PSA test, presence of CA125, CT, MRI or PET imaging. In a particular aspect, the subject is suspected of having cancer. The identification of the specific type of cancer can be performed by standard methods, such as staining for cancer markers. The identification of the specific type of cancer can also be performed by staining for cancer markers and then re-staining the same cells for additional markers. In particular aspects of this embodiment, a treatment decision is made based on the outcome of the method. In particular aspects of this embodiment, the method further comprises administering an anti-cancer therapeutic to the subject when diagnosis of cancer is confirmed in the subject.

In the first through fourth embodiments of the invention, the detecting of WBCs bound to CTCs is determining the number of WBCs bound to CTCs. When CTCs penetrate into the circulation, immune cells (T-cells, a subtype of white blood cells) can recognize them by binding to the CTCs; the immune cells can also kill the CTCs. Filtration of the blood can capture white blood cells (WBCs) bound to the CTCs. The CTCs can become degraded. The presence and/or number of WBCs bound to CTCs in the biological sample is this an indication of presence of solid tumor and also the body's ability to eliminate the solid tumors. In certain aspects, the WBCs bound to CTCs in the biological sample are T cells.

In a fifth embodiment, the invention is directed to methods for determining cancer stage in a subject, comprising characterizing CAMLs in a biological sample from a subject having a cancer, wherein selected characteristics of the CAMLs indicate cancer stage in the subject. The identification of the specific type of cancer can be performed by standard methods, such as staining for cancer markers. The identification of the specific type of cancer can also be performed by staining for cancer markers and then re-staining the same cells for additional markers. In certain aspects, the methods encompassed by this embodiment also include characterizing CTCs in the biological sample, wherein selected characteristics of the CAMLs and CTCs indicate cancer stage in the subject. In certain aspects, the CAMLs and/or CTCs are collected from the biological sample prior to characterization. In particular aspects of this embodiment, a treatment decision is made based on the outcome of the method. In particular aspects of this embodiment, the method further comprises administering an anti-cancer therapeutic to the subject after determining cancer stage in the subject.

In a sixth embodiment, the invention is directed to methods for monitoring efficacy of a cancer treatment, comprising (a) assaying one or more selected characteristics of CAMLs in a biological sample from a subject undergoing cancer treatment, and (b) comparing assay values for the one or more selected characteristics determined in (a) to assay values for the same characteristics assayed in a similar biological sample from the same subject at one or more time points before, during or after completion of treatment, wherein a change in one or more assay values indicates efficacy of the cancer treatment in the subject. In certain aspects, the methods encompassed by this embodiment also include (a) assaying one or more selected characteristics of CTCs in the biological sample, and (b) comparing assay values for the one or more selected characteristics determined in (a) to assay values for the same characteristics assayed in a similar biological sample from the same subject at one or more time points before, during or after completion of treatment. In certain aspects, the CAMLs and/or CTCs are collected from the biological sample prior to characterization. In particular aspects of this embodiment, a treatment decision is made based on the outcome of the method.

In the fifth and sixth embodiments, the selected characteristics of the CAMLs in the sample are one or more characteristics selected from the group consisting of:
  (i) number of CAMLs;
  (ii) average size of the CAMLs (CAML cell sizes range from about 20 micron to about 300 microns in diameter);
  (iii) average size of the nuclei of the CAMLs (CAMLs have a large atypical nucleus having a size of about 14-64 µm in diameter);
  (iv) morphological shape of the CAMLs (CAML shapes include spindle, tadpole, round, oblong, two legs, more than two legs, thin legs, or amorphous);
  (v) CD14 positive phenotype;
  (vi) degree of CD45 expression;
  (vii) degree of EpCAM expression;
  (viii) degree of vimentin expression;
  (ix) degree of PD-L1 expression;
  (x) degree of monocytic CD11C marker expression;
  (xi) degree of endothelial CD146 marker expression;
  (xii) degree of endothelial CD202b marker expression;
  (xiii) degree of endothelial CD31 marker expression;
  (xiv) location of markers (the location markers appear in CAMLs, e.g., cytoplasm versus nucleus, can change at the different time points);
  (xv) presence of one or more markers associated with the cancer in the CAMLs, wherein the marker is diffused, or associated with vacuoles and/or ingested material (e.g., for epithelial cancer, the markers are cytokeratin 8, 18, and 19); and
  (xvi) intensity of marker staining.

In the fifth and sixth embodiments, the selected characteristics of the CTCs in the sample are one or more characteristics selected from the group consisting of:
(i) number of CTCs;
(ii) number of WBCs bound to the CTCs;
(iii) status of nucleus;
(iv) degree of cytokeratin 8 expression;
(v) degree of cytokeratin 18 expression;
(vi) degree of cytokeratin 19 expression;
(vii) degree of EpCAM expression;
(viii) degree of vimentin expression;
(ix) degree of PD-L1 expression;
(x) degree of uroplakin expression;
(xi) cytokeratin morphology;
(xii) location of markers (the location markers appear in CTCs, e.g., cytoplasm versus nucleus, can change at the different time points); and
(xiii) intensity of marker staining.

In the fifth and sixth embodiments, the numbers of CAMLs, CTCs and/or WBCs bound to CTCs are determined simultaneously using a microfilter. Suitable microfilters can have a variety of pore sizes and shapes. In one aspect, the microfilters have pores ranging in size from about 5 microns to about 10 microns in size, and may include round, racetrack shaped, oval, square and rectangular pore shapes. In a preferred aspect, the microfilter has precision pore geometry and uniform pore distribution.

The invention is also directed to methods for isolating CAMLs and/or CTCs from a biological sample and counting the isolated cells using a camera, such as a cell phone camera, or white light microscope, or a camera attached to a white light microscope. Thus, and in a seventh embodiment, the present invention is directed to methods for detecting CAMLs and/or CTCs in a biological sample, comprising obtaining a biological sample from a subject, and detecting CAMLs and/or CTCs in the sample, wherein the detecting is via a camera or a white light microscope, or a camera attached to a white light microscope. In certain aspects, the camera is a cell phone camera. In certain aspects, the white light microscope has a magnification power of 10× or less. In other aspects, the cells are collected from the biological sample via low cost filters and/or the biological sample is the obtained by manual draw from the subject or low cost pump. In further aspects, colorimetric staining is used to visualize the CAMLs and/or CTCs.

The invention is further directed to methods for using CAMLs and/or CTCs as companion diagnostics. Companion diagnostics is a useful tool in matching drugs for specific treatment by evaluating the staining of markers of the drug targets, evaluating gene amplifications or translocations by FISH, and using other molecular assays for specific gene mutations associated with the drugs, etc. The cells can serve in place of tissue biopsies in determining whether certain therapies might be effective in the treatment of a subject having a disease, such as cancer. For example, the cells can be used in screening of immunotherapeutics to determine whether a cancer expresses the protein recognized by a given immunotherapeutic (e.g., an antibody). The cells can also be assayed to determine whether the cells express certain polynucleotides or whether the selected mutations are found in cellular DNA. As noted herein, CAMLs and CTCs often express or possess the same cancer markers as the cancer from which they are derived. Thus, and in an eighth embodiment, the invention is directed to a companion diagnostic method for screening selected drug target markers in CAMLs and/or CTCs comprising collecting CAMLs and/or CTCs from a biological sample from a subject and determining whether the CAMLs and/or CTCs express or possess a selected drug target marker. In certain aspects, the drug target marker is cell surface marker, and the determining may be, for example, via staining for the marker. As an example, PD-L1 can be used as a cell surface marker for immunotherapeutics. In other aspects, the drug target marker is a polynucleotide. In further aspects, the drug target marker is a genetic mutation, amplification or translocation and the determining may be, for example, via FISH.

Traditional methods of detection of viruses in blood are based on the presence of antibodies or virally-infected cells. As CAMLs are a type of immune cell, they may also be used in a diagnostic for detection of a spectrum of viral infections, such as Human immunodeficiency virus (HIV), Hepatitis B virus (HBV), Epstein-Barr virus (EBV), and many more. Indeed, CAMLs have been found in blood of subjects with an active viral infection. CAMLs engulf viral debris, cells infected by virus, or cellular debris that contains virus. One can stain for the viral marker(s) directly in the CAMLs or perform molecular analysis of DNA or RNA in the CAML associated with the virus. Therefore, CAMLs can also be used as a biomarker to provide detection and diagnosis of active viral infections, and in determining appropriate courses of therapy.

Furthermore, some viral infections such as HIV and HBV can lead to cancer. CAMLs found in the blood of those patients can be caused either by viral infection or by cancer itself. Staining for the cancer marker or for viral marker(s) can be used to provide diagnostic information. This may also be a useful method for early detection of virus-caused cancer.

Thus, and in a ninth embodiment, the invention is directed to methods for diagnosing a viral infection in a subject, comprising collecting CAMLs from a biological sample obtained from a subject and screening the collected CAMLs for a virus. In certain aspects, the screening is via staining CAMLs for a viral marker. The same cells can also be re-staining for additional viral markers. In further aspects, the screening is via molecular analysis of DNA or RNA from the CAML. In particular aspects of this embodiment, a treatment decision is made based on the outcome of the method. In particular aspects of this embodiment, the method further comprises administering an anti-viral therapeutic to the subject when a viral infection is diagnosed.

In an additional embodiment, the present invention includes methods of molecular analysis of a CAML comprising obtaining a single CAML cell and conducting molecular analysis on the single cell. There is no limitation on the particular type of molecular analysis that may be conducted on the single cell and such means include, but are not limited to, nucleic acid sequencing, northern blot analysis and southern blot analysis.

In the relevant aspects and embodiments of the invention, the biological sample is one or more selected from the group consisting of peripheral blood, blood, lymph nodes, bone marrow, cerebral spinal fluid, tissue, and urine. The sample may be a fresh sample or a cryo-preserved sample that is thawed. In a preferred aspect, the biological sample is peripheral blood. In other aspects, the blood is antecubital-vein blood, inferior-vena-cava blood or jugular-vein blood.

In the relevant aspects and embodiments of the invention, the cancer is one or more of a solid tumor, Stage I cancer, Stage II cancer, Stage III cancer, Stage IV cancer, carcinoma, sarcoma, neuroblastoma, melanoma, epithelial cell cancer, breast cancer, prostate cancer, lung cancer, pancreatic cancer, colorectal cancer, and other solid tumor cancers.

In the relevant aspects and embodiments of the invention, the anti-cancer therapeutic may be one or more of chemotherapy, radiation therapy, immunotherapy, vaccine therapy, targeted therapy, and/or a combination of therapies.

In the relevant aspects and embodiments of the invention, CAMLs are detected and/or collected using one or more means selected from the group consisting of size exclusion methodology, immunocapture, red blood cell lysis, white blood cell depletion, FICOLL® (a hydrophilic polysaccharide), electrophoresis, dielectrophoresis, flow cytometry and microfluidic chip, or a combination thereof. In a particular aspect, the size exclusion methodology comprises use of a microfilter. Suitable microfilters can have a variety of pore sizes and shapes. When CAMLs alone are being detected and/or collected, the pore sizes can range from about 15 microns to about 20 microns. When both CAMLs and CTCs are being detected and/or collected, the pore sizes can range from about 5 microns to about 10 microns. The larger pore sizes will eliminate most of the WBC contamination on the filter. The pores may have a round, race-track shaped, oval, square and rectangular pore shape. In a preferred aspect, the microfilter has precision pore geometry and uniform pore distribution. In a particular aspect, CAMLs are detected and/or collected using a microfluidic chip based on physical size-based sorting, hydrodynamic size-based sorting, grouping, trapping, immunocapture, concentrating large cells, or eliminating small cells based on size. In a particular aspect, the CAMLs are detected and/or collected using a Cell-Sieve™ low-pressure microfiltration assay.

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein.

DETAILED DESCRIPTION

Figures 1A, 1B, 1C, 1D, 1E, 1F, 1G, 1H, 1I:
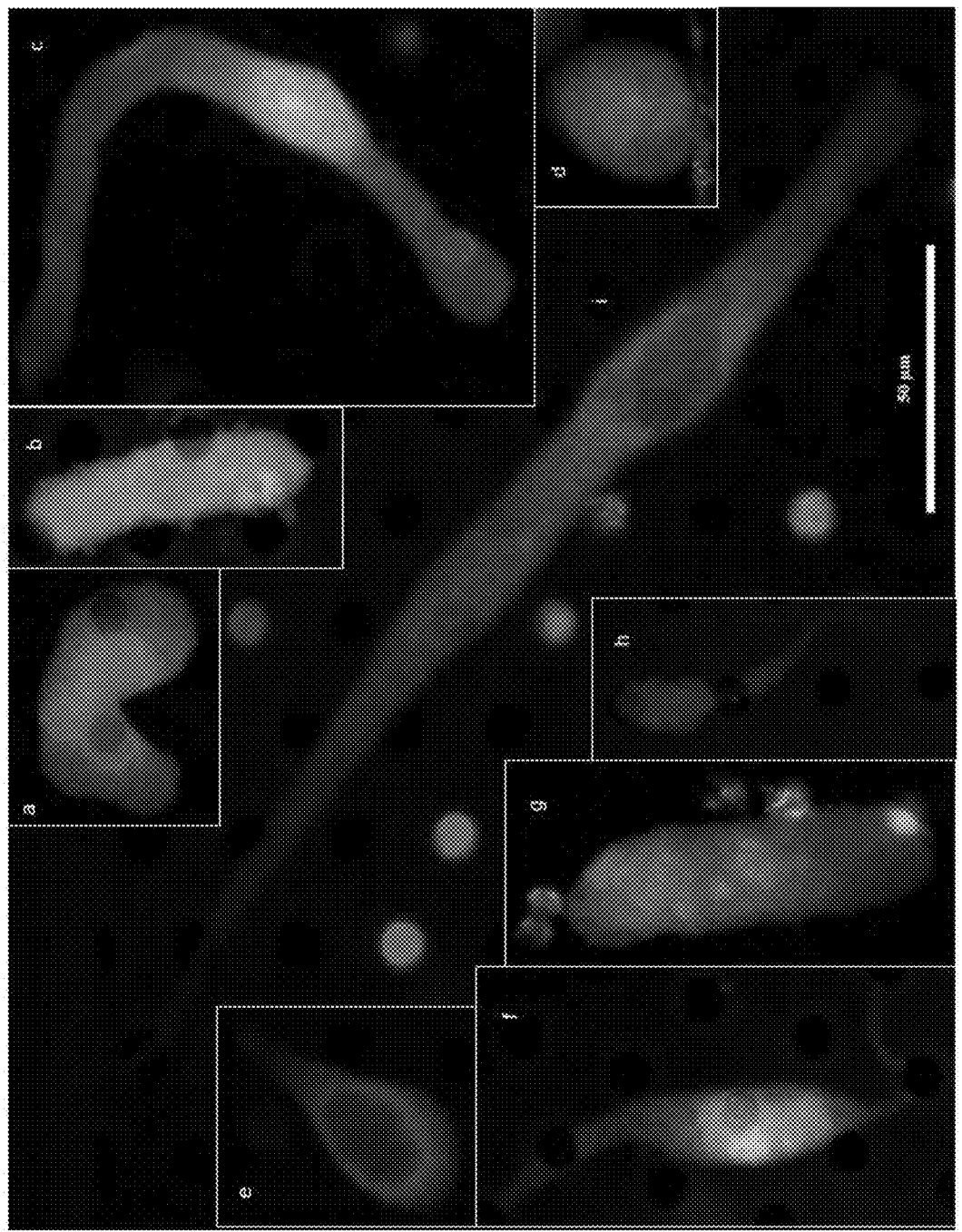
FIGS. 1A-1I show a gallery of circulating cancer associated macrophage-like cells found in the blood of cancer patients. The merged color images are generated by DAPI (blue), CK 8, 18 & 19 (green), EpCAM (red) and CD45 (violet).
Figures 2A, 2B:
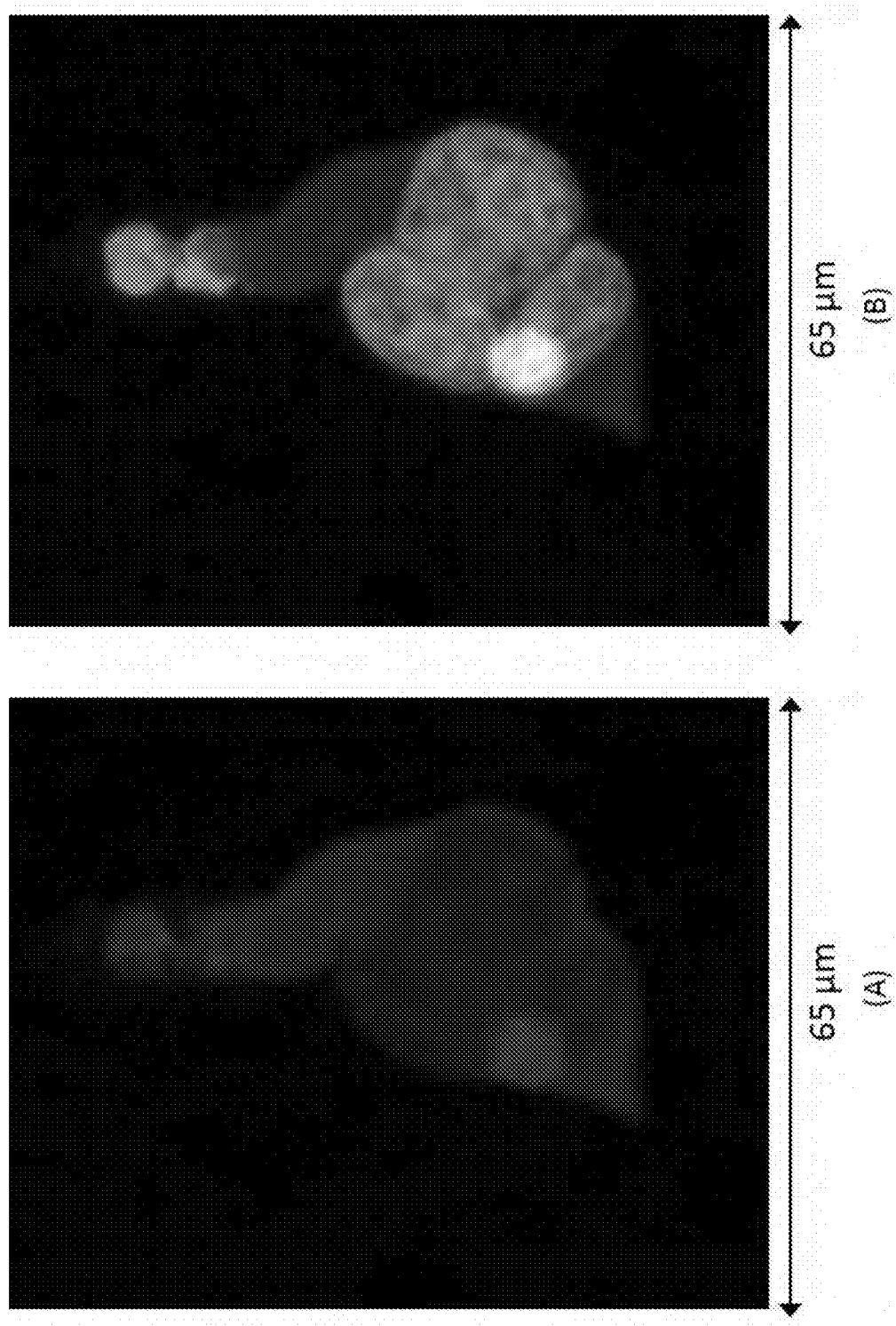
FIGS. 2A-2F show a CAML with engulfed DNA fragment in the tail.
Figure 2C:
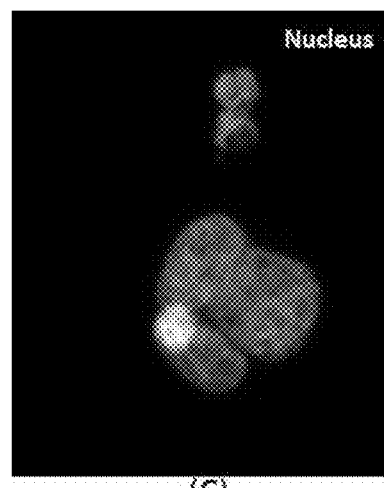
Figure 2D:
Figure 2E:
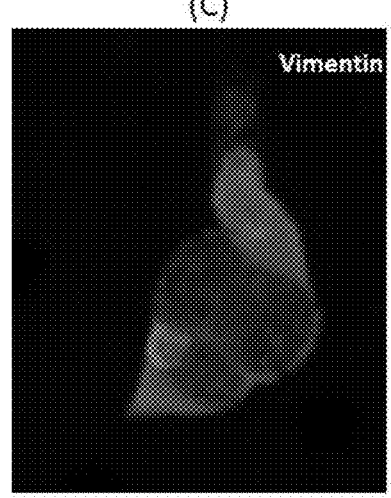
Figure 2F:
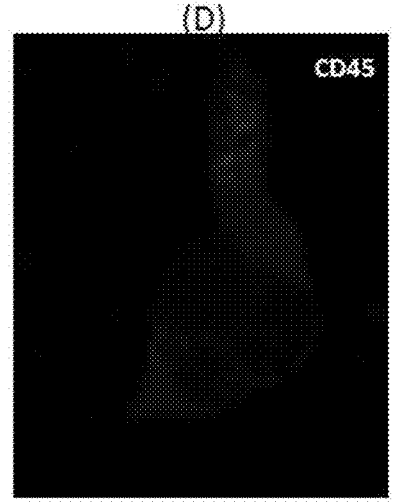
Figures 3A, 3B:
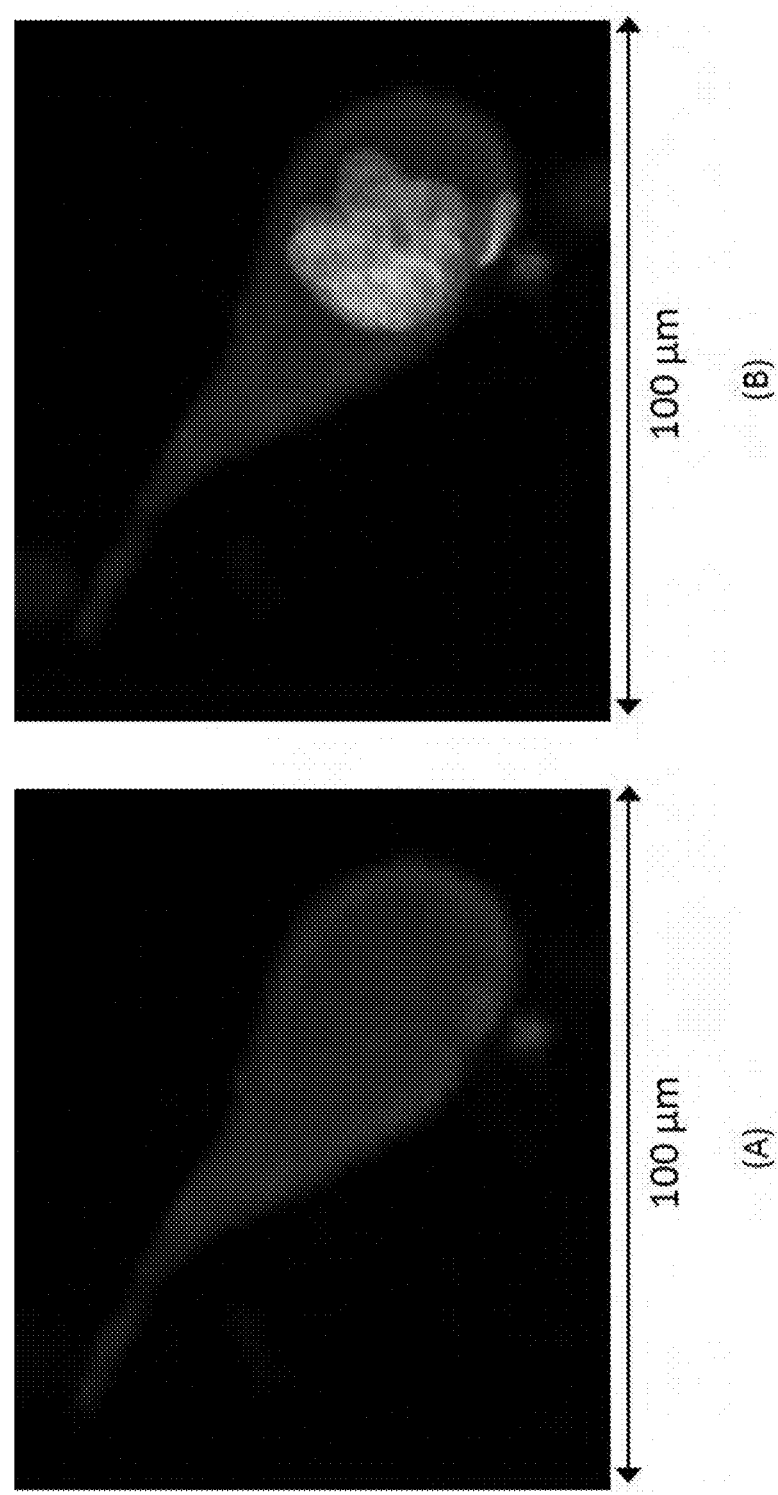
FIGS. 3A-3F show a CAML in the process of engulfing DNA fragment.
Figures 3C, 3D, 3E, 3F:
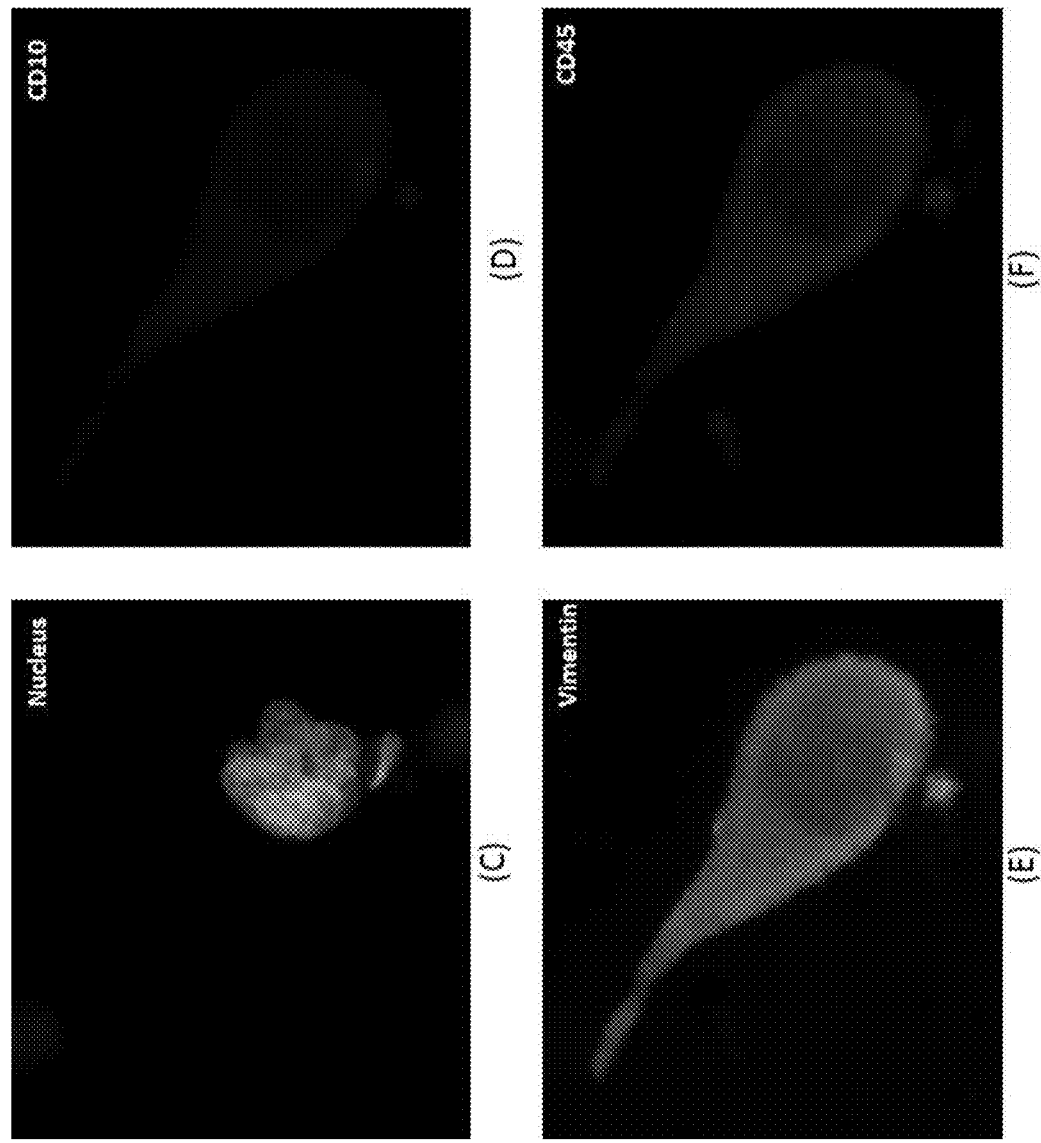
Figures 4A, 4B:
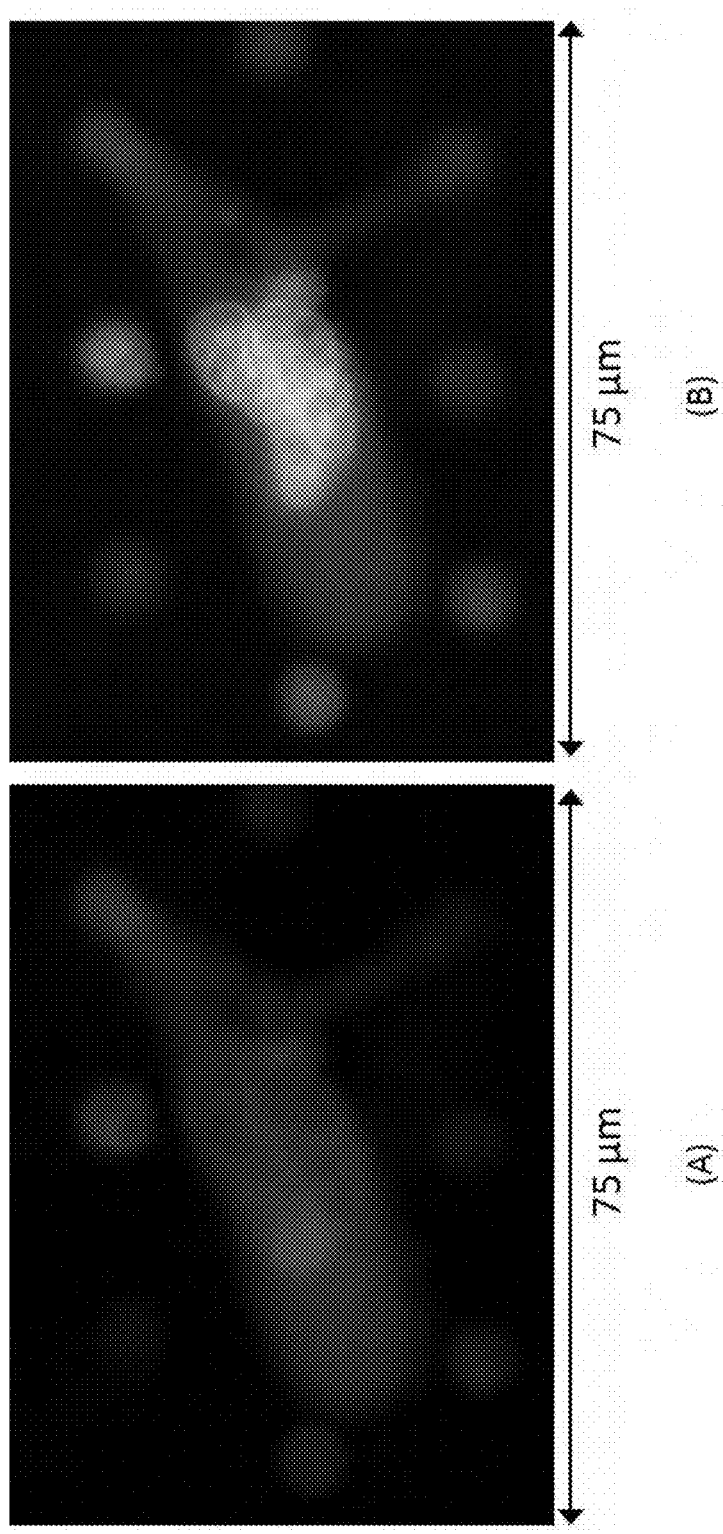
FIGS. 4A-4F show a CAML in the process of engulfing cytoplasm fragment.
Figures 4C, 4D, 4E, 4F:
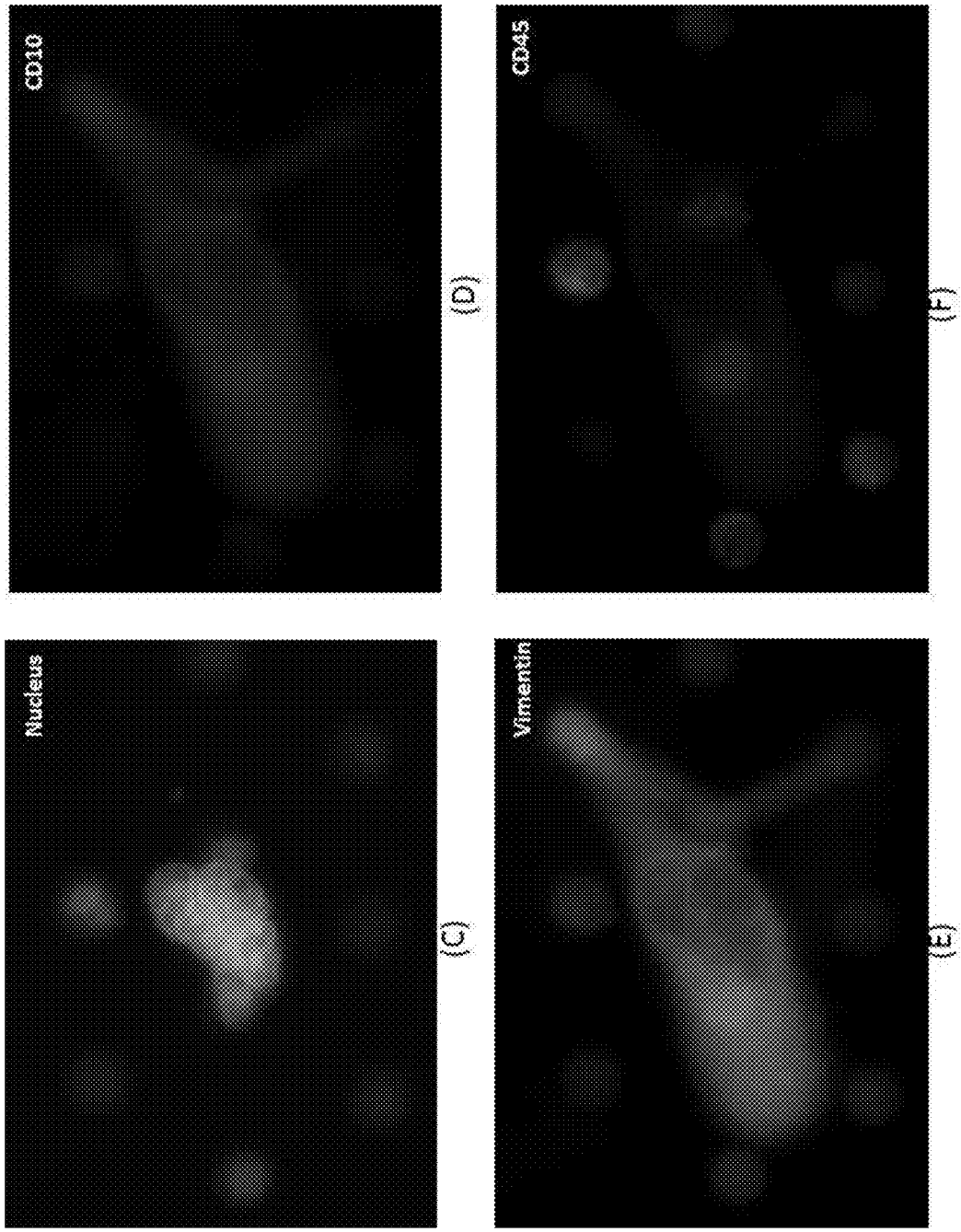
Figures 5A, 5B:
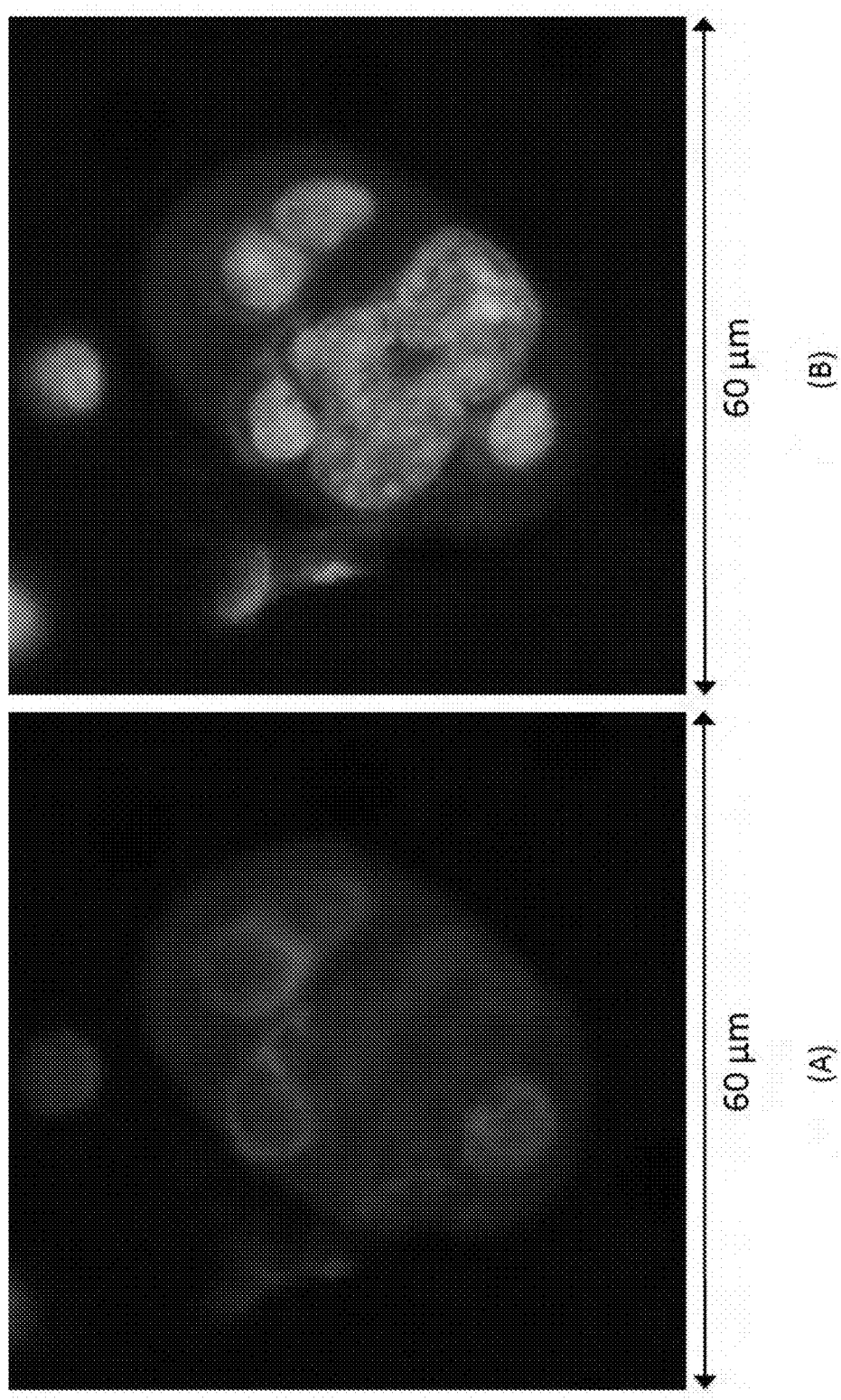
FIGS. 5A-5F show a CAML with four engulfed white blood cells.
Figures 5C, 5D, 5E, 5F:
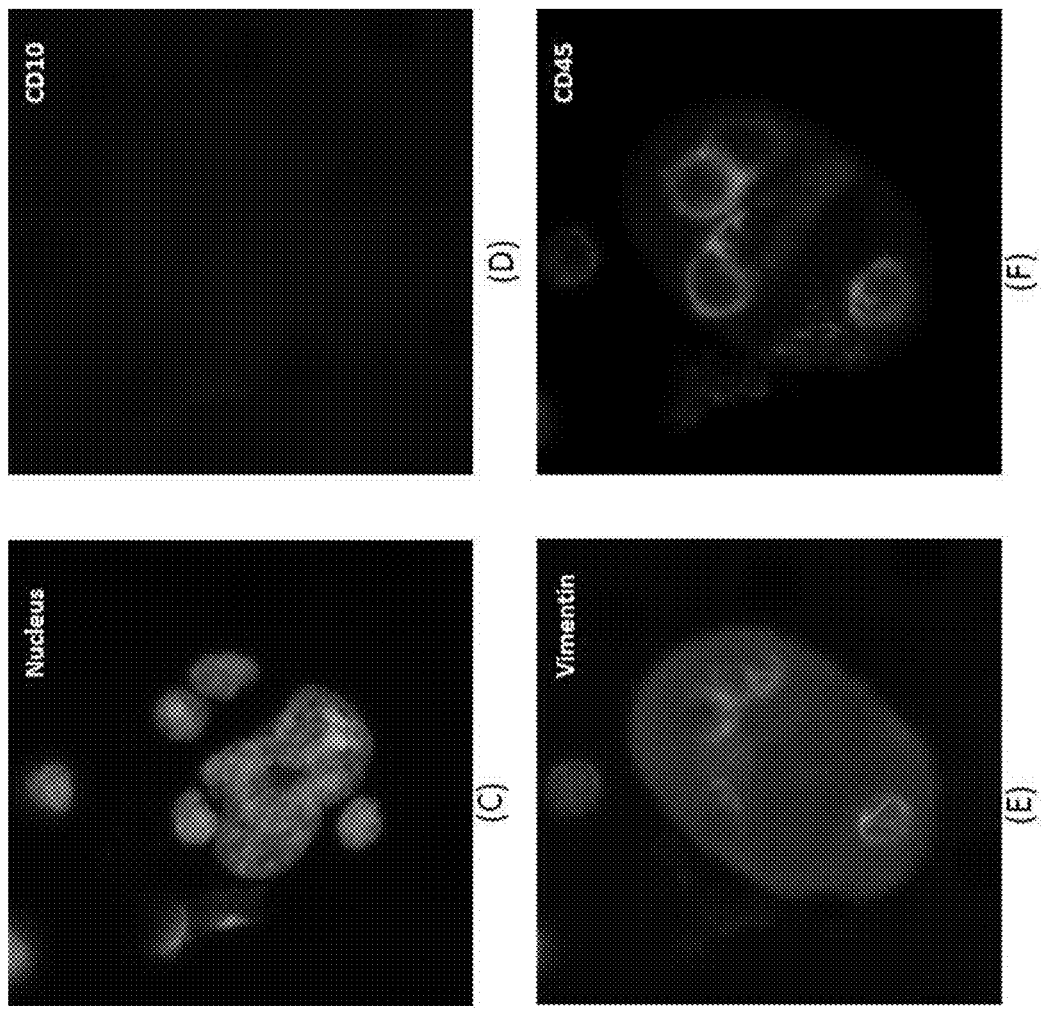
Figures 6A, 6B:
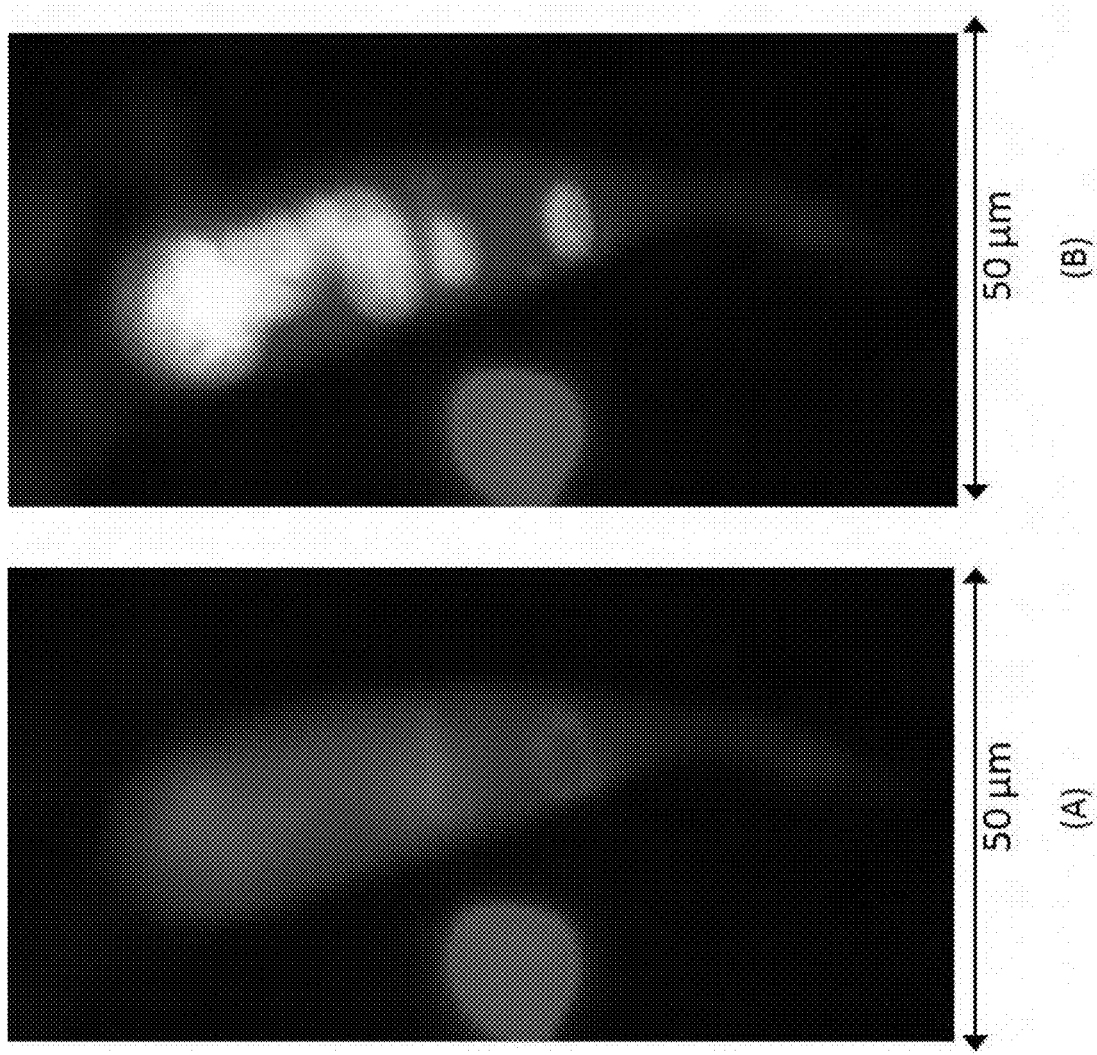
FIGS. 6A-6F show a CAML with two engulfed white blood cells.
Figures 6C, 6D, 6E, 6F:
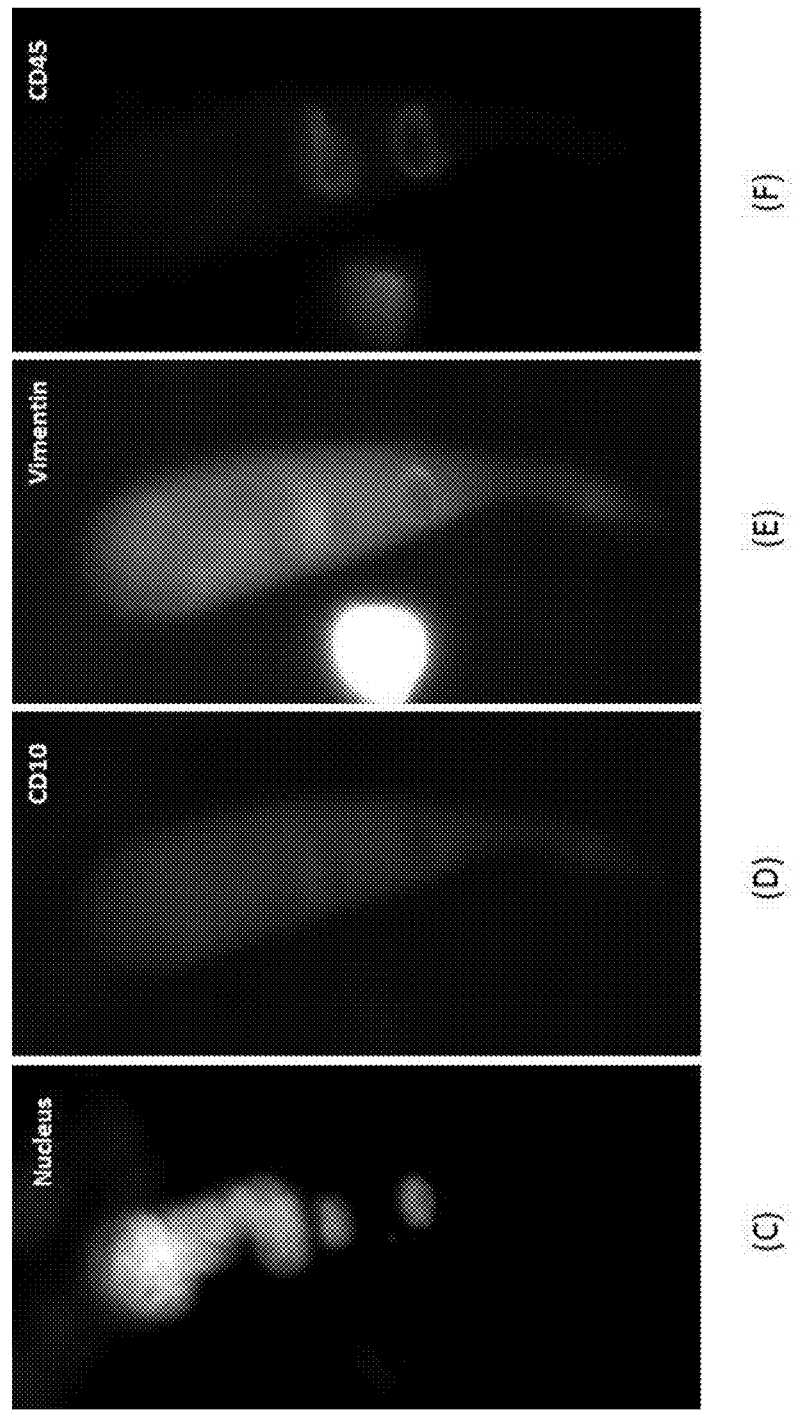
Figures 7A, 7B, 7C, 7D, 7E, 7F:
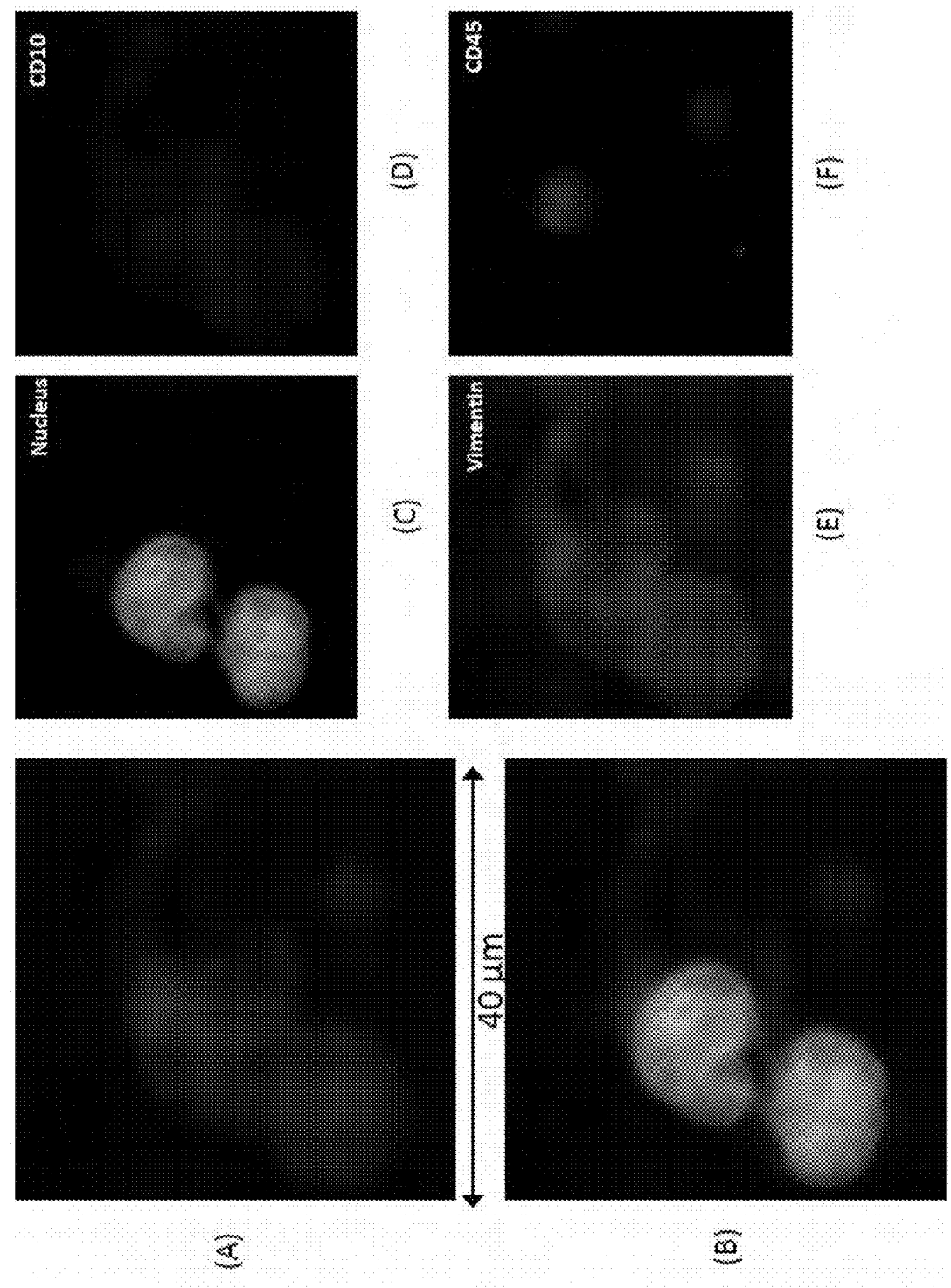
FIGS. 7A-7F show a CAML in division.
Figures 8A, 8B:
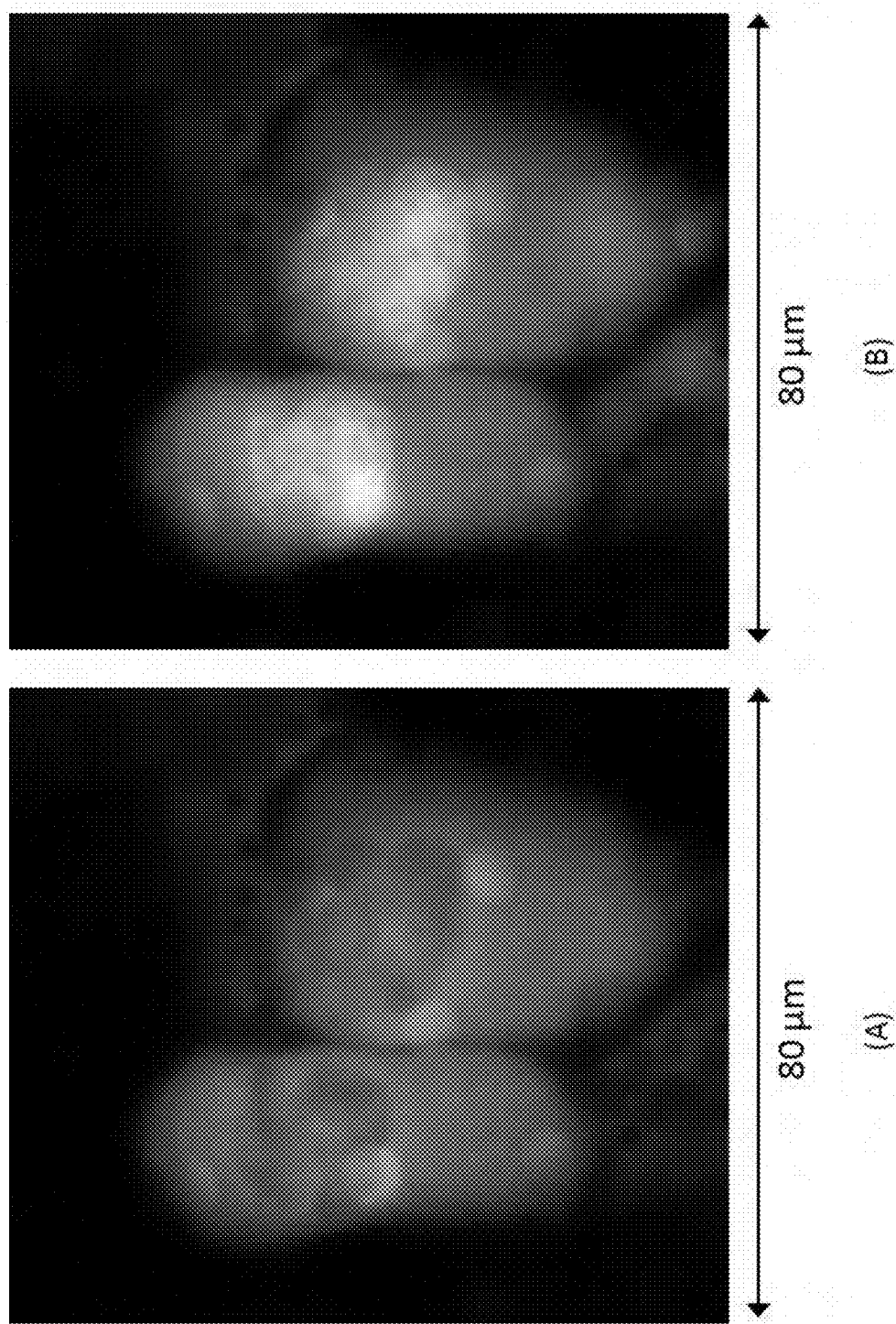
FIGS. 8A-8F show two CAMLs after division.
Figures 8C, 8D, 8E, 8F:
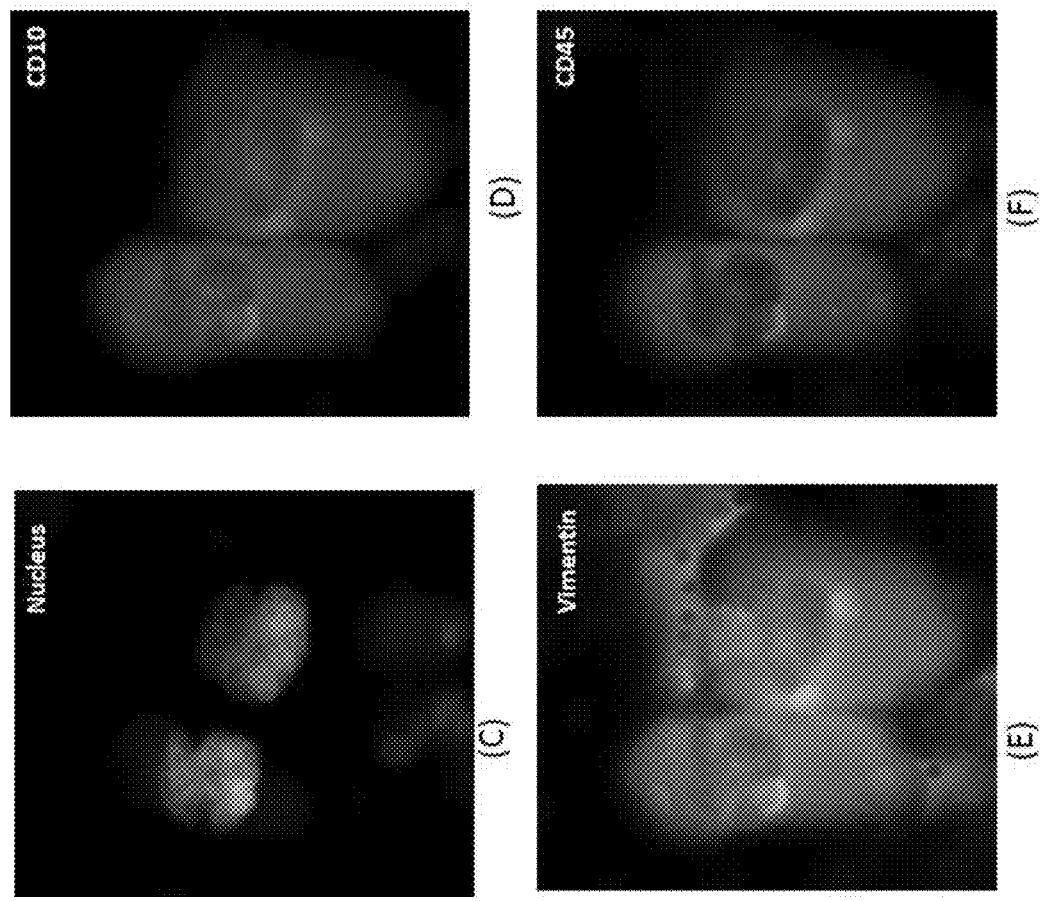
Figures 9A, 9B:
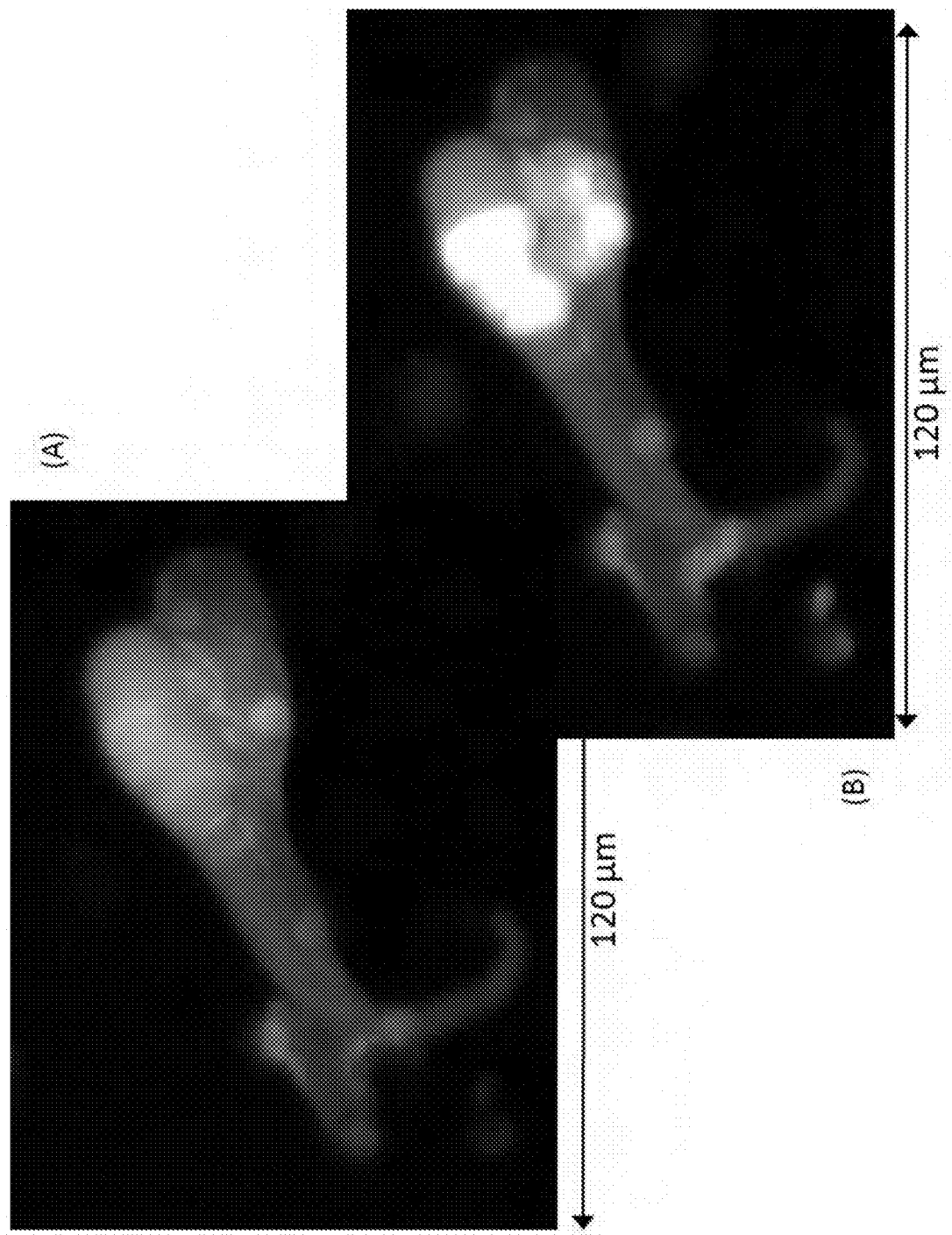
FIGS. 9A-9F show two CAMLs after division.
Figures 9C, 9D, 9E, 9F:
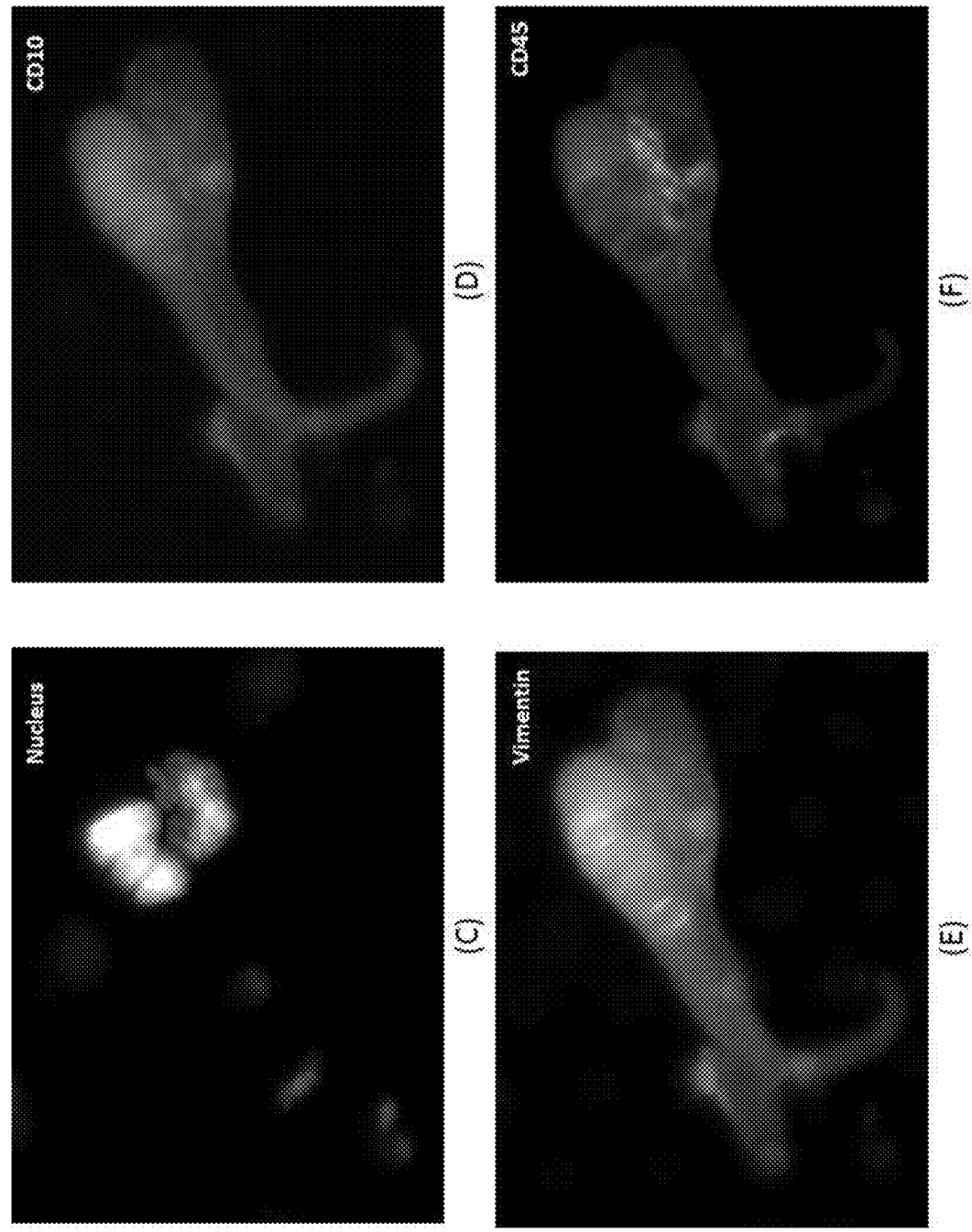

The matters defined in the description such as a detailed construction and elements are nothing but the ones provided to assist in a comprehensive understanding of the invention. Accordingly, those of ordinary skill in the art will recognize that various changes and modifications of the embodiments described herein can be made without departing from the scope and spirit of the invention.

Cancer is the most feared illness in the world, affecting all populations and ethnicities in all countries. In the United States alone, there are more than 12 million cancer patients, with 1.7 million new cancer cases and almost 0.6 million deaths per year. Cancer death worldwide is estimated to be about 8 million annually, of which 3 million occur in developed countries where patients have available treatment.

Ideally there is a biomarker that can (i) provide early detection of all solid tumors, especially for at risk groups such as smokers for lung cancer, (ii) confirm other indications of cancer, such as high PSA for prostate cancer, and/or (iii) provide early detection of cancer recurrence.

Oncologists need to know how best to treat newly diagnosed cancer patients. The current testing standard is a tissue biopsy, which is used to determine the cancer subtype, because therapeutic drugs are frequently effective only for specific subtypes. The biopsy method varies by location, but is invasive and can be risky.

To monitor treatment, oncologists need to know how well the drug is working for the patient, whether the dose should be adjusted, and whether the disease is spreading or responding to the drug. The common methods for answering these questions are x-ray computed tomography (CT) scans and magnetic resonance imaging (MRIs), both of which are expensive. Additionally, these methods cannot provide the necessary information until the tumor size has changed perceptibly.

Ninety percent of cancer patients die from metastasis, not from the primary tumor. The metastatic process involves tumor cells that break free of the primary carcinomas (solid tumors of epithelial cells) and enter the blood stream. These breakaway cancer cells are known as circulating tumor cells (CTCs). CTCs have the potential to be useful as a tool to determine therapy, monitor treatment, determine recurrence and provide prognostic information of survival. However, CTCs cannot be consistently collected from the blood even in stage III and IV cancers.

In this disclosure, a cell type is presented that is more consistently found in the blood of solid tumor patients from stage I-IV. These cells are macrophage-like cells that contain the same tumor markers as the primary tumor and they are termed circulating Cancer Associated Macrophage-Like cells (CAMLs) herein.

CTCs and CAMLs can be found from the same patient sample at the same time by size exclusion methods, such as by microfiltration methods. Microfilters can be formed with pores big enough to let all red blood cells and majority of white blood cells through and retain larger cells such as CTCs and CAMLs. Size exclusion methods have also been implemented by microfluidic chips.

CAMLs have many clinical utilities when used alone. Furthermore, CAMLs can be combined with other markers such as CTCs, free DNA in blood and free proteins in blood to further improve sensitivity and specificity of a diagnosis. This is especially true for CAMLs and CTCs because they can be isolated and identified at the same time.

Circulating Tumor Cells

The CTCs for many solid tumors express a number of cytokeratins (CKs). CK 8, 18, & 19 are the most commonly used in diagnostics, but surveying need not be limited to these markers. The surface of solid tumor CTCs usually express epithelial cell adhesion molecule (EpCAM). However, this expression is not uniform or consistent. CTCs should not express any CD45, because it is a white blood cell marker. In assays to identify tumor associated cells, such as CTCs and CAMLs, it is sufficient to use antibody against markers associated with the solid tumor such as CK 8, 18, & 19, or antibody against CD45 or DAPI. Combining the presence of staining with morphology, pathologically-definable CTCs (PDCTC), apoptotic CTCs and CAMLs can be identified (Adams, D. L., et al., Cytometric characterization of Circulating Tumor Cells captured by microfiltration and their correlation to the CellSearch® CTC test. Cytometry Part A 2015; 87A:137-144).

PDCTCs for solid tumors express CK 8, 18, & 19, and can be identified by the following characteristics:

A "cancer-like" nuclei stained by DAPI. The nuclei are usually large with dot patterns. The exception is when the cell is in division. The nucleus can also be condensed.

Expression of one or more of CK 8, 18 and 19; CTCs from epithelial cancers usually express at least CK 8, 18 and 19. The cytokeratins have a filamentous pattern.

Lack of CD45 expression.

An apoptotic CTC from a cancer that express CK 8, 18, & 19 is identified by the following characteristics:

A degrading nuclei.

Expression of one or more of CK 8, 18 and 19; the cytokeratins are not filamentous in pattern, but appear fragmented in the form of spots.

Lack of CD45 expression.

An apoptotic CTC of the present invention for solid tumors that express cytokeratins thus includes those CTCs having one, two or three of the following characteristics: (a) degrading nucleus; (b) expression of one or more of cytokeratin 8, 18 and 19, and wherein the cytokeratin is fragmented in the form of spots; and (c) CD45 negative phenotype.

Detection of many carcinomas, sarcomas and melanomas can be through the identification of a variety of other markers. For example, CTCs from renal cell cancer (RCC) and sarcomas express vimentin. CTC from bladder cancer usually express uroplakin and CK 8, 18 & 19 is weak. It is possible to stain the cells for many different markers of interest.

CTCs of the present invention can also be characterized based on one or more of the following characteristics: (i) number of CTCs; (ii) number of WBCs bound to the CTCs; (iii) status of nucleus; (iv) degree of cytokeratin 8 expression; (v) degree of cytokeratin 18 expression; (vi) degree of cytokeratin 19 expression; (vii) degree of EpCAM expression; (viii) degree of vimentin expression; (ix) degree of PD-L1 expression; (x) degree of uroplakin expression; (xi) cytokeratin morphology; (xii) location of markers (the location markers appear in CTCs, e.g., cytoplasm versus nucleus, can change at the different time points); and (xiii) intensity of marker staining. The number of CTC characteristics used in the methods of the invention can be 1, 2, 3, 4, 5, 6, 7, 8, 9, 10, 11, 12 or all 13.

Circulating Cancer Associated Macrophage-Like Cells (CAMLs)

CAMLs are characterized by having one or more of the following features:

CAMLs have a large atypical nucleus; multiple individual nuclei can be found in CAMLs, though enlarged fused nucleoli are common. CAML nuclei generally range in size from about 10 μm to about 70 μm in diameter, more commonly from about 14 μm to about 64 μm in diameter.

For many cancers, CAMLs express the cancer marker of the disease. For example, CAMLs associated with epithelial cancers may express CK 8, 18 or 19, vimentin, etc. The markers are typically diffused, or associated with vacuoles and/or ingested material. The staining pattern for any marker is nearly uniformly diffused throughout the whole cell. For sarcomas, neuroblastomas and melanomas, other markers associated with the cancers can be used instead of CK 8, 18, 19.

CAMLs can be CD45 positive.

CAMLs are large, approximately 20 micron to approximately 300 micron in size by diameter.

CAMLs are found in many distinct morphological shapes, including spindle, tadpole, round, oblong, two legs, more than two legs, thin legs, or amorphous shapes.

CAMLs typically have diffused cytokeratins.

If CAMLs express EpCAM, EpCAM is typically diffused throughout the cell, or associated with vacuoles and/or ingested material, and nearly uniform throughout the whole cell, but not all CAML express EpCAM, because some tumors express very low or no EpCAM.

If CAMLs express a marker, the marker is typically diffused throughout the cell, or associated with vacuoles and/or ingested material, and nearly uniform throughout the whole cell, but not all CAML express the same markers with equal intensity.

CAMLs express markers associated with the markers of the tumor origin; e.g., if the tumor is of prostate cancer origin and expresses PSMA, then CAML from this patient also expresses PSMA. Another example, if the primary tumor is of pancreatic origin and expresses PDX-1, then CAML from this patient also expresses PDX-1. If the primary tumor or CTC of the cancer origin express CXCR-4, then CAMLs from the patient also express CXCR-4.

If the primary tumor or CTC of the cancer origin expresses a biomarker of a drug target, CAMLs express markers associated with the markers of the drug target. An example of a biomarker of immunotherapy is PD-L1.

CAMLs express monocytic markers (e.g. CD11 c, CD14) and endothelial markers (e.g. CD146, CD202b, CD31). CAMLs also have the ability to bind Fc fragments.

CAMLs of the present invention thus includes those CAMLs having one, two, three, four or five of the following characteristics: (a) large atypical nucleus having a size of about 14-64 μm; (b) expression of one or more of cancer marker associated with the tumor, wherein the marker is diffused, or associated with vacuoles and/or ingested material; (c) cell size ranging from about 20 micron to about 300 microns; (d) morphological shape selected from the group consisting of spindle, tadpole, round, oblong, one or more legs, thin legs and amorphous; and (e) CD45 positive phenotype. CAMLs of the present invention also include those CAMLs having one, two, three or four of the following additional characteristics: (f) expression of diffuse EpCAM or vimentin with nearly uniform distribution; (g) expression of one or more markers of a primary tumor; (h) expression of myeloid CD14 marker; (i) expression of monocytic CD11C markers; and (j) expression of endothelial CD146, CD202b, and CD31 markers. In a particular aspect, CAMLs of the present invention have each of the additional characteristics (f)-(j).

CAMLs of the present invention can also be characterized based on one or more of the following characteristics: (i) number of CAMLs; (ii) average size of the CAMLs (CAML cell sizes range from about 20 micron to about 300 microns in diameter); (iii) average size of the nuclei of the CAMLs (CAMLs have a large atypical nucleus having a size of about 14-64 μm in diameter); (iv) morphological shape of the CAMLs (CAML shapes include spindle, tadpole, round, oblong, two legs, more than two legs, thin legs, or amorphous); (v) CD14 positive phenotype; (vi) degree of CD45 expression; (vii) degree of EpCAM expression; (viii) degree of vimentin expression; (ix) degree of PD-L1 expression; (x) degree of monocytic CD11C marker expression; (xi) degree of endothelial CD146 marker expression; (xii) degree of endothelial CD202b marker expression; (xiii) degree of endothelial CD31 marker expression; (xiv) location of markers (the location markers appear in CAMLs, e.g., cytoplasm versus nucleus, can change at the different time points); (xv) presence of one or more markers associated with the cancer in the CAMLs, wherein the marker is diffused, or associated with vacuoles and/or ingested material (e.g., for epithelial cancer, the markers are cytokeratin 8, 18, and 19); and (xvi) intensity of marker staining. The number of CAML characteristics used in the methods of the invention can be 1, 2, 3, 4, 5, 6, 7, 8, 9, 10, 11, 12, 13, 14, 15 or all 16.

Under certain situations, it may be most suitable to stain CAMLs by H&E or other colorimetric stains.

FIG. 1 contains a collage of CAMLs showing many of the different CAML morphologies and signal variation from separate prostate, breast and pancreatic patient samples (Adams, D., et al., Circulating giant macrophages as a potential biomarker of solid tumors. *PNAS* 2014, 111(9): 3514-3519): (FIG. 1A) pancreatic, (FIG. 1B) breast, (FIG. 1C) breast, (FIG. 1D) breast, (FIG. 1E) prostate, (FIG. 1F) pancreatic, (FIG. 1G) pancreatic, (FIG. 1H) prostate, and (FIG. 1I) prostate. Examples of morphology variants are as follows: amorphous (FIG. 1A), oblong (FIGS. 1B and 1G), spindle (FIGS. 1C, 1F, 1I, 3, 5, 6), round (FIG. 1D) and tadpole (FIGS. 1E & 1H). Color differences occur from varying degrees of protein expression from antibody reaction to EpCAM, cytokeratin and CD45.

FIGS. 2-13 show CAMLs stained with DAPI, CD10, vimentin and CD45, where (FIG. 2A) frames show merged microscope image DAPI (blue), CD10 (green), vimentin (red) and CD45 (violet), (FIG. 2B) frames show merged microscope image DAPI (white), CD10 (green), vimentin (red) and CD45 (violet), (FIG. 2C) frames show DAPI (white), (FIG. 2D) frames show CD10 (white), (FIG. 2E) frames show vimentin (white), and (FIG. 2F) frames show CD45 (white). Frame (FIG. 2B) with nucleus in white provides better image quality for some cells. Those cells possess the properties of CAMLs described in paragraphs above. The choice of the stain was chosen because the source of the cells is kidney cancer patients.

FIGS. 2A-2F show engulfed DNA material at the end of top leg. FIGS. 3A-3F show a CAML in the process of engulfing a cell, where the DNA material is already in the CAML and some degraded cell cytoplasm is still partially outside the CAML. FIGS. 4A-4F show a CAML in the process of engulfing degraded cellular material. This is most visible in the vimentin channel. FIGS. 5A-5F show a CAML with four engulfed CD45 positive white blood cells. FIGS. 6A-6F show a CAML with two engulfed CD45 positive white blood cells. FIGS. 7A-7F appear to show a CAML in the process of dividing. FIGS. 8A-8F show two similar side-by-side CAMLs suggesting the two cells might have come from the same origin. FIGS. 9A-9F show another example of two similar side-by-side CAMLs.

Figures 10A, 10B:
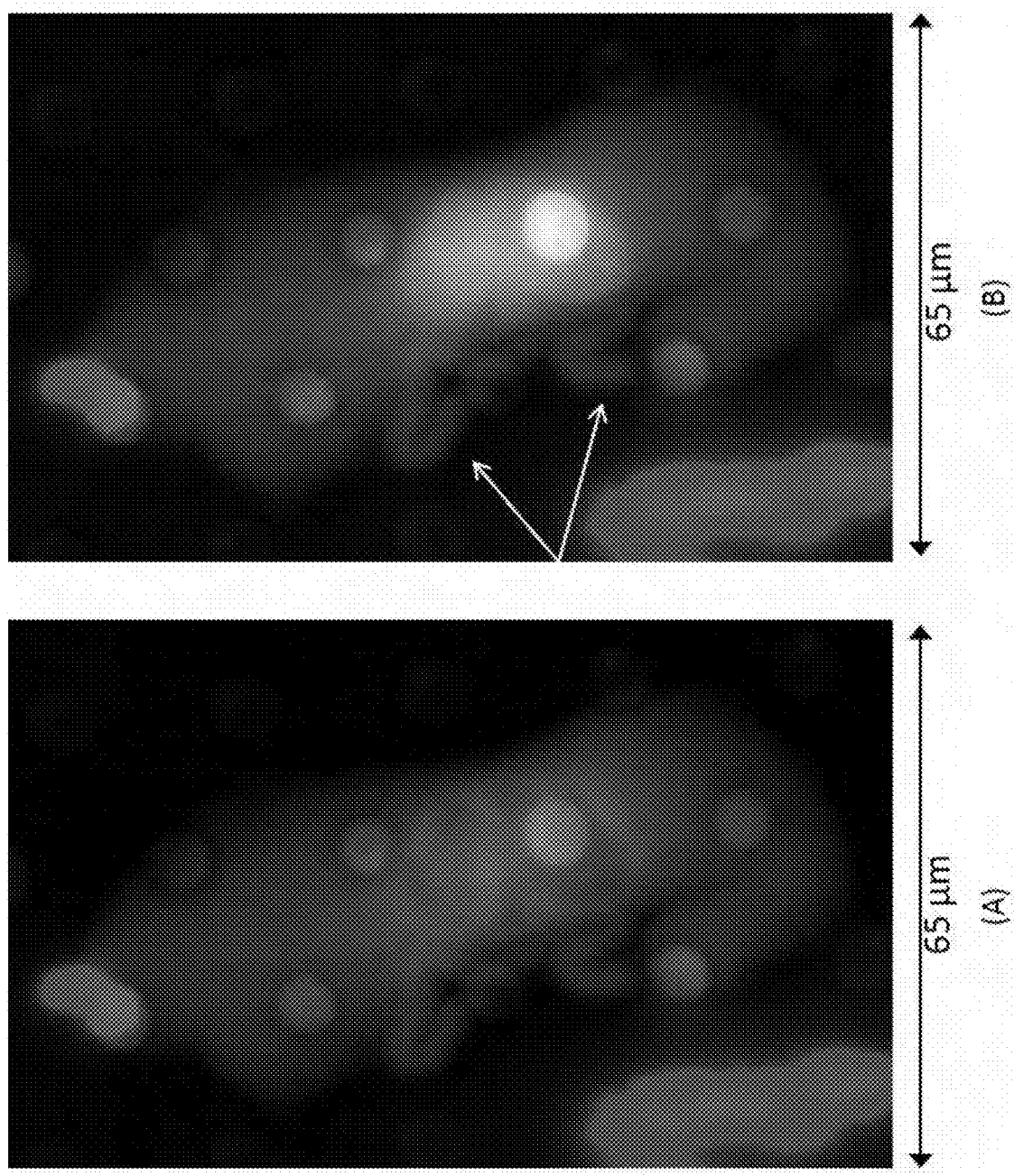
FIGS. 10A-10F show a CAML with two small arms.
Figures 10C, 10D, 10E, 10F:
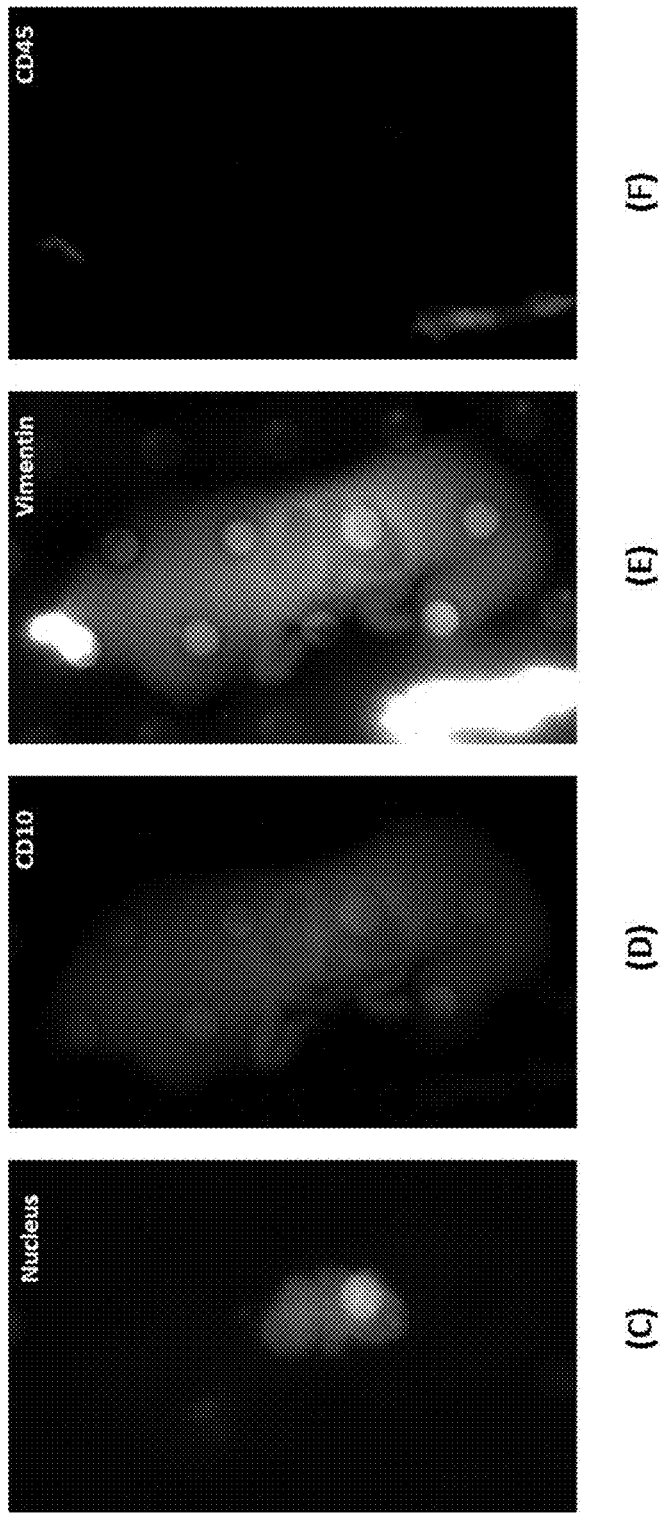
Figures 11A, 11B:
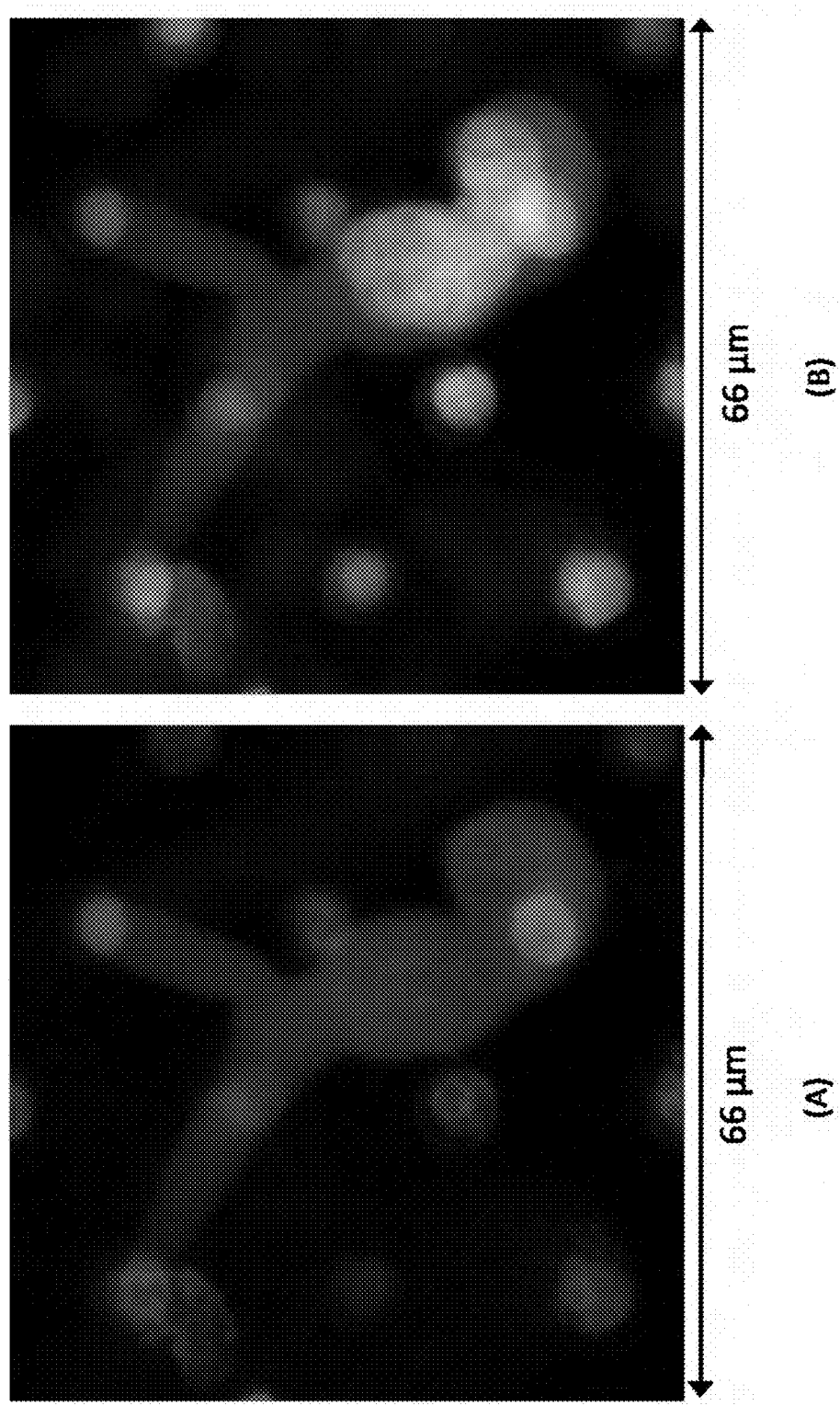
FIGS. 11A-11F show a CAML with two legs on the same side.
Figures 11C, 11D, 11E, 11F:
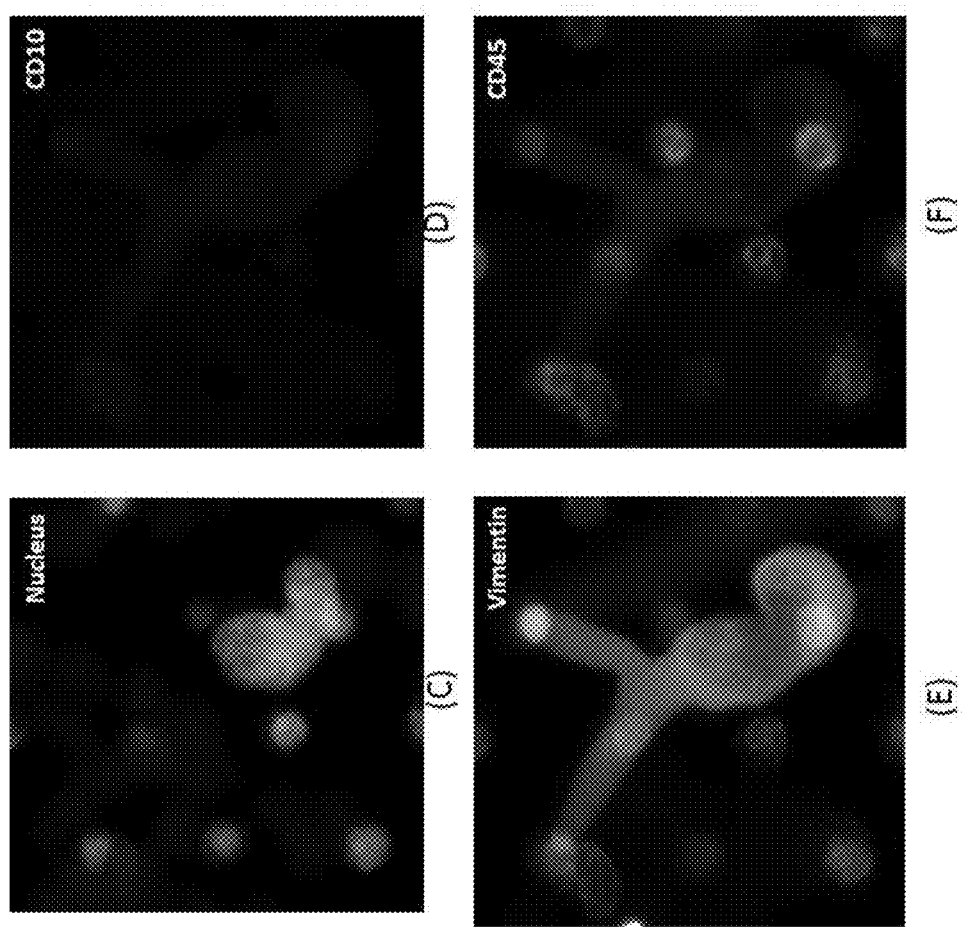
Figures 12A, 12B:
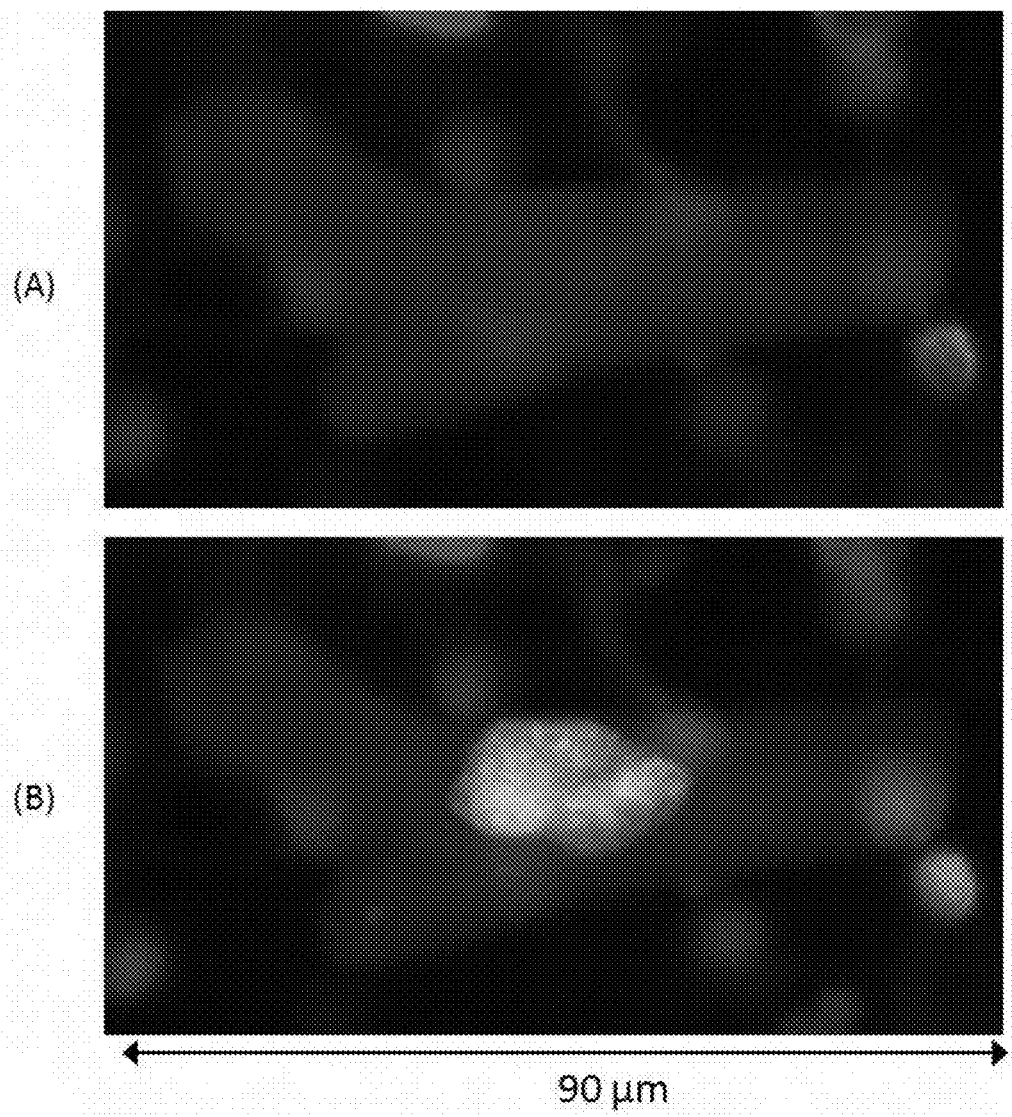
FIGS. 12A-12F show a CAML with two legs on the same side.
Figures 12C, 12D, 12E, 12F:
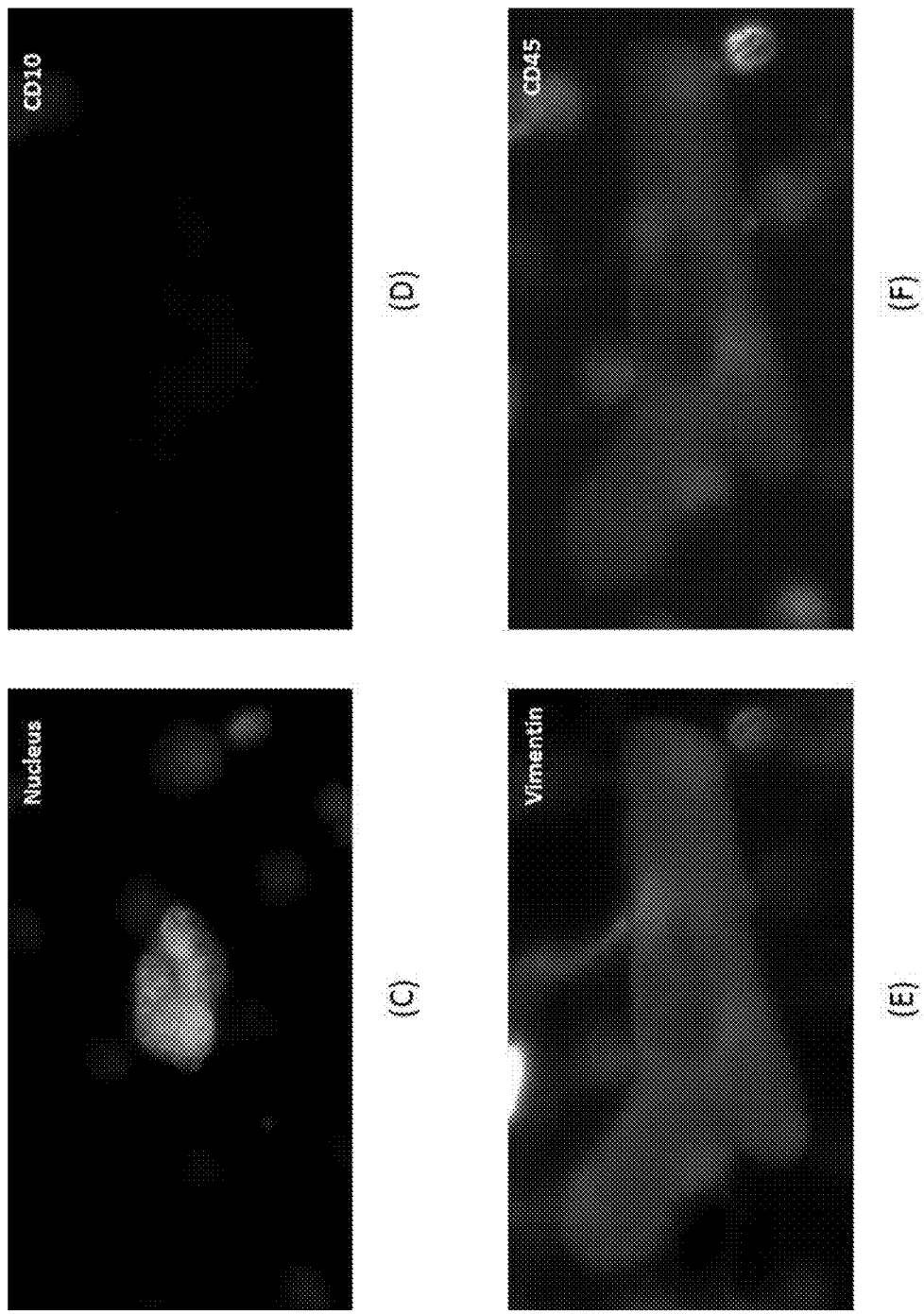
Figures 13A, 13B:
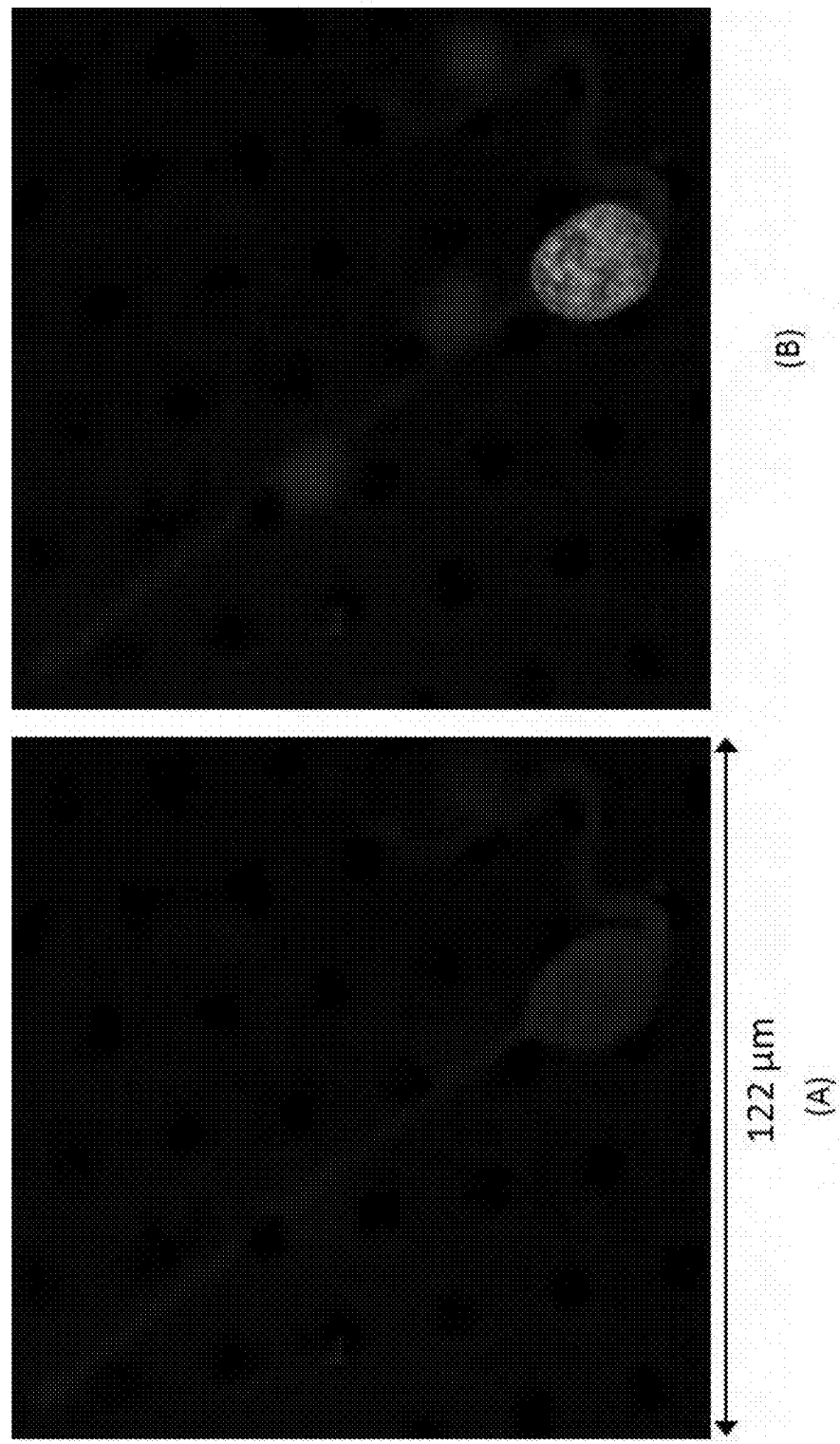
FIGS. 13A-13F show a CAML with very thin legs and rather regular nucleus.
Figures 13C, 13D, 13E, 13F:
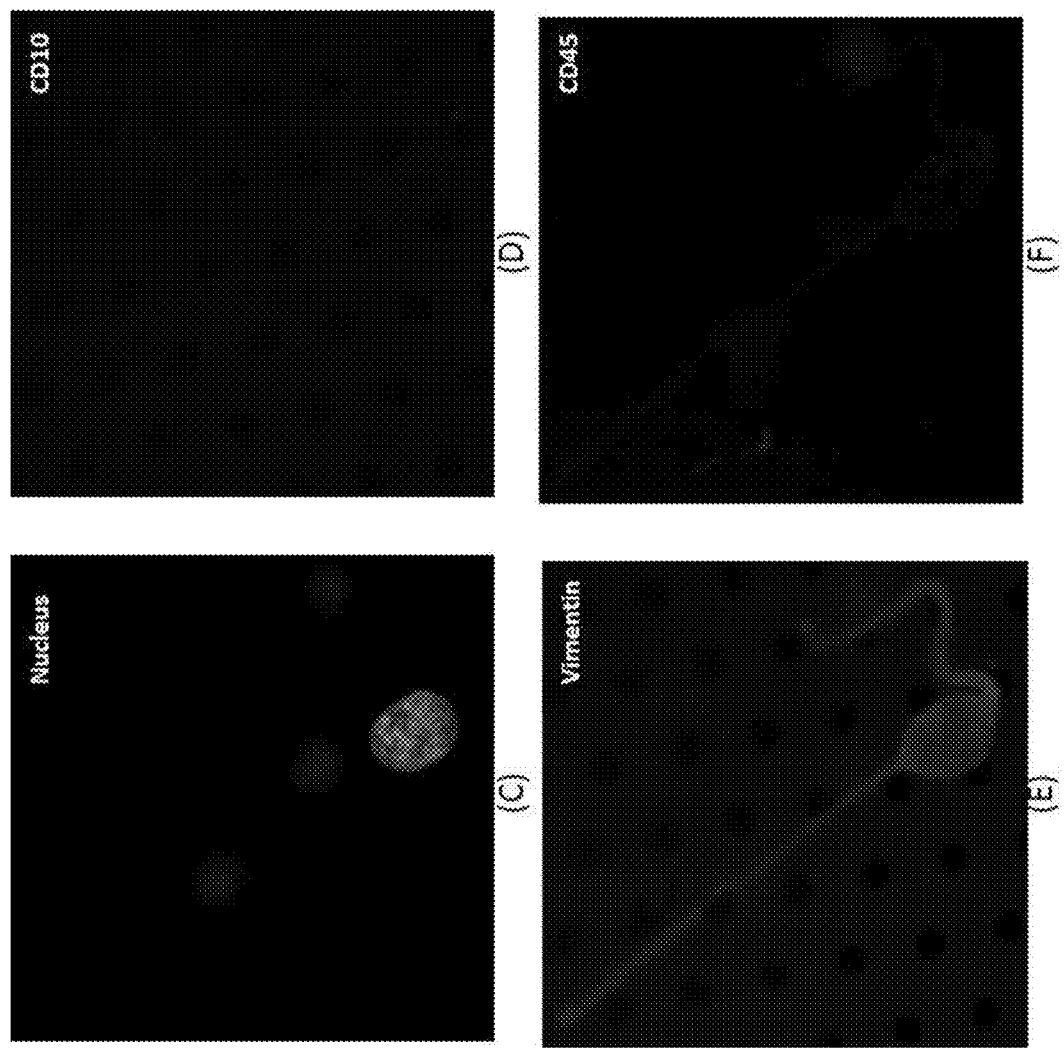
Figures 14A, 14B:
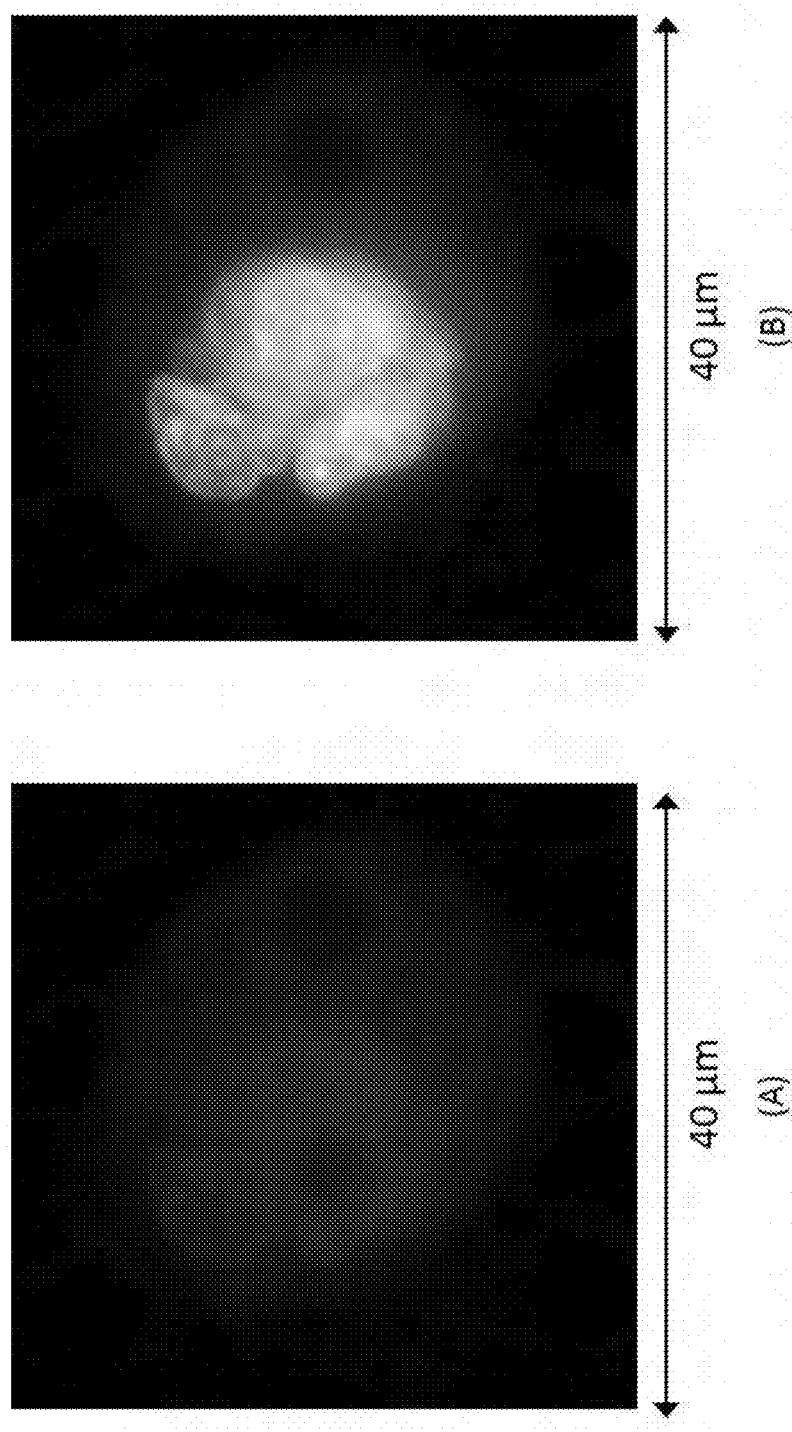
FIGS. 14A-14F show a CAML isolated from a subject having a viral infection.
Figures 14C, 14D, 14E, 14F:
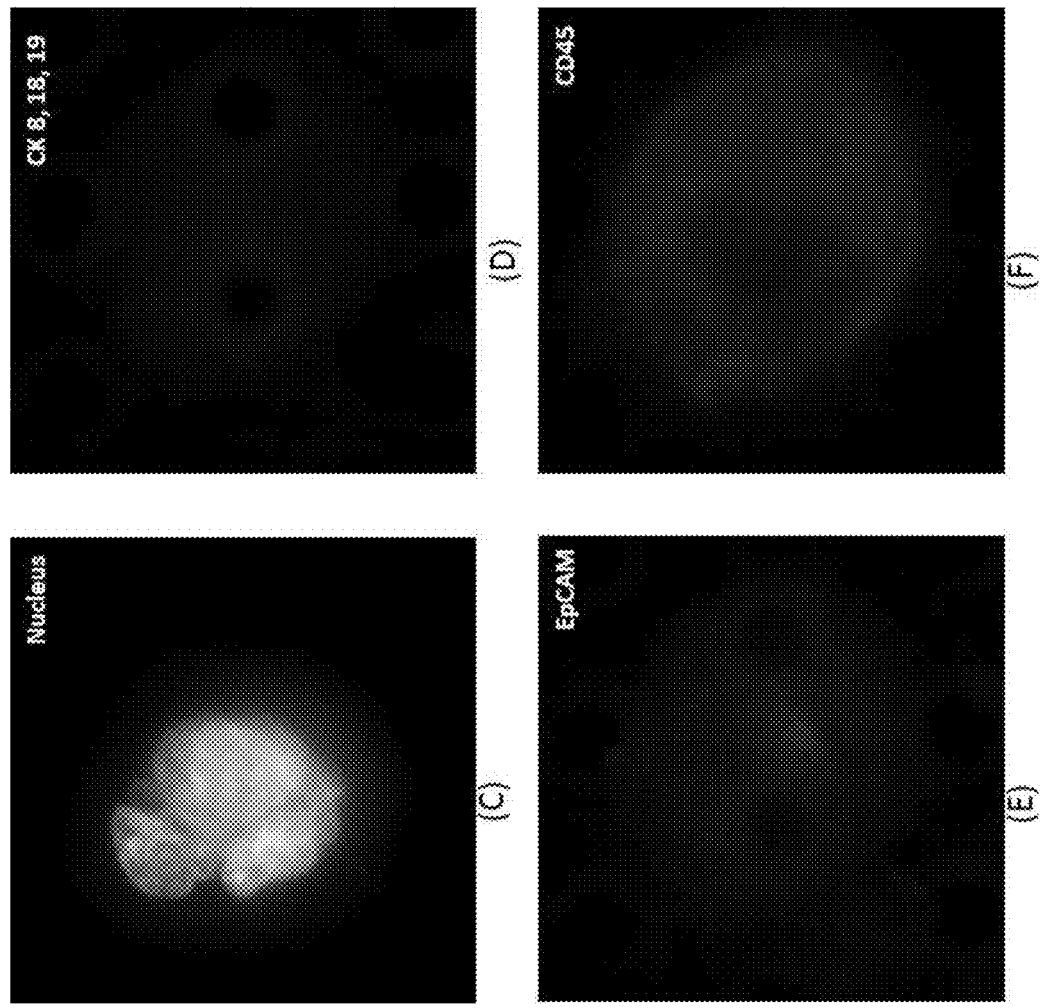

FIGS. 10-12 show additional morphologies of CAML not identified in FIG. 1. FIGS. 10A-10F show a CAML with two small legs on the left side of cell. FIGS. 11A-11F show a CAML with two legs on the same side. FIGS. 12A-12F show a CAML with one leg on the right side and two legs on the left side of the nucleus. FIGS. 13A-13F show a CAML with very thin legs and large single nucleus. FIGS. 14A-14F show a CAML found in patient with HSV-2 viral infection.

Body's Immune Response to CTCs—T-Cells Bound to CTCs

When a tumor cell enters the blood stream, the CTC should be attacked by T-cells, resulting in the death of the tumor cell. When this happens, one or more T-cells will be bound to the CTC, resulting in the death of the CTC and eventual degradation of the CTC. T-cells are a subtype of white blood cell. The CD45 marker stains WBCs and is not specific to T-cells. T-cells can be differentiated from granulocytes by the morphology of the nucleus. T-cells have a single nucleus approximately round and smaller than 8 microns. Filtration of the blood can capture white blood cells (WBCs) bound to the CTCs. The presence of WBCs bound to CTCs in the blood is an indication of presence of solid tumor and also body's ability to eliminate the solid tumors. A determination on the number of T-cells bound to CTCs can thus be used in diagnostics.

Figures 15A, 15B, 15C, 15D, 15E, 15F:
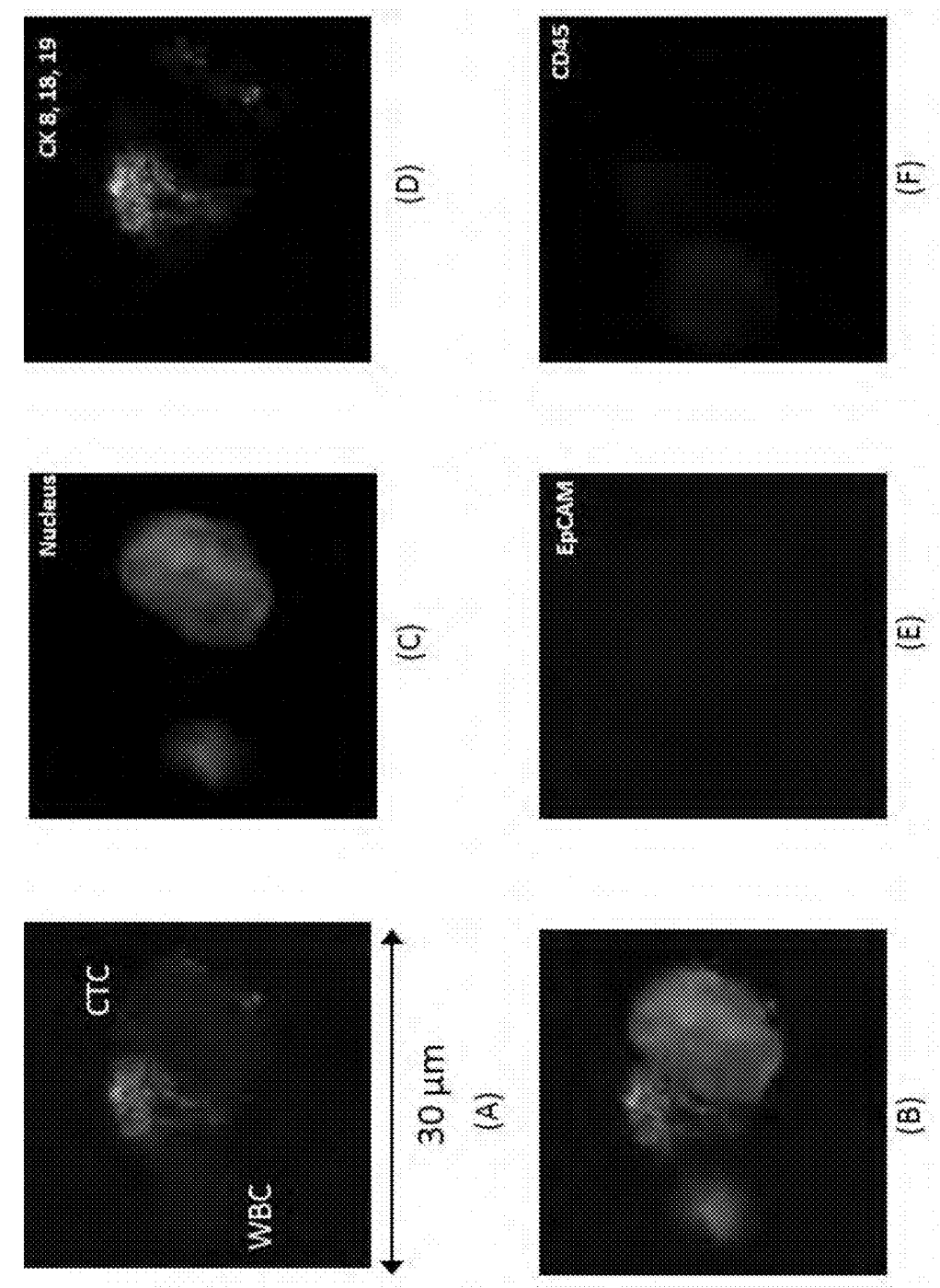
FIGS. 15A-15F show a WBC bound to a CTC from a breast cancer patient.
Figures 16A, 16B, 16C, 16D, 16E, 16F:
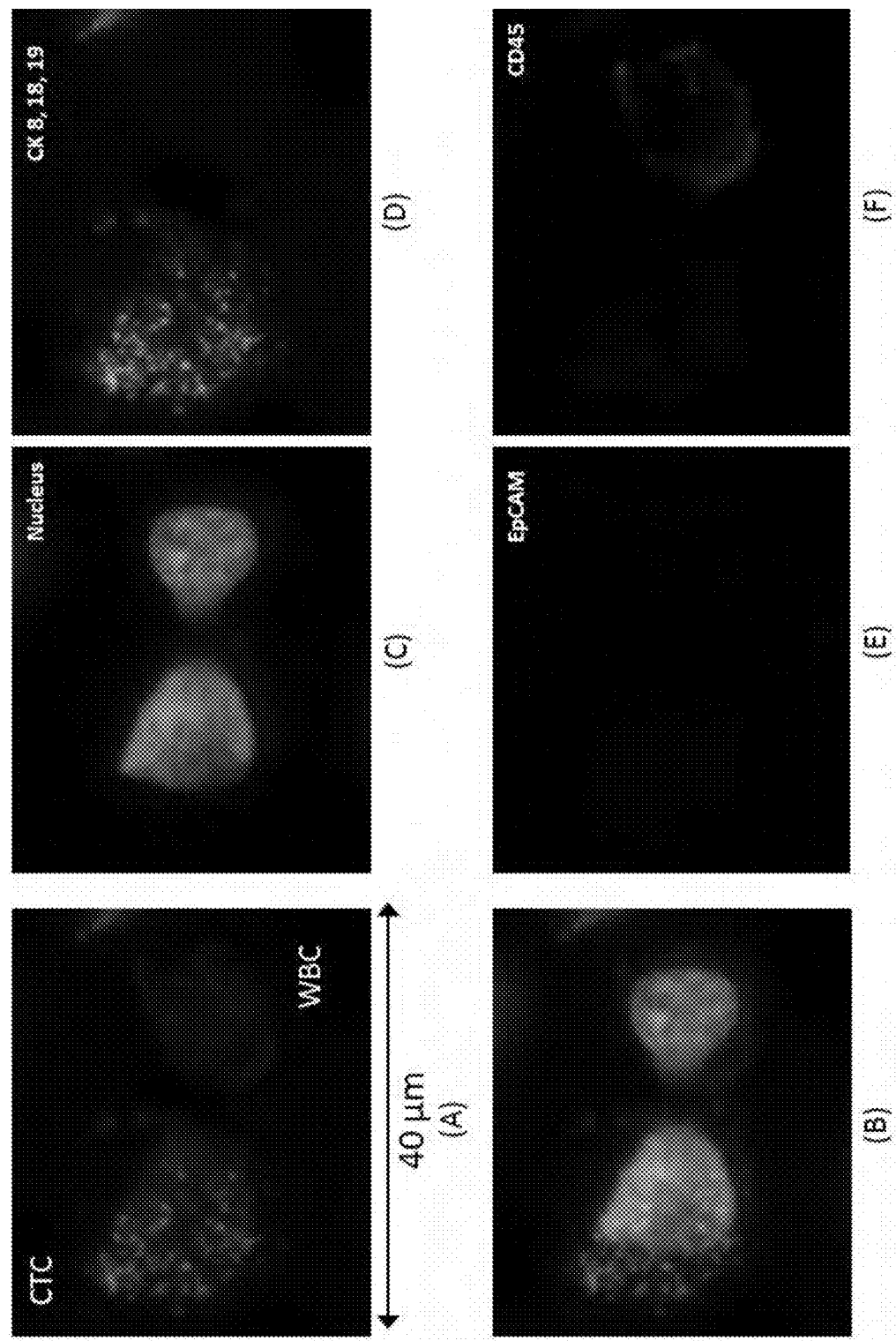
FIGS. 16A-16F show a WBC bound to a CTC from a breast cancer patient.
Figures 17A, 17B, 17C, 17D, 17E, 17F:
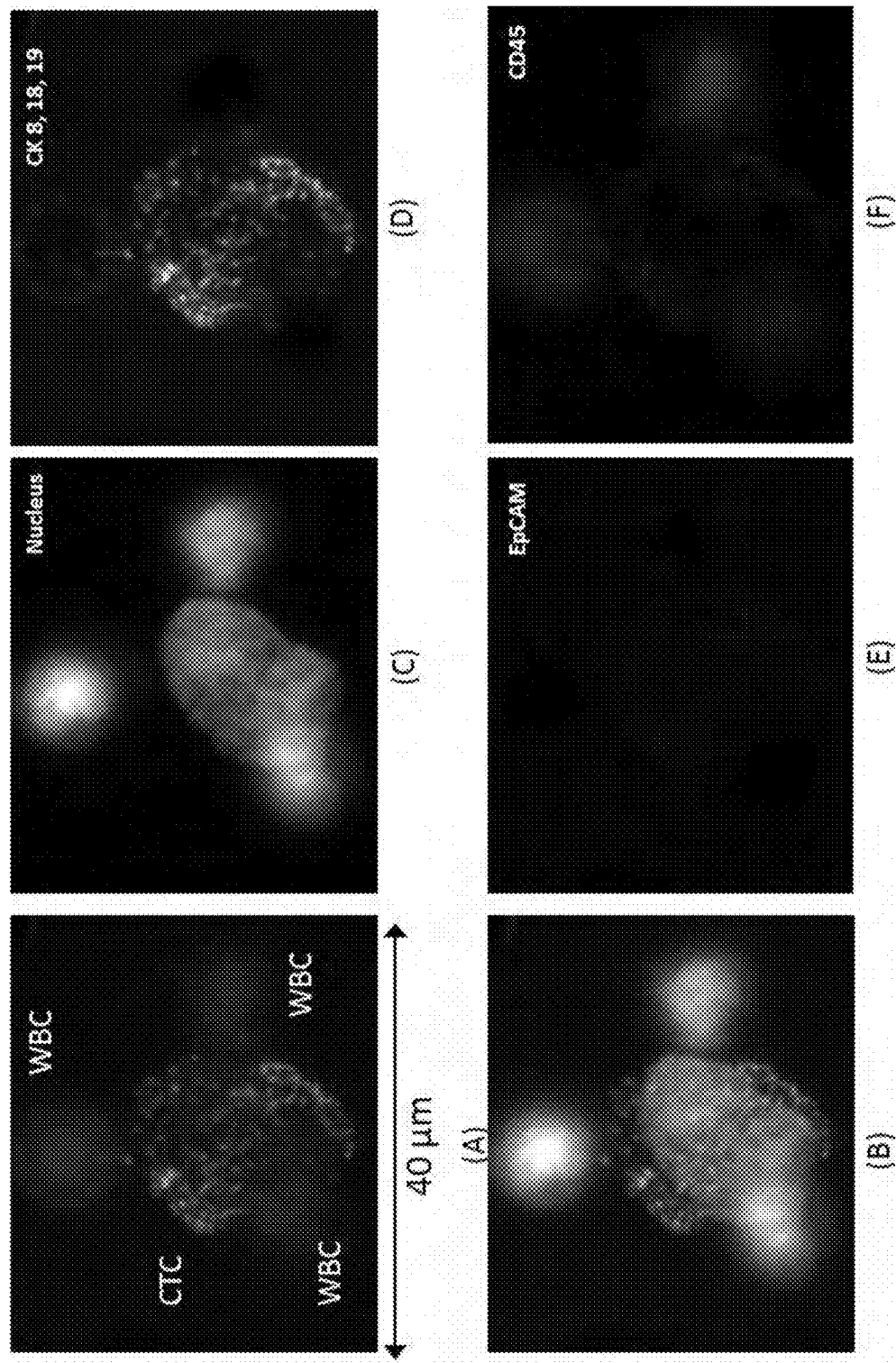
FIGS. 17A-17F show a WBC bound to a CTC from a breast cancer patient.
Figures 18A, 18B, 18C, 18D, 18E, 18F:
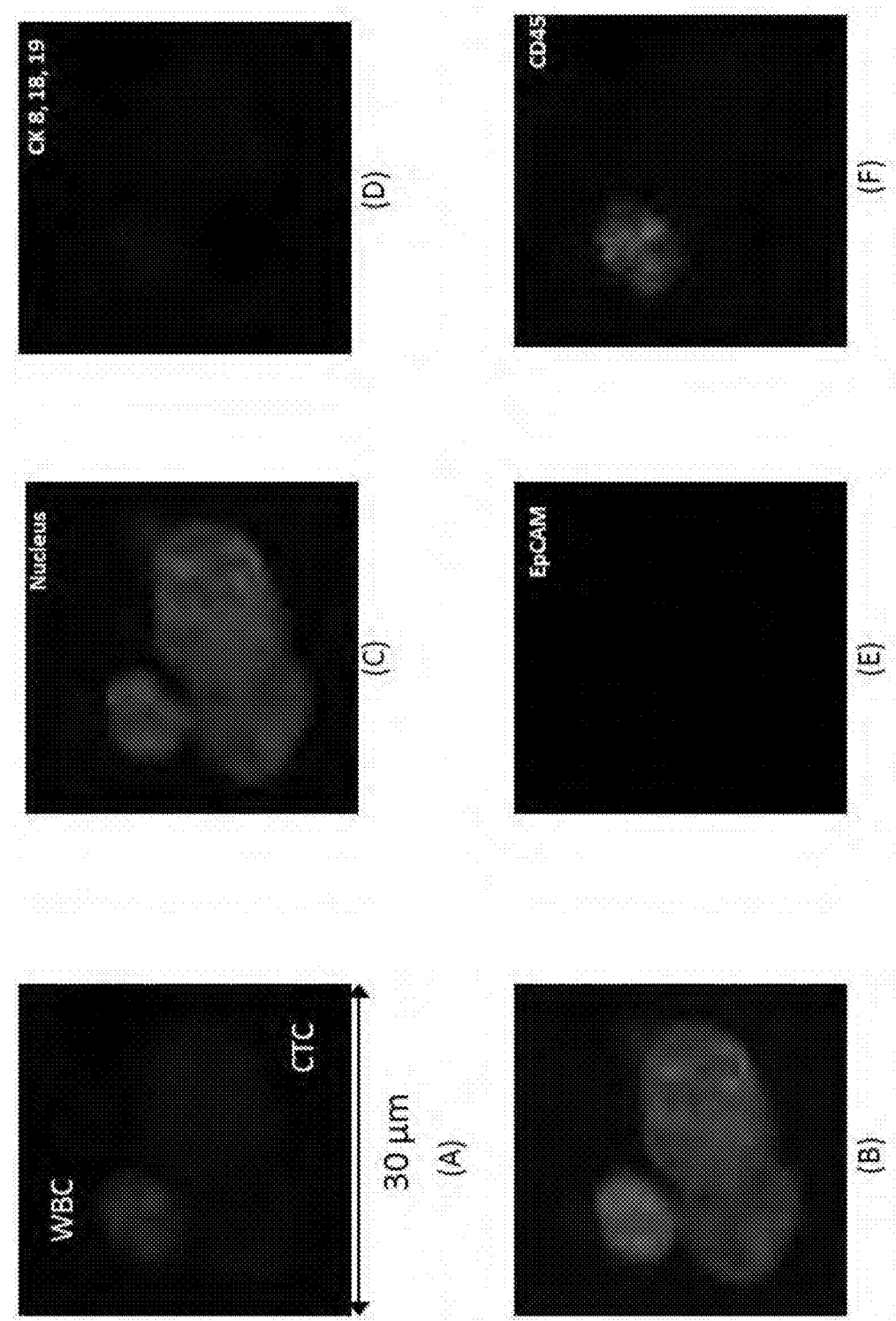
FIGS. 18A-18F show a WBC bound to a CTC from a breast cancer patient.

The markers of the tumor cell and the T-cell can be exchanged among the two cells when they come into contact. FIGS. 15-18 show WBCs bond to CTCs found in the blood of breast cancer patients. The markers used for the breast cancer patients are DAPI, CK 8, 18 & 19, EpCAM and CD45. FIGS. 15-16 show the CTCs are apoptotic with CK 8, 18, and 19 degraded to spots. FIG. 18 shows a much degraded CTC losing both CK and EpCAM markers with no cytoplasm. It is often observed that the nuclei of the WBC and the CTCs are pulled towards each other as shown in FIG. 16.

Figures 19A, 19B, 19C, 19D, 19E, 19F:
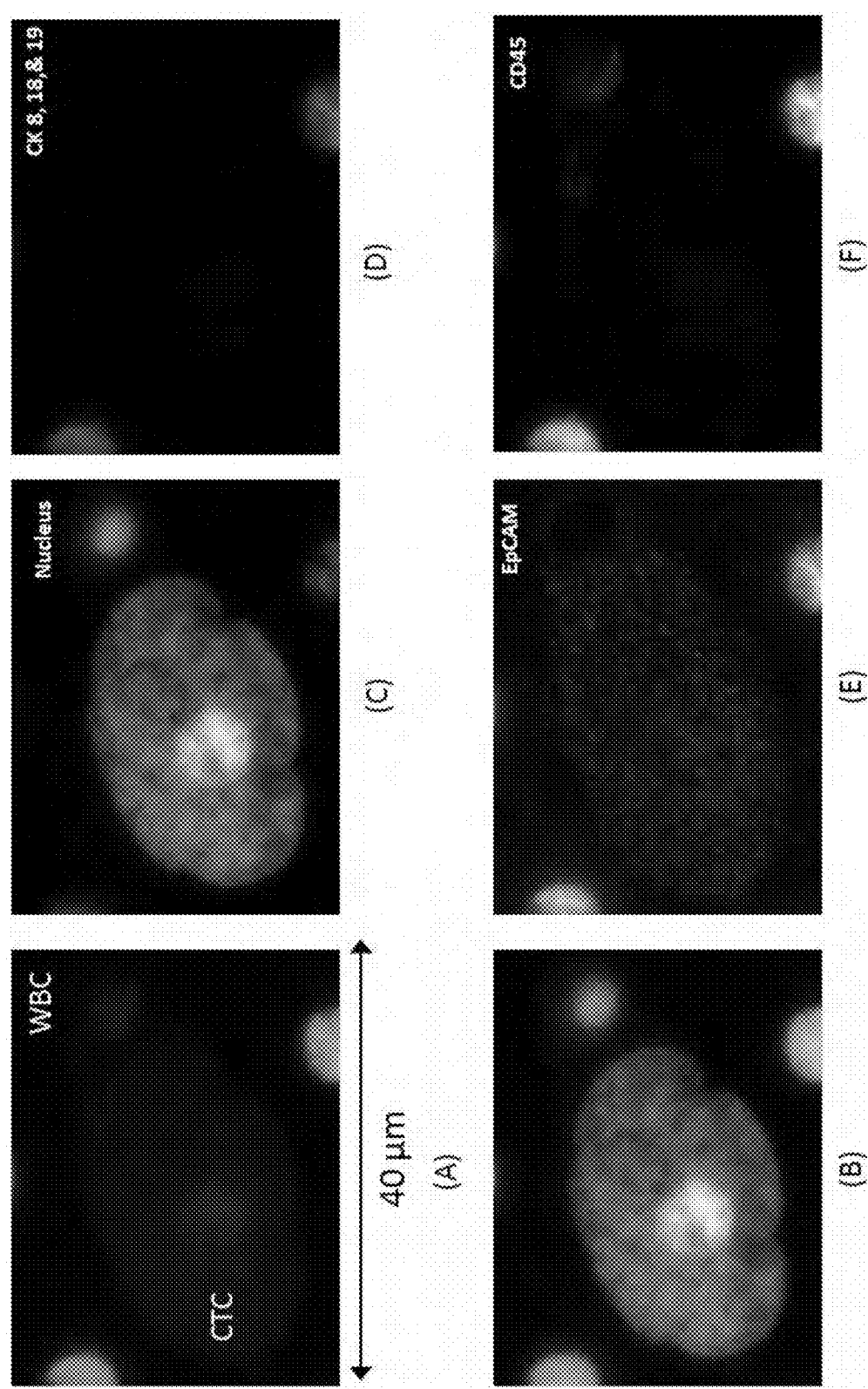
FIGS. 19A-19F show a WBC bound to a CTC from a bladder cancer patient.
Figures 20A, 20B, 20C, 20D, 20E, 20F:
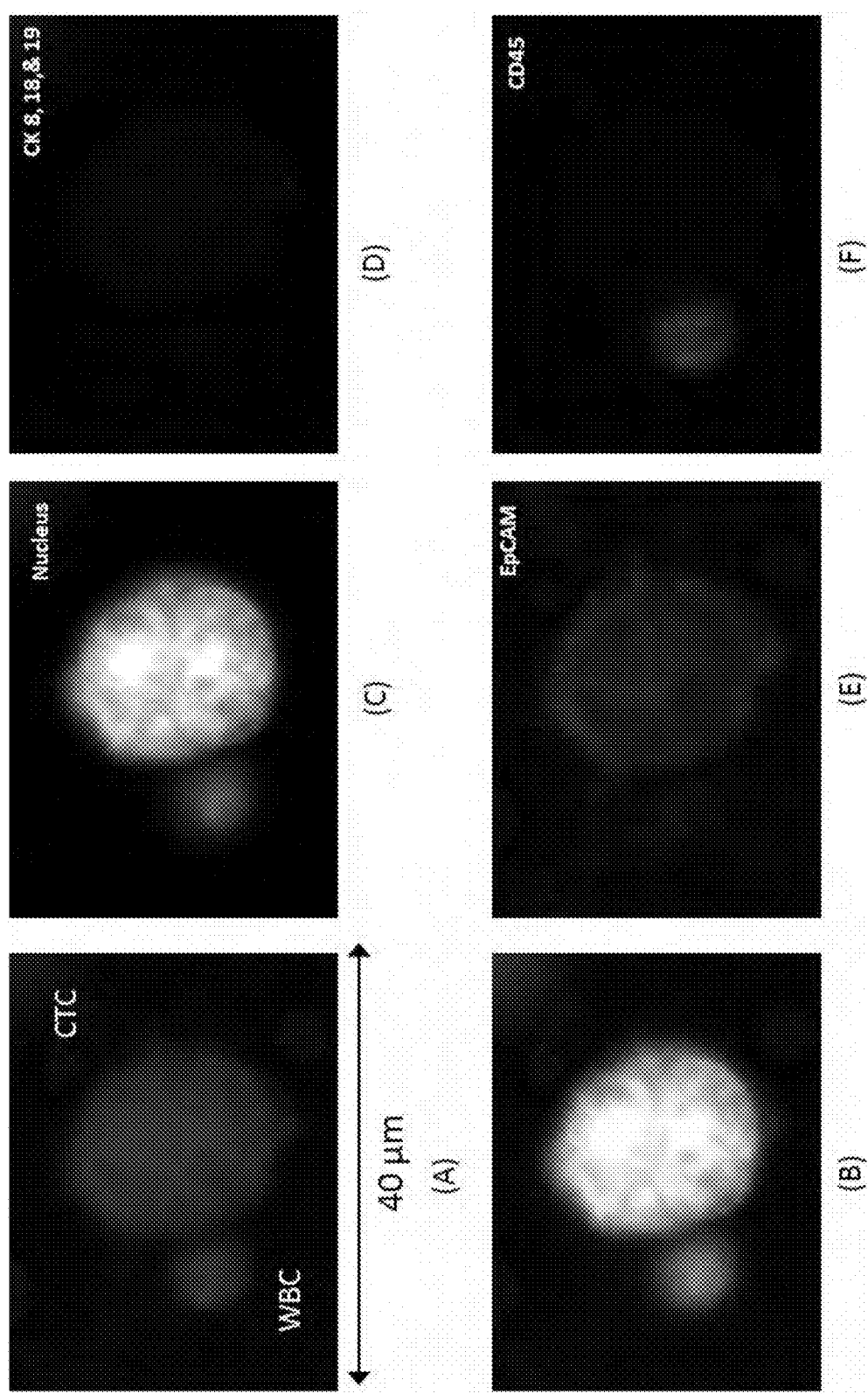
FIGS. 20A-20F show a WBC bound to a CTC from a bladder cancer patient.
Figures 21A, 21B, 21C, 21D, 21E, 21F:
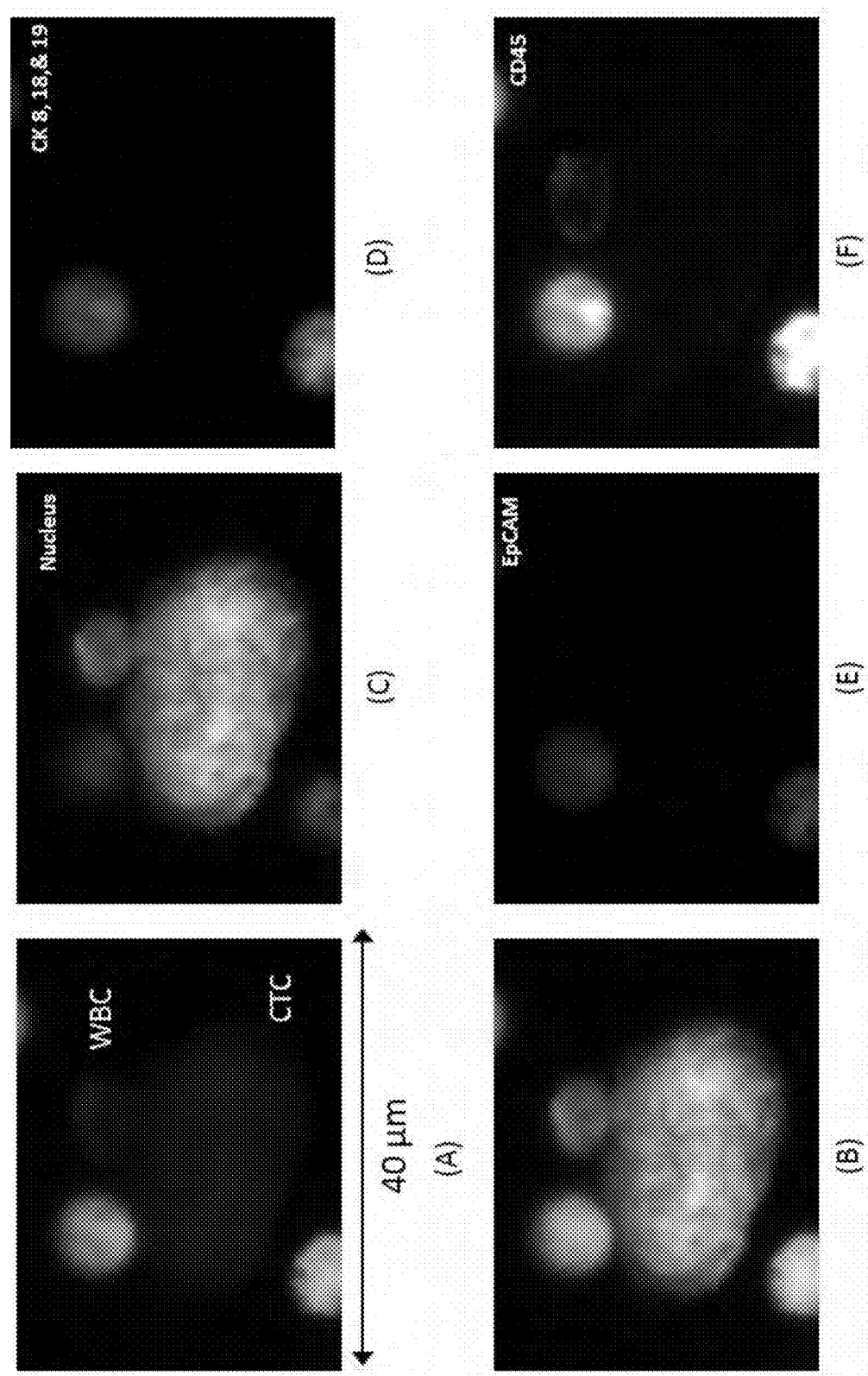
FIGS. 21A-21F show a WBC bound to a CTC from a bladder cancer patient.
Figures 22A, 22B, 22C, 22D, 22E, 22F:
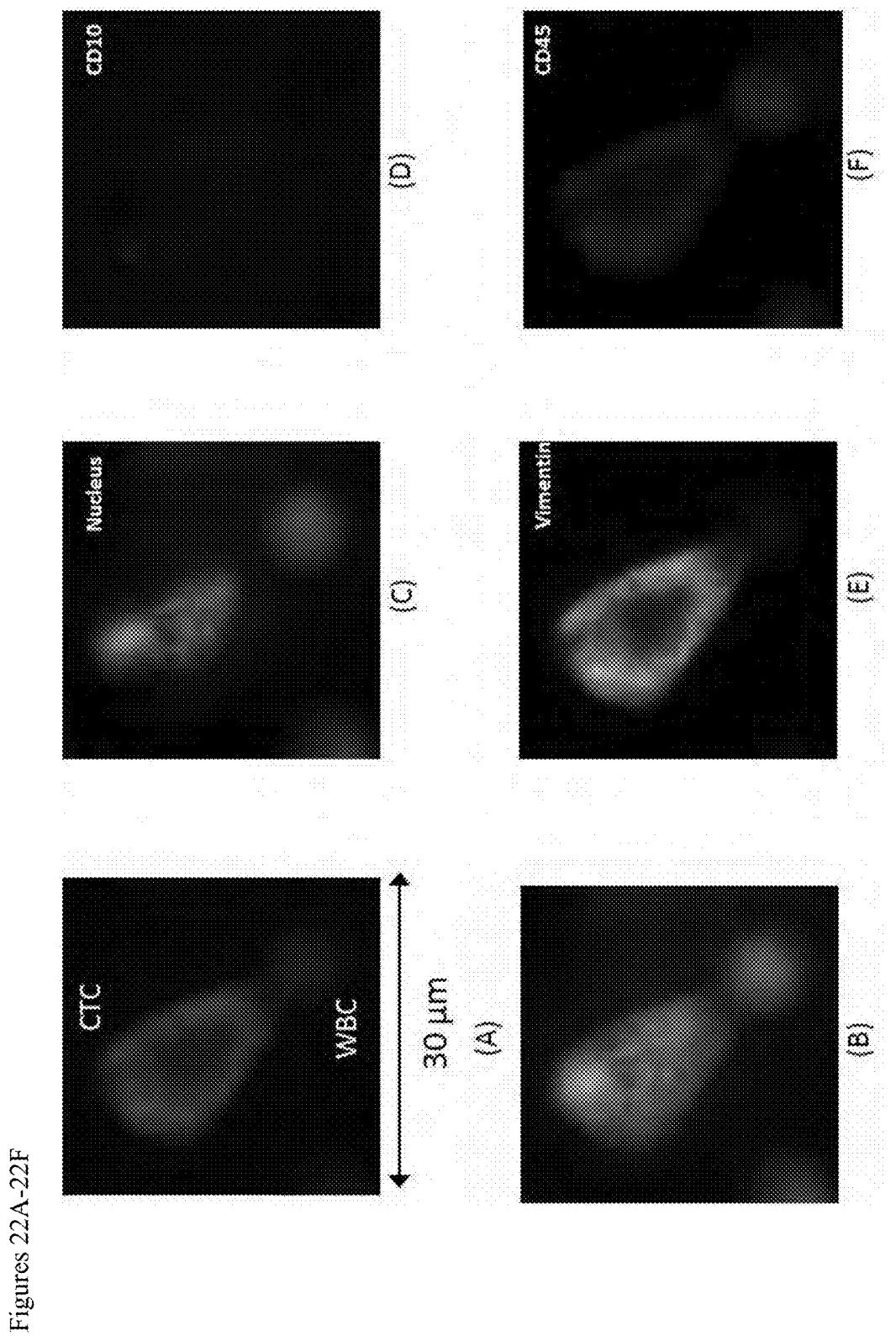
FIGS. 22A-22F show a WBC bound to a CTC from a kidney cancer patient.
Figures 23A, 23B, 23C, 23D, 23E, 23F:
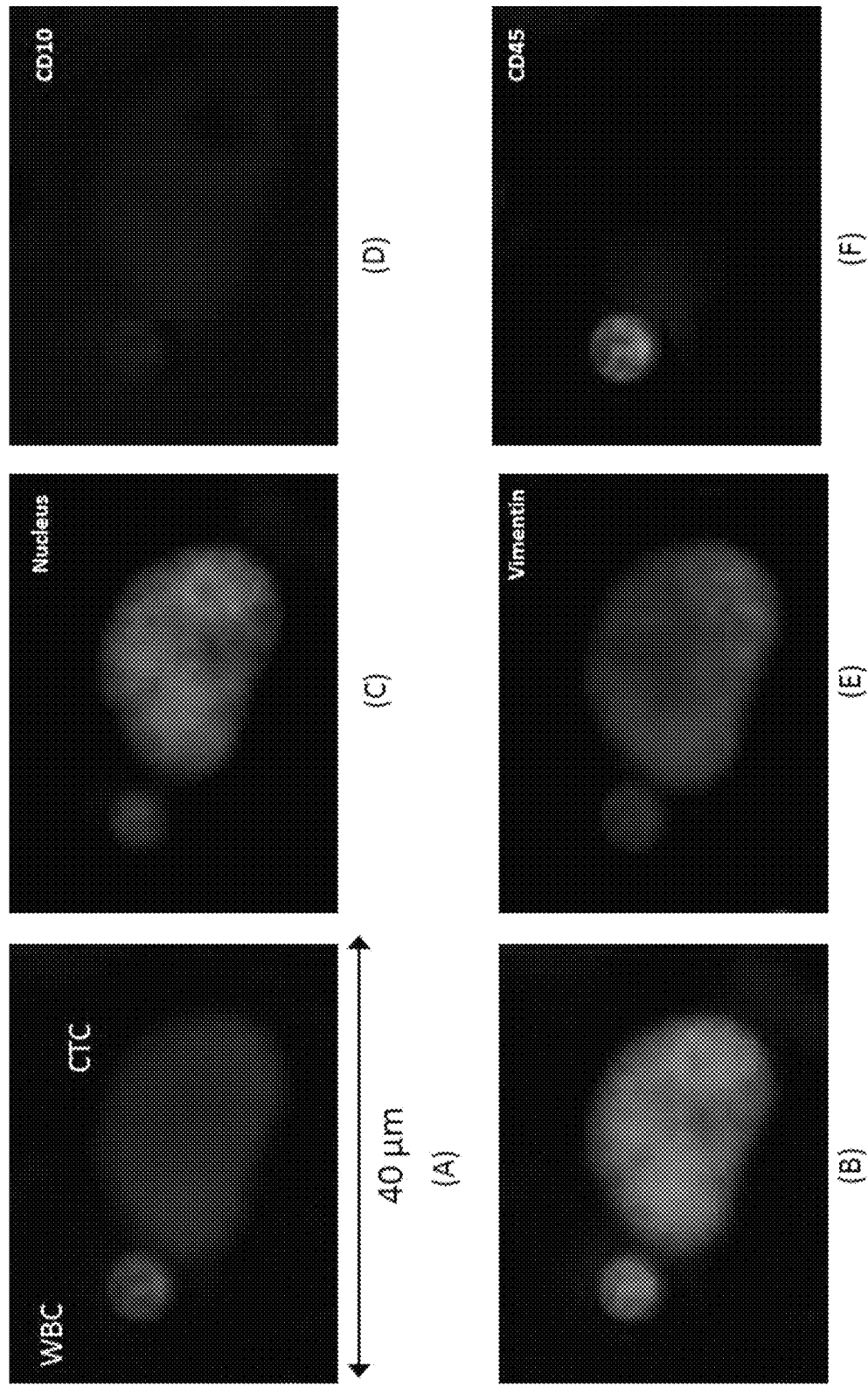
FIGS. 23A-23F show a WBC bound to a CTC from a kidney cancer patient.
Figures 24A, 24B, 24C, 24D, 24E, 24F:
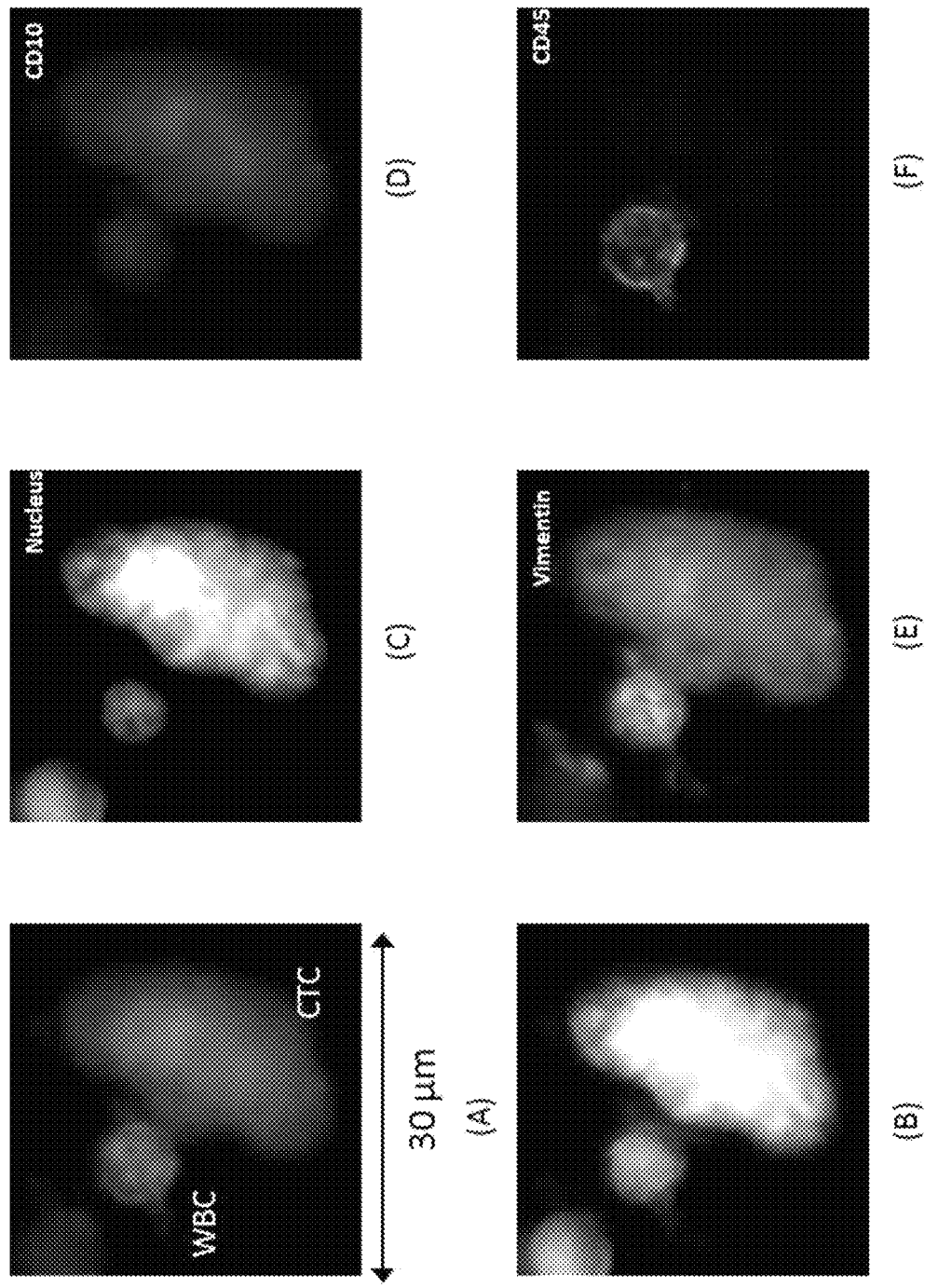
FIGS. 24A-24F show a WBC bound to a CTC from a kidney cancer patient.
Figures 25A, 25B, 25C, 25D, 25E, 25F:
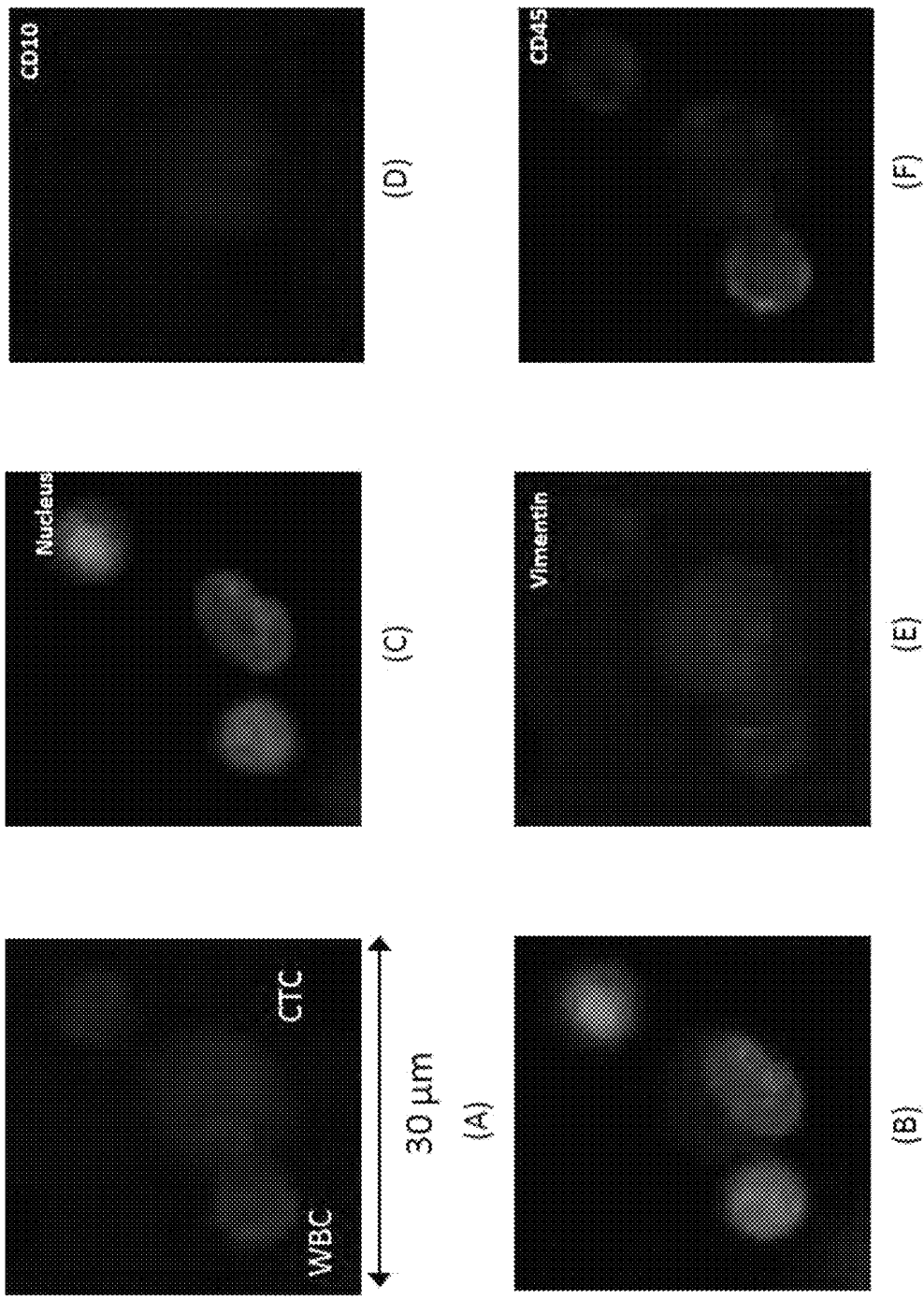
FIGS. 25A-25F show a WBC bound to a CTC from a kidney cancer patient.
Figures 26A, 26B, 26C, 26D, 26E, 26F:
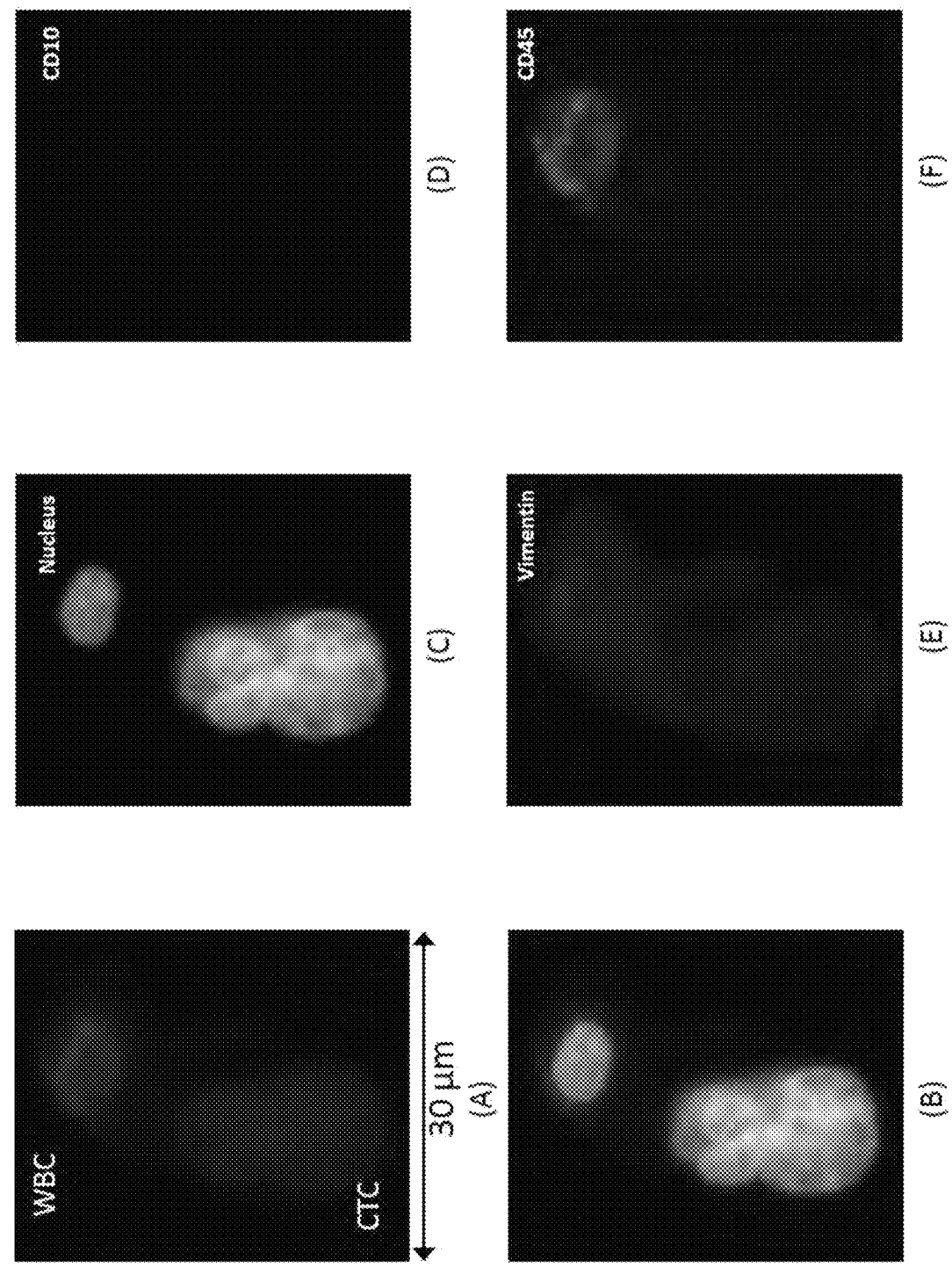
FIGS. 26A-26F show a WBC bound to a CTC from a kidney cancer patient.
Figures 27A, 27B, 27C, 27D, 27E, 27F:
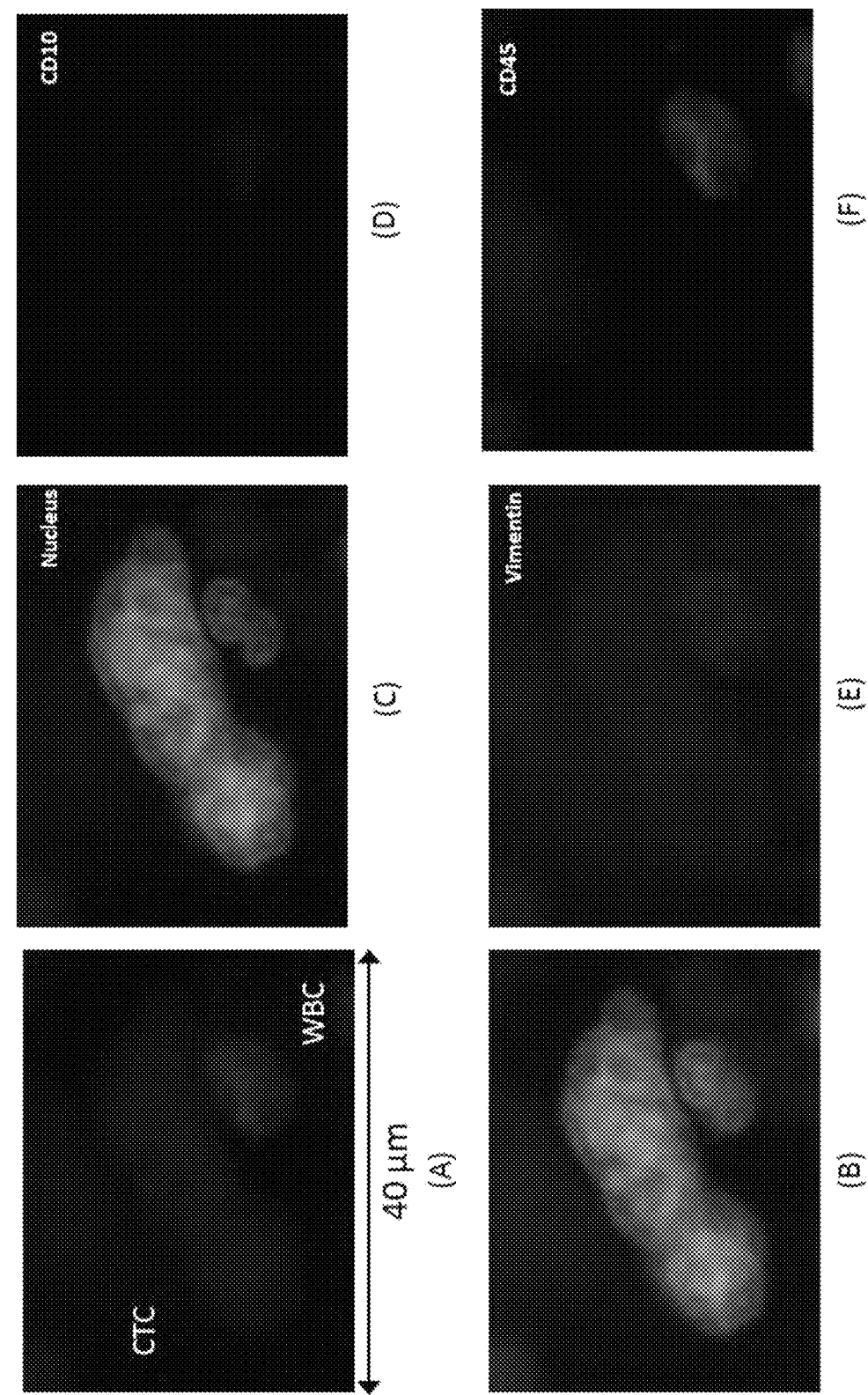
FIGS. 27A-27F show a WBC bound to a CTC from a kidney cancer patient.
Figures 28A, 28B, 28C, 28D, 28E, 28F:
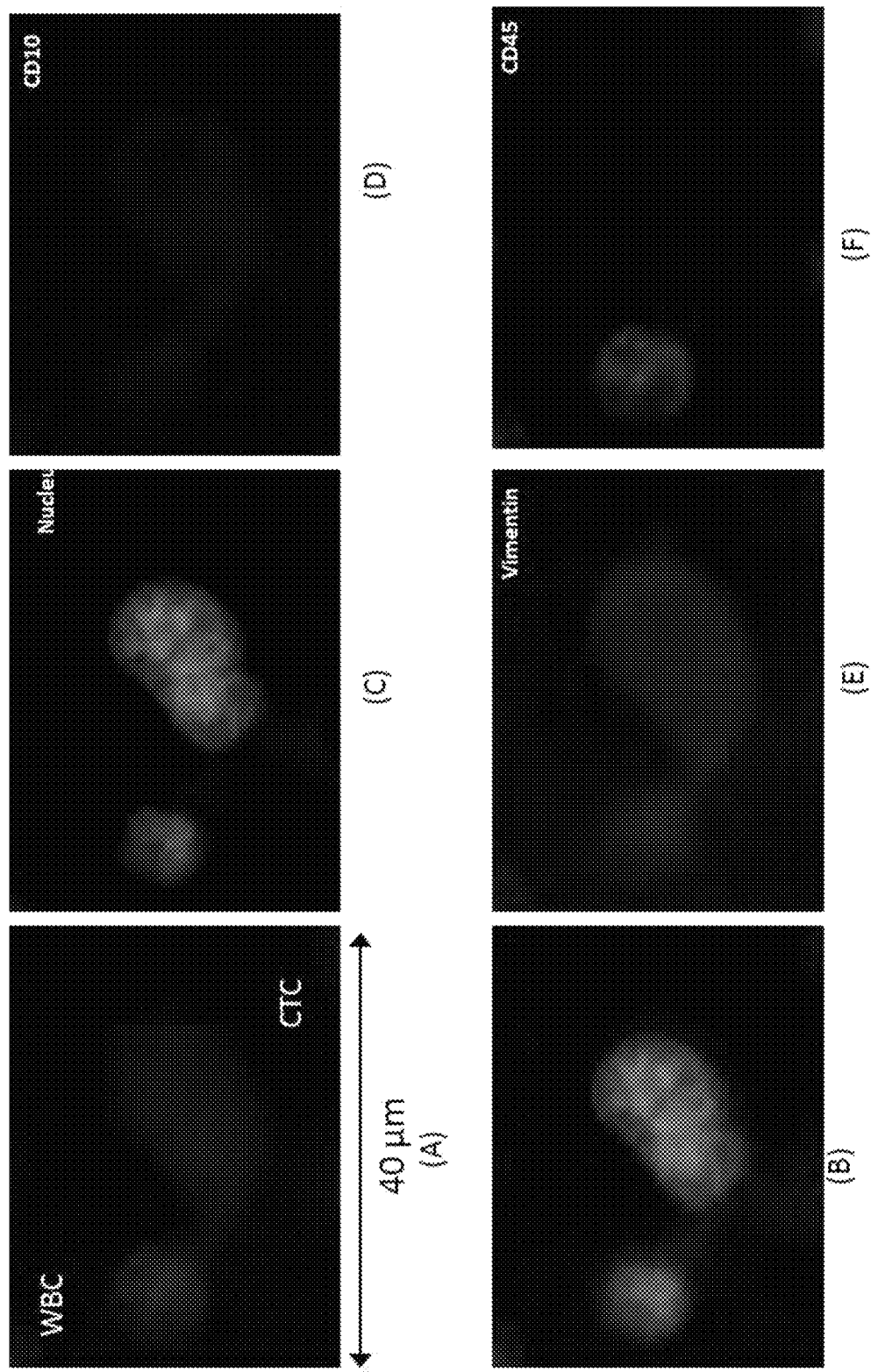
FIGS. 28A-28F show a WBC bound to a CTC from a kidney cancer patient.

FIGS. 19-21 shows WBCs bond to CTCs found in the blood of bladder cancer patients. The markers used for the bladder cancer patients are DAPI, CK 8, 18 & 19, EpCAM and CD45. In FIG. 19E, EpCAM is degraded to spots. The cytoplasm of the WBC (marked in FIG. 19A) and the CTC are in the process of merging with EpCAM around the WBC. The WBC still expresses CD45. FIGS. 20A-20F show a still relatively intact CTC bound to a WBC. FIGS. 21A-21F show a naked CTC nucleus without cytoplasm and the WBC (marked in FIG. 21A) still expressing CD45, but much weaker than WBCs not bound to the CTC (not marked in FIG. 21A).

FIGS. 22-28 show WBCs bond to a CTC found in the blood of kidney cancer patients. The markers used for these patient samples are DAPI, CD10, vimentin and CD45. FIGS. 22A-22F show a CTC from mesenchymal kidney cancer with high expression of vimentin. It is tightly bound to the WBC. FIGS. 23-28 show WBCs bond to a CTC found in blood of non-mesenchymal kidney cancer patients expressing lower level of vimentin than shown in FIG. 22. The nuclei and the cytoplasm of the WBCs and CTCs are pulled toward each other. CD10, vimentin and CD45 markers all become very weak after WBCs bond to the CTCs. The amount of the cytoplasm decreases and eventually can all be lost.

Frequency of CTCs and CAMLs in Blood of Cancer Patients

Figure 29:
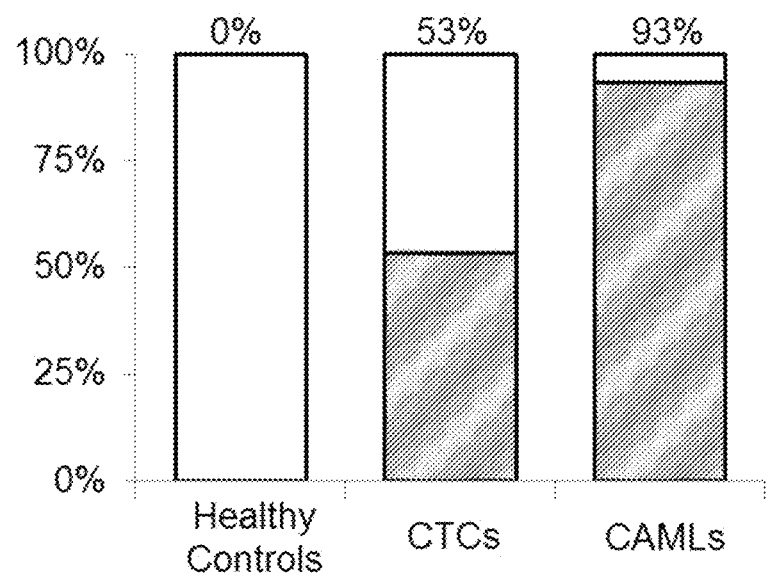
FIG. 29 shows the frequency of CTC and CAMLs in 105 breast, prostate, pancreatic, and lung cancer patients and 30 health controls.
Figure 30:
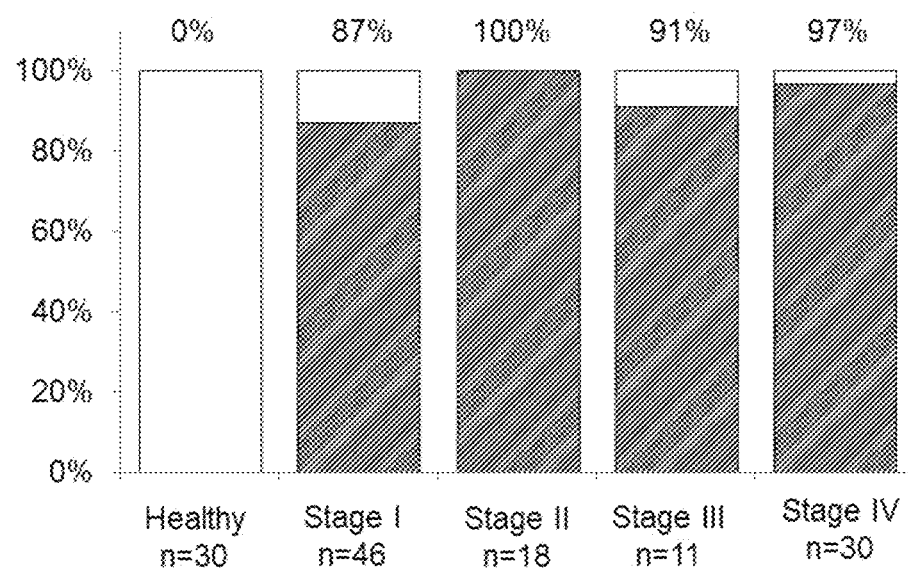
FIG. 30 shows the frequency of CAMLs in different stages of cancer from 105 breast, prostate, pancreatic and lung cancer patients.

PDCTCs are rarely found in early stages of cancer. Even though PDCTCs are found more frequently in stage III and IV breast and prostate cancer patients, they can be seen at low frequencies in most other solid tumors. As an example, 105 cancer patients (breast (n=34), prostate (n=25), pancreatic (n=39) and lung (n=7)) and 30 health controls were analyzed. FIG. 29 shows PDCTCs and CAMLs could not be found in the blood of healthy controls. In contrast, CAMLs were found in 98 out of 105 cancer patients. The percentage of the patients with PDCTCs and CAMLs are 53% and 93%, respectively. The stage of cancer for the 105 cancer patients were as follows: stage I (n=46), stage II (n=18), stage III (n=11), and stage IV (n=30). FIG. 30 shows that the percentage of the patients having CAMLs in stages I, II, III and IV are 87%, 100%, 91% and 97%, respectively. CAMLs were found to be more common than PDCTCs. Patient samples from 12 different solid tumors were analyzed: breast, prostate, pancreatic, lung, colorectal, uterine, neuroblastoma, esophageal, kidney, bladder, sarcoma, and ovarian. CAMLs were found in all those types of cancer (data not shown).

Number of CAMLs Vary Based on Therapy

Figure 31:
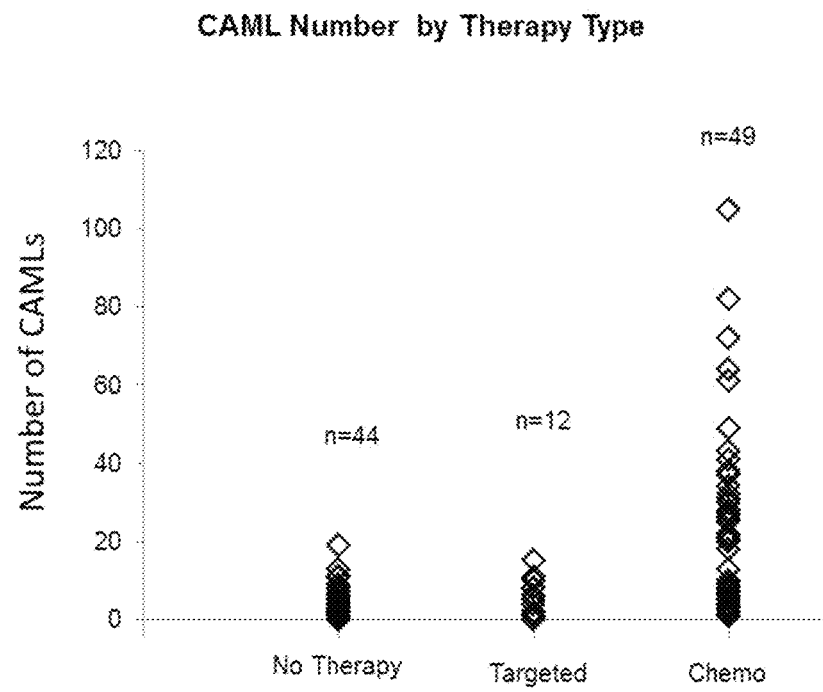
FIG. 31 shows the number of CAMLs following treatment.

Of the 105 patients noted above, 44 patients received no therapy, 12 received target therapy and 49 received chemotherapy. Follow up screening was performed to detect CAMLs in the patients after the completion of therapy. The number of CAMLs appears to depend on therapy type, as shown in FIG. 31. The number of CAMLs in patients receiving chemotherapy is much more than the number of CAMLs in patients receiving no therapy or targeted therapy.

Relationship of Number of CAMLs to Staging and Disease Progression

Figure 32:
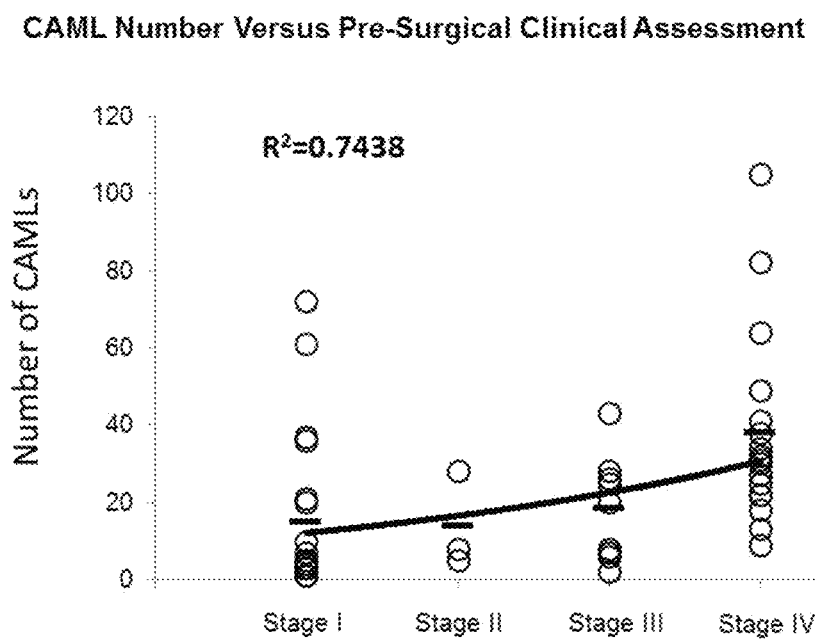
FIG. 32 shows the number of CAMLs pre-surgical clinical assessment.
Figure 33A:
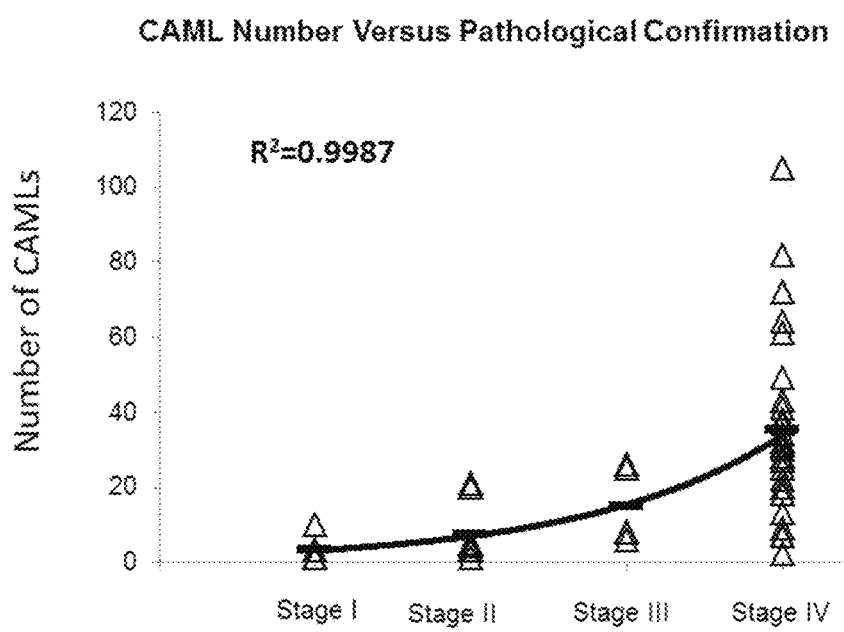
FIGS. 33A-33B shows the number of CAMLs based on pathological evaluation with FIG. 33A showing the number for pathological confirmation and FIG. 33B showing the cell size variation for the four different stages of cancer.

The number of CAMLs in patients undergoing chemotherapy is only weakly associated with cancer stage at the time of pre-treatment clinical assessment, FIG. 32, and is highly correlative with stage after pathological confirmation, FIG. 33A. For patients undergoing chemotherapy, the number of CAMLs were exponentially correlated with final pathological confirmation: stage I (3.2), Stage II (7.1), Stage III (14.6), Stage IV (35.1); $R^2=0.99$.

Figure 33B:
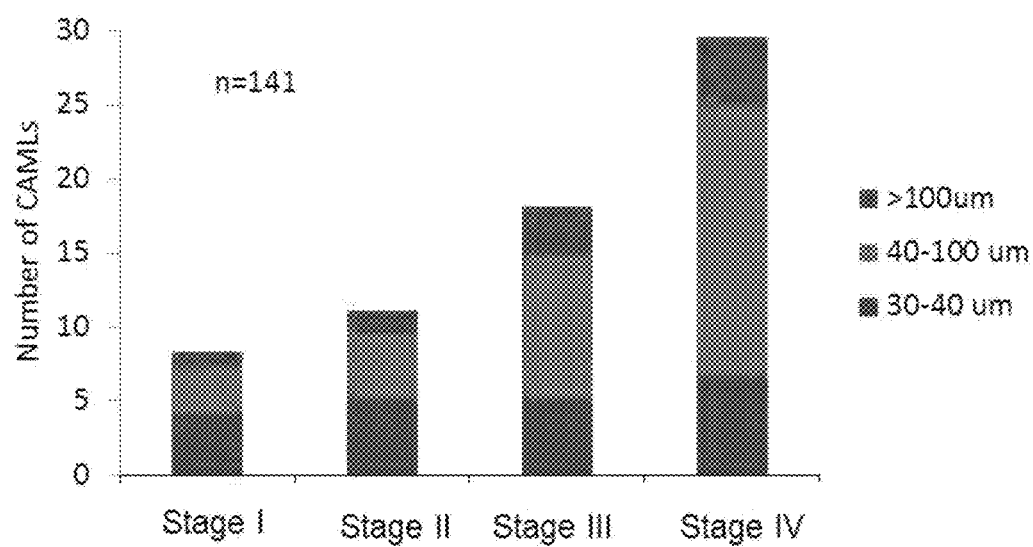

FIG. 33B breaks down the number of CAMLs based on size for different stages. CAMLs in later stages have more CAMLs with larger sizes.

Breast Cancer Screening

Because CAMLs can be found in high percentages in all stages of solid tumors, CAMLs as a cancer screening marker was evaluated for breast cancer. A double-blind prospective study was conducted of 41 subjects where mammography was judged abnormal. A double blinded test was performed: (i) 7.5 mL of peripheral blood samples were taken to test for CAMLs and (ii) tissue diagnosis by core needle biopsy was performed. Though mammography could not distinguish the subpopulations in this group, CAML presence did differentiate between benign and malignant breast disease with a sensitivity of 90% and a specificity of 72% (data not shown).

Antibody Staining and Re-Staining of Isolated Cells

Figure 34:
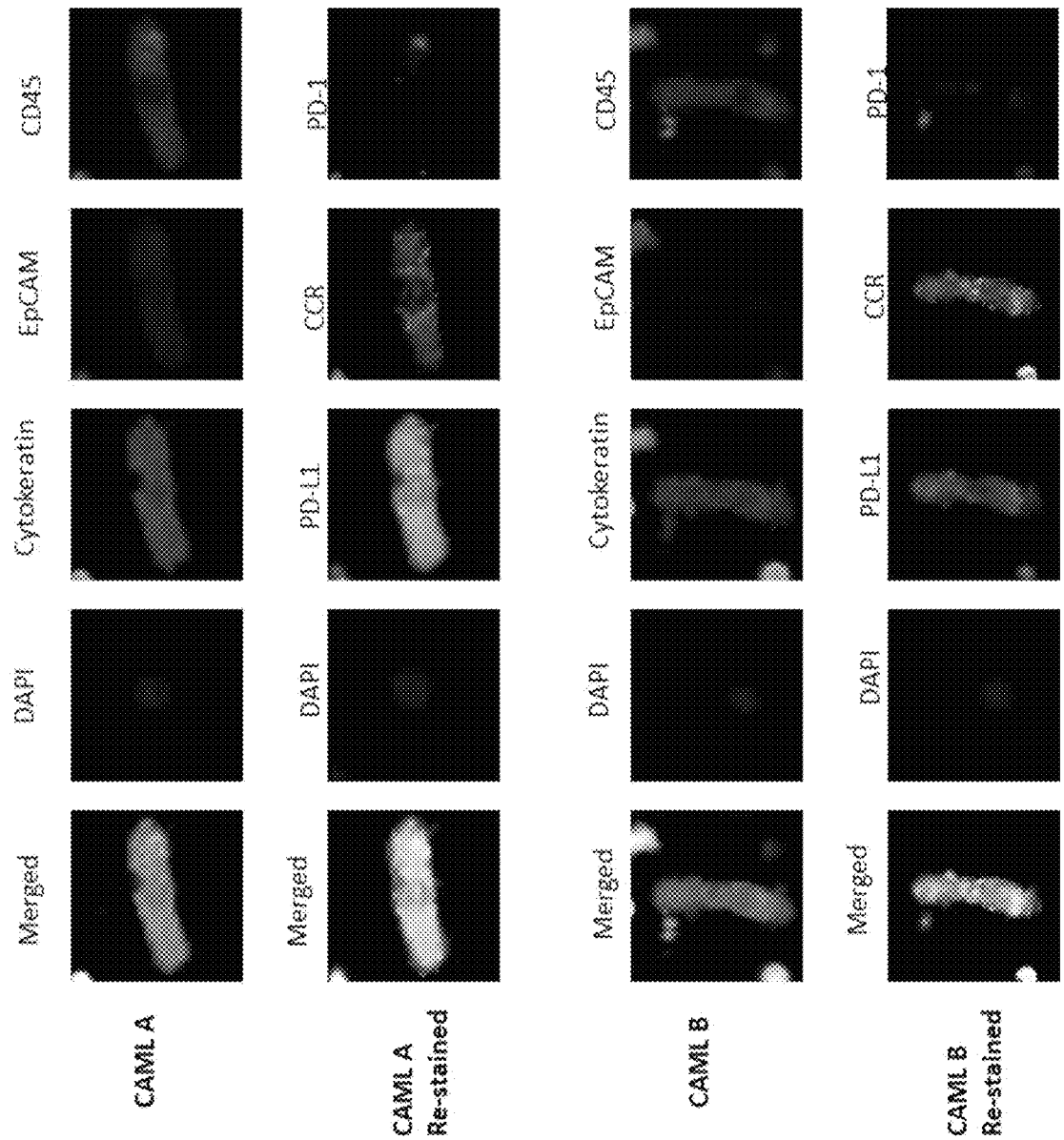
FIG. 34 shows the re-staining of CAMLs.

Typical fluorescent microscopes usually use four or five fluorescent channels to minimize bleed through of fluorescent emissions into unintended fluorescent channels. One channel is taken by DAPI for imaging the nucleus. Often there is a need to evaluate more than three markers. Given these shortcomings, a method that allows analysis of up to approximately 12 different markers on the same cell was developed that can be used in conjunction with each of the methods disclosed in the present disclosure. After the process of filtration and staining the cells on the filter with a first set of markers, the cells of interest are identified and imaged. To evaluate more markers on the same cells, a quenching/stripping step was developed followed by a re-staining technique. This required the cell to stay at the same location to allow reimaging of the same cell. This can be repeated a number of times. Top row of FIG. 34 shows a CAML A with standard CTC stains: DAPI, CK 8, 18, 19, EpCAM and CD45. The second row shows the re-staining of the same cells after quenching and re-stained for markers of interest: PD-L1, CCR and PD-1. Third row of FIG. 34 shows a CAML B with standard CTC stains. The fourth row shows the re-staining of the same CAML B after quenching for markers of interest: PD-L1, CCR and PD-1. This re-staining method is particularly suitable for cells fixed on the microfilter. Their location is fixed so they can be reimaged to evaluate different markers. CTCs and other cells on the filter can also be re-stained using this technique. This re-staining method is very useful for analyzing the cancer type, companion diagnostic, therapy response, cancer screening, and a variety of research applications.

Single Cell Molecular Assays Using CAMLs and CTCs

Molecular analysis of CAMLs and CTCs can potentially be used to determine cancer subtyping for gene mutations, translocations and amplifications, by various PCR assays, microarrays, FISH assays and sequencing. Single cell molecular analysis is becoming common, and single cell analysis of CAMLs are particularly interesting. Some assays require more than one nucleus and/or cell to reduce errors. The present invention thus includes methods of molecular analysis of a single CAML cell where a single CAML cell is obtained and molecular analysis is conducted on the single cell. There is no limitation on the particular type of molecular analysis that may be conducted on the single cell and such means include, but are not limited to, nucleic acid sequencing, northern blot analysis and southern blot analysis.

A method to collect CTCs and CAMLs using the microfiltration device is described. For this application, it is desired that the cells be easily removed from the filter, the opposite of the need for cells to stay on the filter for re-staining purposes. The important step to allow removal of the cells is to coat the filter to prevent the cells from sticking, for example coating using fetal bovine serum (FBS) or bovine serum albumin (BSA). Other coatings to prevent cell adhesion are also applicable. The sample flows through the filter to collect cells larger than the pores. There are two methods to collect the cells of interest. Method 1: remove the filter from the filter holder and place in a dish or glass slide with cells on top, and cover with appropriate liquid, such as PBS; cells can be directly picking cells off the filter using micromanipulators. Method 2: attach a syringe filled with PBS to the bottom of the holder with the cells on the filter and backwash the cells off the filter. The cells may be concentrated by centrifugation and removing the supernatant. The cells need to be stained to enable visualization under the microscope. One non-limiting choice of stains is fluorescent intercalating dyes. Another example is to stain for cell surface markers such as EpCAM, CD45, and/or other markers. There are various ways to pick out cells of interest from the dish such as micromanipulators, or instruments such as CellColector, and other instruments.

Companion Diagnostics

CAMLs can be used as a source of tissue for companion diagnostics to determine the specific drug to be prescribed to the patient. Currently companion diagnostics utilize tissue biopsies to stain for markers for drug targets, perform FISH assays, and conduct other molecular assays to look for gene mutations, amplification or translocations by PCR, microarrays, sequencing, etc. Examples of conventional companion diagnostics utilizing tissue biopsies are FISH for HER2 amplification, FISH for ALK translocation, PD-L1 in tissue, AR and ER in tissue, etc. Sometime there is not enough tissue, or no tissue at all to evaluate a wide variety of drugs. CTCs and CAMLs can be harvested repeatedly and used in place of the tissue biopsies. Also the same sample can be re-stained repeatedly to evaluate the efficacy of multiple drugs.

Monitor Treatment Response

Liquid Cell Biopsy provides a minimally invasive method to monitor treatment response in a patient. The following approaches can be adopted to monitor efficacy of a cancer treatment, comprising:

(a) monitor the change of the number of CAMLs and CTCs from the same subject at different time points after treatments;

(b) monitor the changes of sizes of CAMLs and CTCs at the different time points;

(c) monitor the changes of intensity of markers in the CAMLs and CTCs at the different time points; and (d) monitor the change of the location of the markers, cytoplasm versus nucleus, in the CAMLs and CTCs at the different time points.

As one example related to chemotherapy, FIG. 31 shows that chemotherapy responders seem to exhibit an increase in CAMLs shortly after chemotherapy treatment. In contrast, the number of CAMLs from target therapy did not show an increase above the no treatment control.

Figure 35:
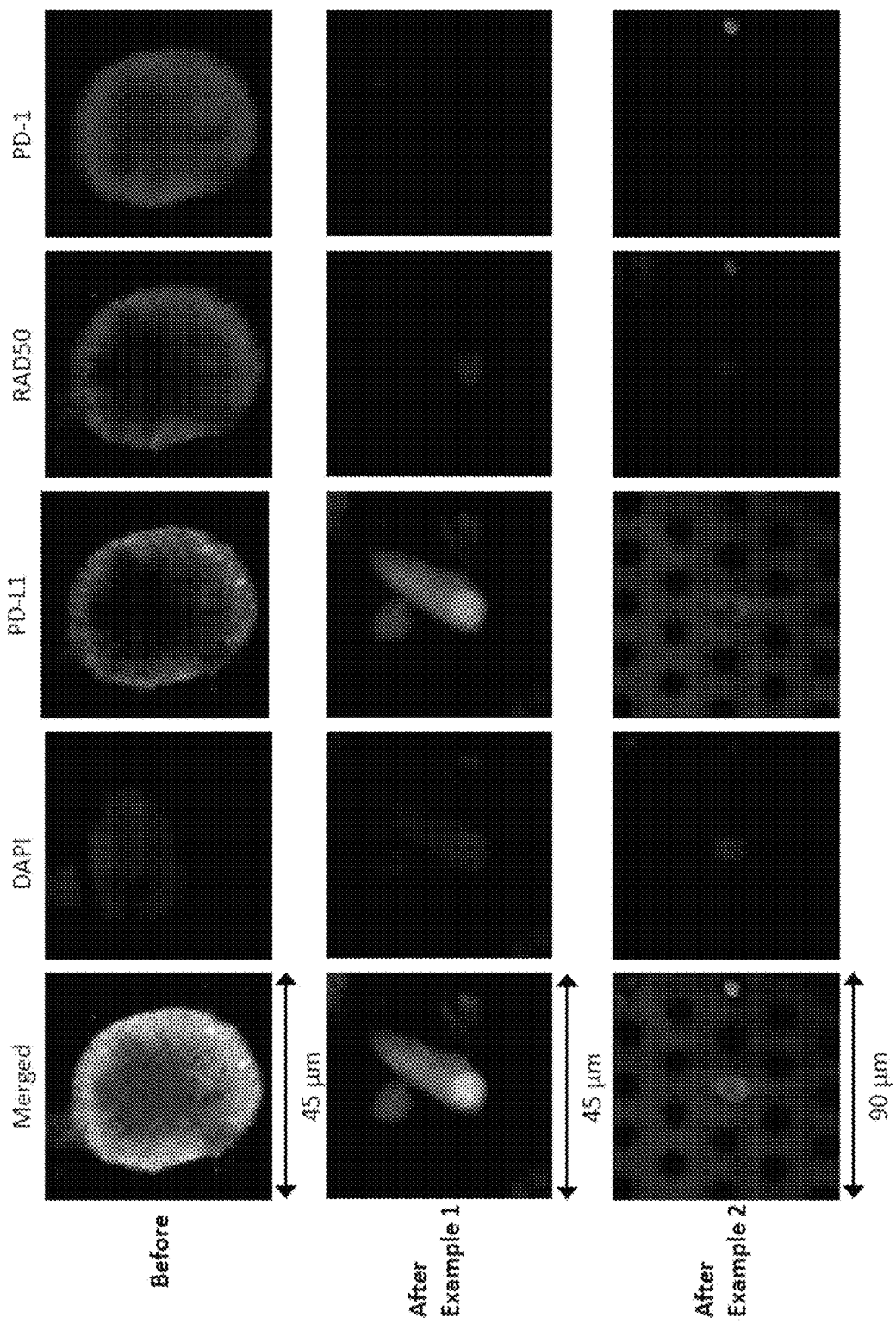
FIG. 35 shows the effect of radiation therapy on cancer marker RAD50 on a CAML.

In a second example radiation therapy, the top row of FIG. 35 show a CAML from a lung cancer patient before radiation therapy stained for DAPI, PD-L1, RAD50 and PD-1. The bottom two rows show two different CAMLs after radiation therapy also stained for DAPI, PD-L1, RAD50 and PD-1. RAD50 migrating to the site of DNA damage in the nucleus.

Figure 36:
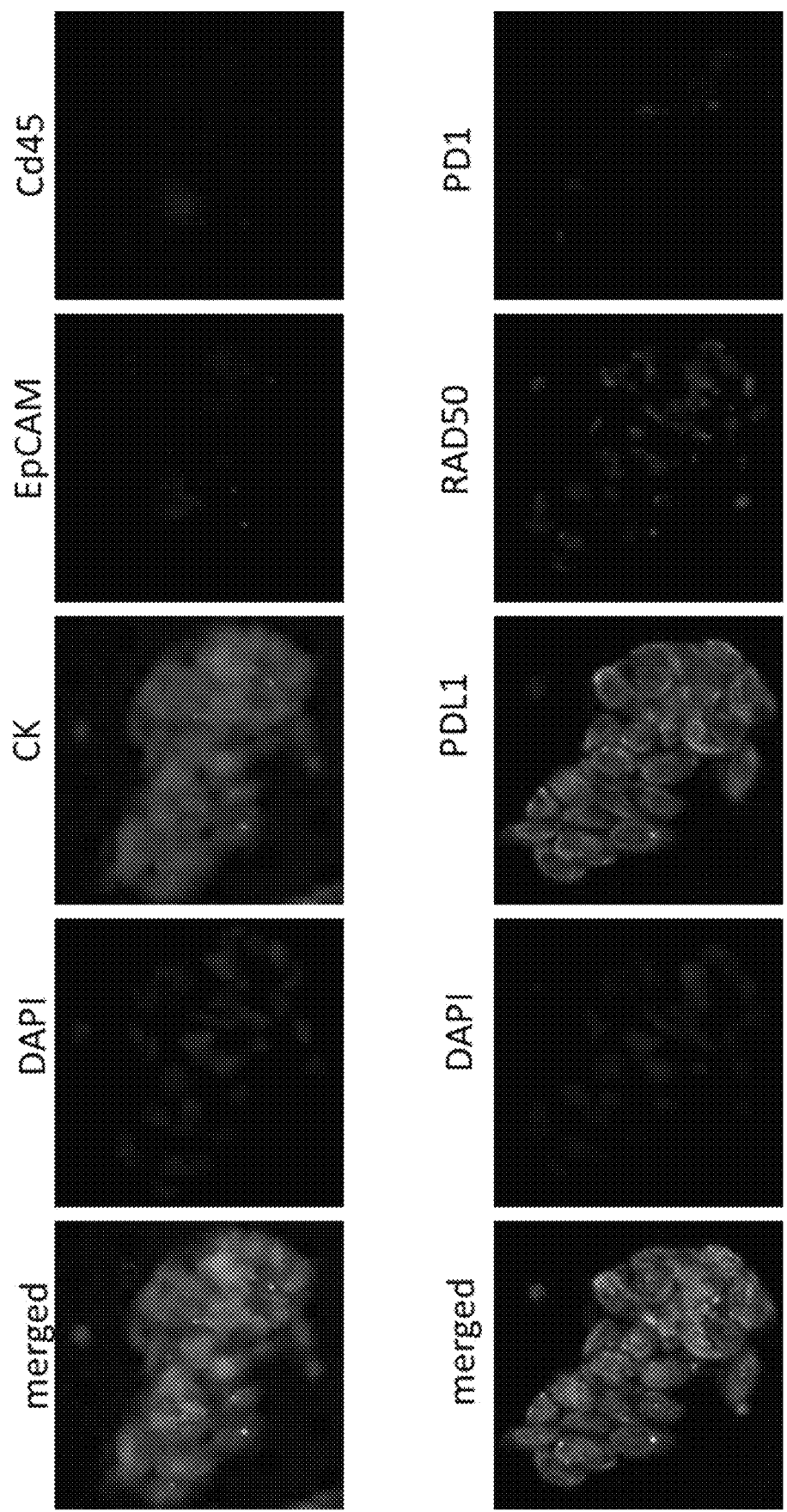
FIG. 36 shows the effect of radiation therapy on cancer maker RAD50, and PD-L1 on CTCs.

This change in RAD50 is also seen in CTCs. A third example combines re-staining to examine effectiveness of radiation therapy. The top row of FIG. 36 shows a cluster of CTCs from a lung cancer patient after treatment with radiation using the standard CTC stains: DAPI, CK 8, 18, 19, EpCAM and CD45. The bottom row shows the same CTC cluster after quenching and re-staining for markers related to radiation therapy and immune response: PD-L1, RAD50 and PD-1.

Figure 37:
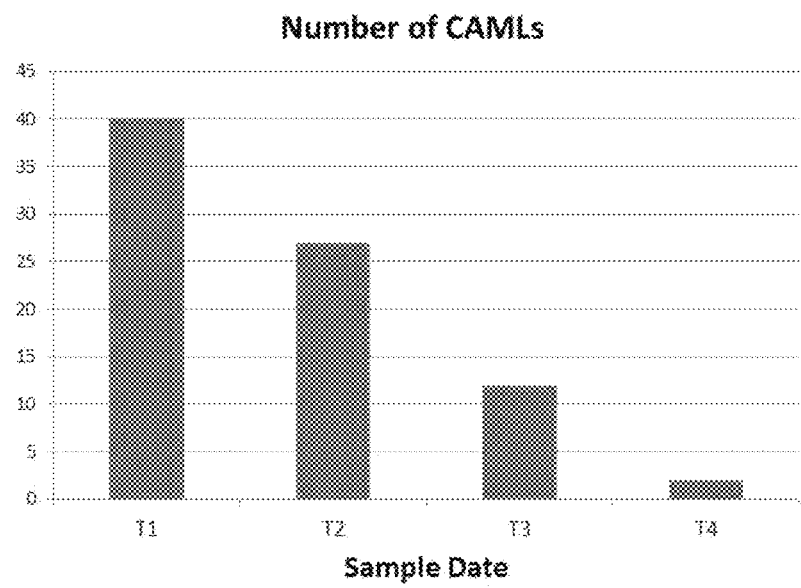
FIG. 37 shows the decrease of number of CAMLs after cancer treatment over time.
Figure 38:
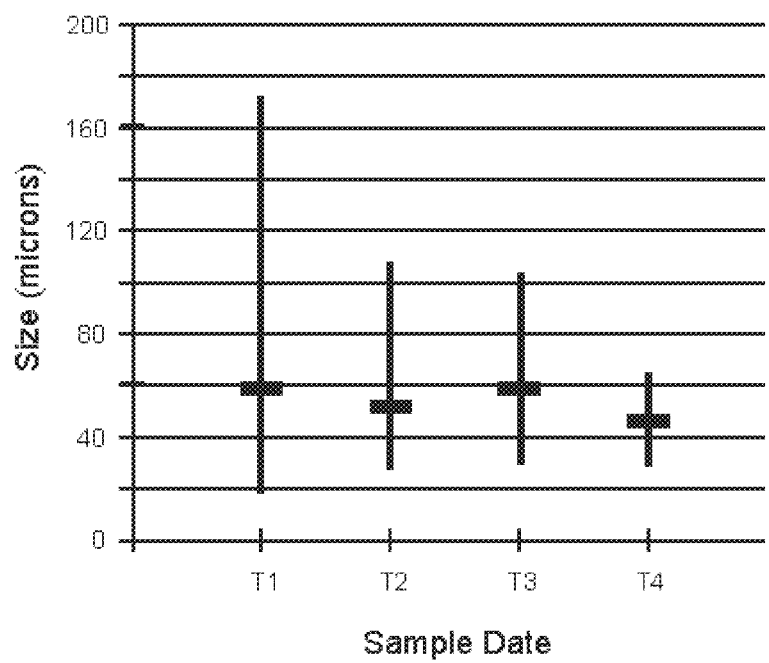
FIG. 38 shows the decrease of size of CAMLs over time.
Figure 39A:
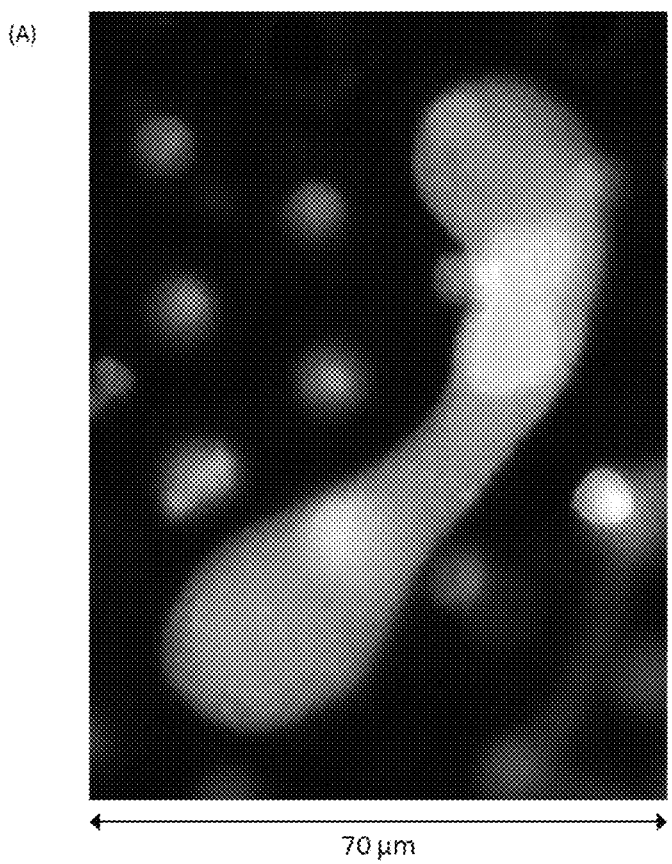
FIGS. 39A-39E show a CAML with strong stain for PD-L1 with Vimentin (max. S-N=880); PDL1 (max. S-N=880); CD45 (max. S-N=850); Length 107 μm.
Figures 39B, 39C, 39D, 39E:
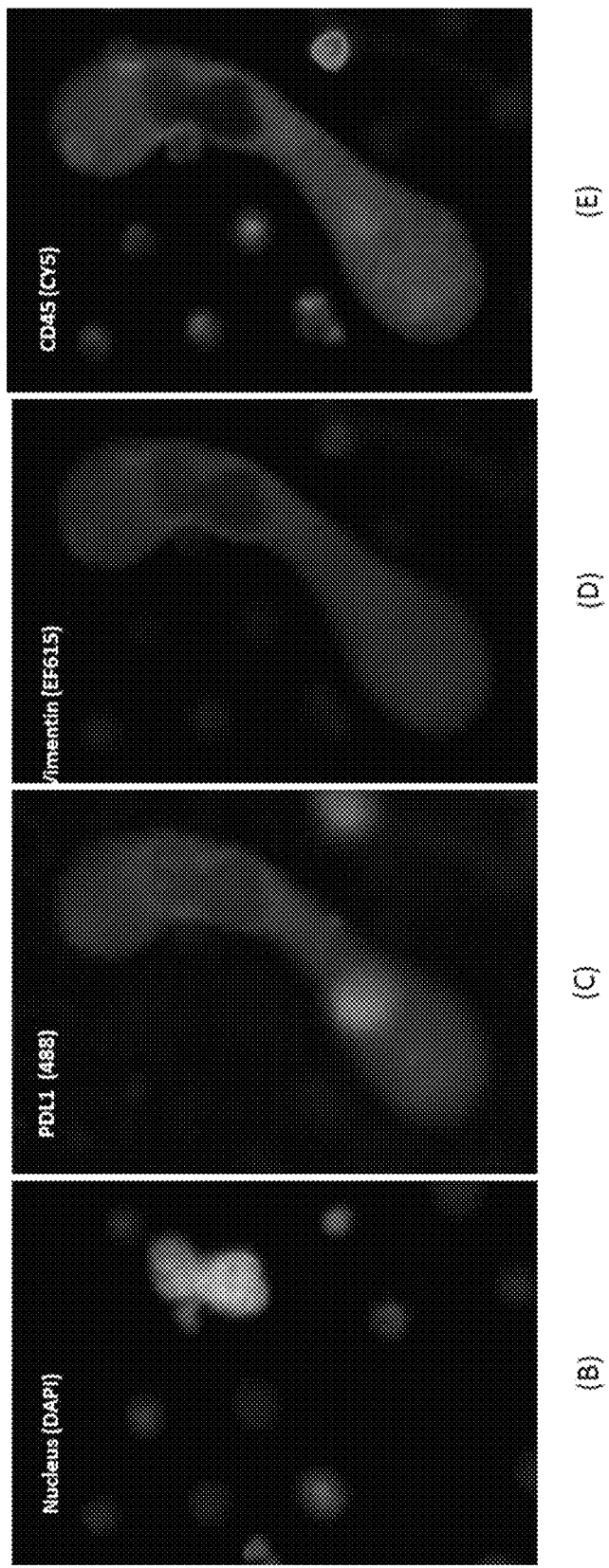
Figure 40A:
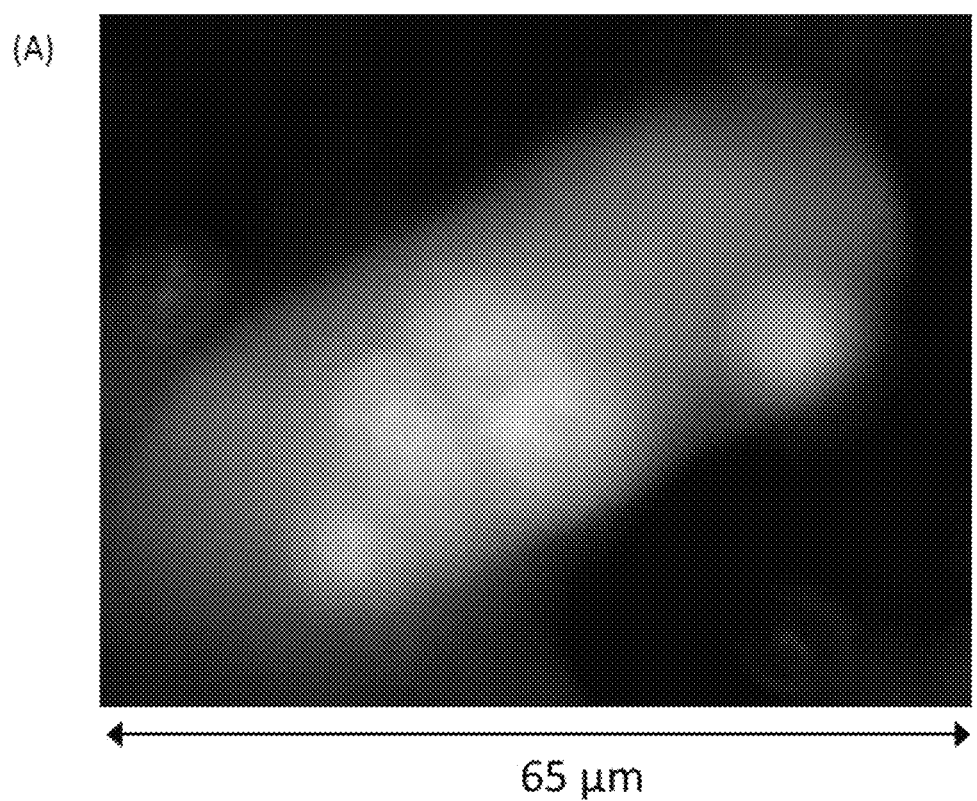
FIGS. 40A-40E show a CAML with weak stain for PD-L1 with Vimentin (max. S-N=500); PDL1 (max. S-N=280); CD45 (max. S-N=820); Lengths 62 μm.
Figures 40B, 40C, 40D, 40E:
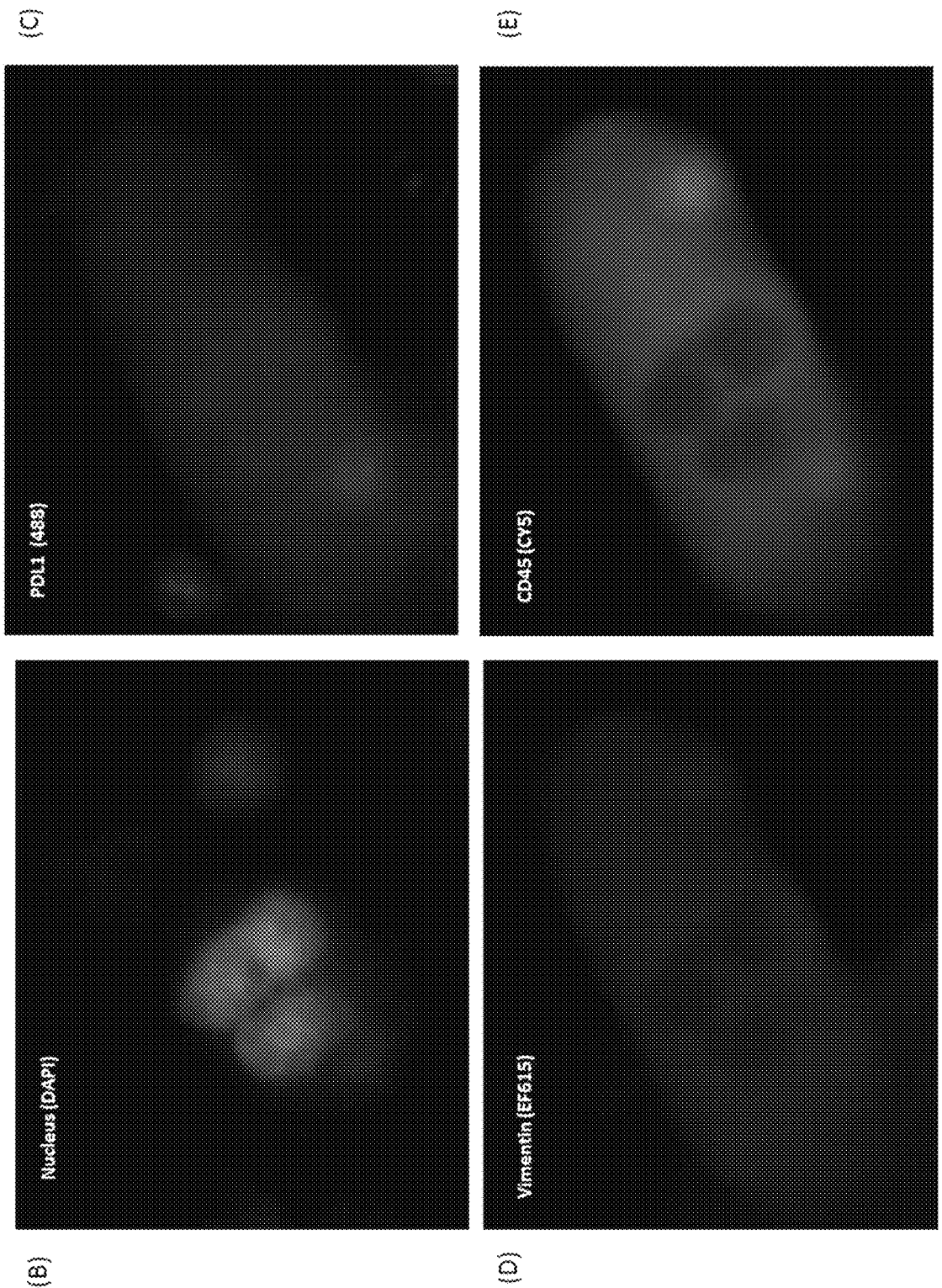
Figure 41A:
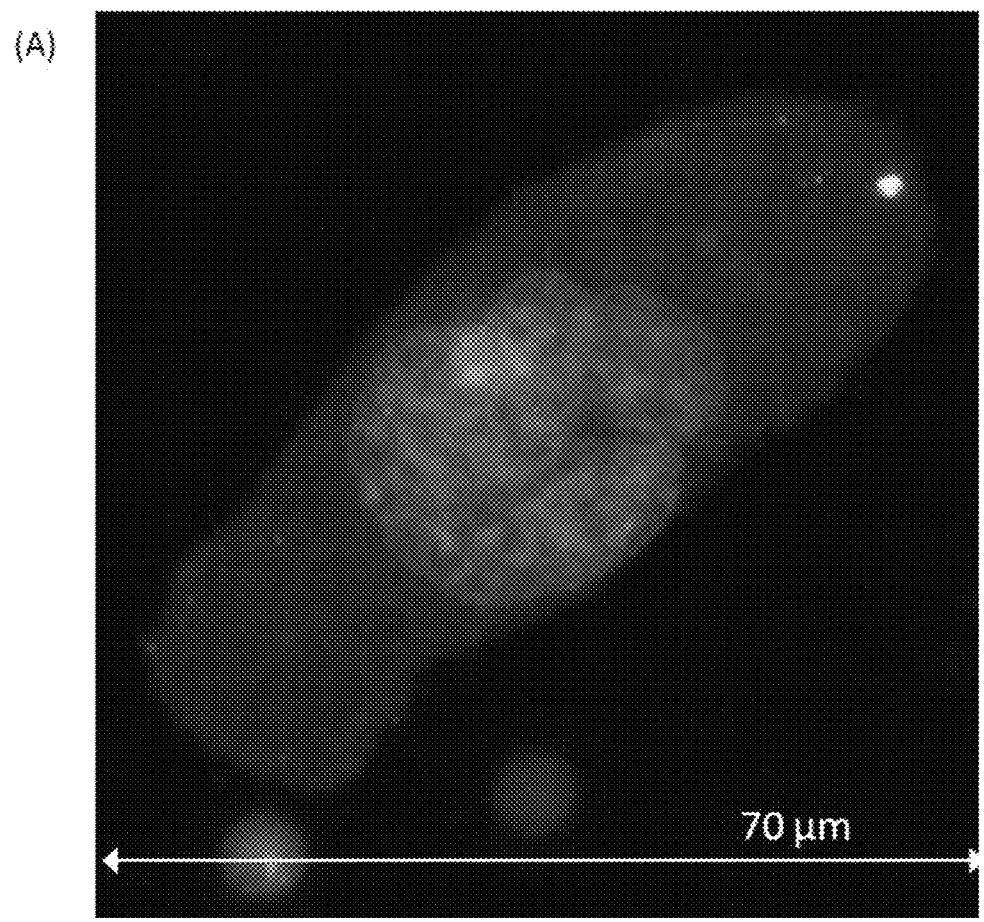
FIGS. 41A-41E show a CAML with very weak stain for PD-L1 with Vimentin (max. S-N=75); PDL1 (max. S-N=100); CD45 weak (max. S-N=145) Bright PDL1 spot is 1000; CD45 is not smooth; Length—74 μm.
Figures 41B, 41C, 41D, 41E:
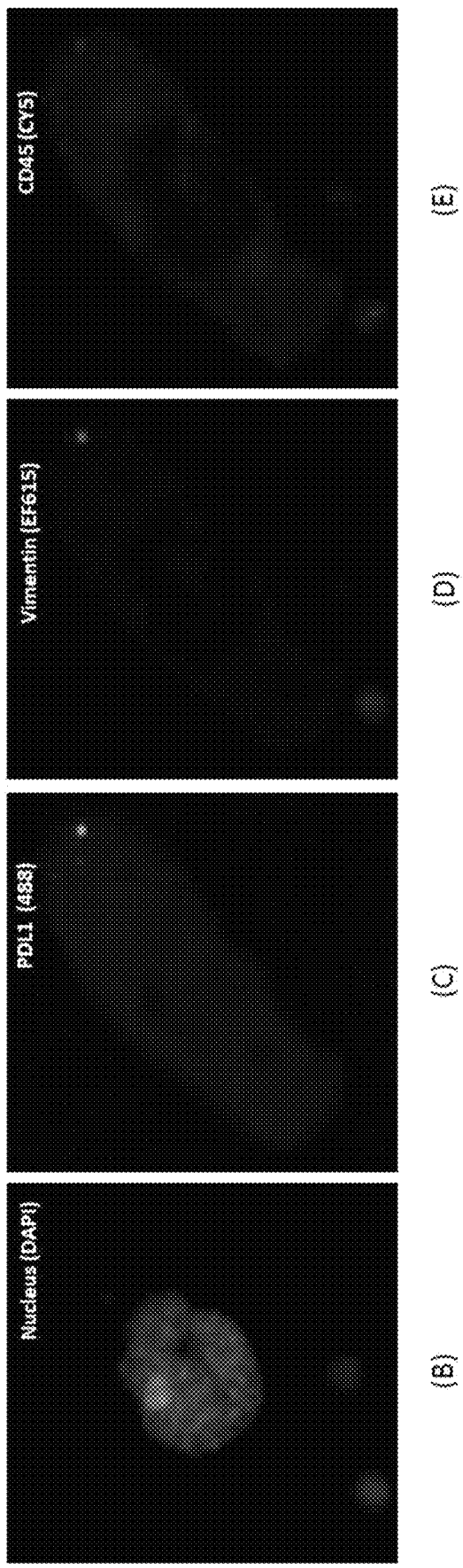
Figures 42A, 42B, 42C, 42D:
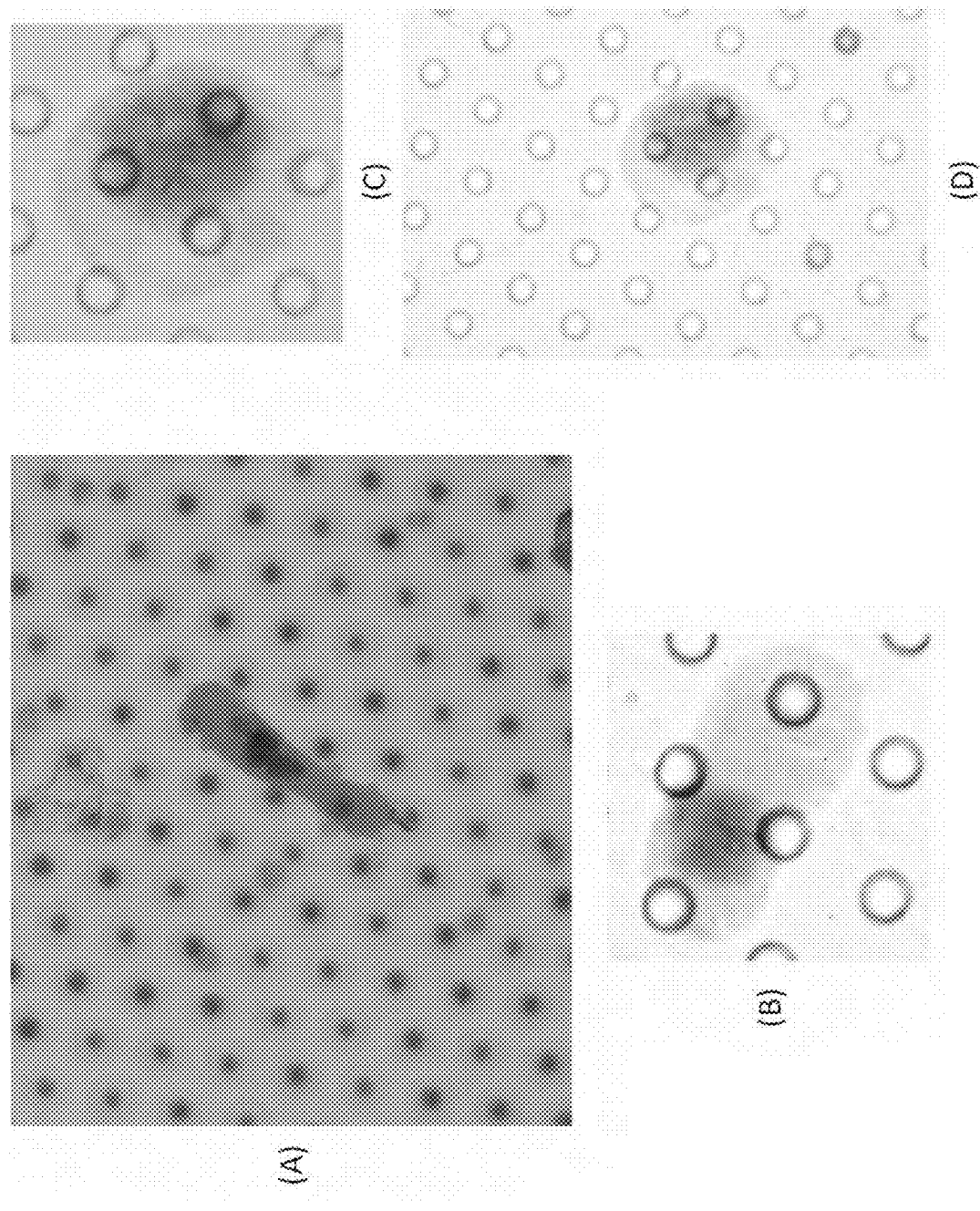
FIGS. 42A-42D show colorimetric staining of CAMLs.

A fourth example is related to immunotherapy. Immunotherapies that enable the body to kill a tumor have shown impressive results for many types of cancers. An example of an immunotherapy drug is an antibody against PD-L1 on the surface of the tumor cells; and another sample of an immunotherapy drug is an antibody against PD-1 on the surface of the killer T-cells. Both types of immunotherapy drug enable killer T-cells to kill the tumor cells for some of the patients. FIG. 37 shows an example of number of CAMLs collected at four time intervals spread approximately by two to three weeks. The treatment of PD-1 was on dates T1 and T3, after providing the blood sample for Liquid Cell Biopsy. The decrease in number of CAMLs after treatment maybe an indication that the patient is not responding to treatment. FIG. 38 shows the corresponding ranges of sizes of the CAMLs as the CAMLs are also decreasing in size. This information suggests that there might be a decrease of tumor debris in the blood as a result of treatment, suggesting that patient may not be responding to treatment. FIG. 39 is a CAML before T1 showing very bright PD-L1. The signal of PD-L1 above background noise is about a factor of 8 of the background noise. FIG. 40 is a CAML at T1 collected just before treatment. The PD-L1 signal is now weak. The signal of PD-L1 above background noise is less than a factor of 2 of the background noise, indicating potential poor response. FIG. 41 is a CAML at T3. The PD-L1 signal is now very weak. The signal of PD-L1 above background noise is less than a factor of 1 of the background noise; this is an indication of loss of drug target, such as PD-L1.

A fifth example is related to monitoring the success of surgery. Figure S5 in paper by Adams et al. (Circulating giant macrophages as a potential biomarker of solid tumors. *PNAS* 2014, 111(9):3514-3519) showed that surgery reduced the number of CAMLs. Continued presence of CAMLs in the blood of the patient could indicate that cancer might not be completely eradicated.

Capture of CAMLS and CTCs

Cells larger and/or less flexible than other cells present in a bodily fluid may be collected by filtering the bodily fluid. For example, targeted cells indicative of a condition, e.g., CAMLs and CTCs, may be collected by passing a bodily fluid through a filter having openings that are too small for the target cells to pass through, but large enough for other cells to pass through. Once collected, any number of analyses of the target cells may be performed. Such analyses may include, for example, identifying, counting, characterizing expressions of markers, obtaining molecular analysis, and/or culturing the collected cells.

CAMLs, pathologically-definable CTCs, and apoptotic CTCs are larger than red blood cells and most white blood cells. Using a precision microfilter that has precision pore size and pore distribution has been shown to provide high capture efficiency and low standard of deviation for these cells. CellSieve™ microfilters (Creatv MicroTech) are one example of precision microfilters. CellSieve™ microfilters are transparent and nonfluorescent making them ideal for microscope imaging analysis. Pore sizes of 7-8 microns eliminated all the red blood cells and 99.99% of the white blood cells. Methods to fabricate microfilters producing uniform pore size and distribution are described in WO 2011/139445, and PCT/US12/66390, both of which is incorporated herein by reference in their entireties. Microfilters made by a track etch method have randomly located pores that can overlap resulting in effectively large pores. They might lose some CAMLs and CTCs.

Besides microfiltration many other methods exist for capture of CTCs, and some can also be adopted to capture CAMLs. They generally break-down into the following categories:

Because CAMLs are large compared with majority of blood cells, many size based methods are suitable for capturing CAMLs. Microfilters with 7-8 micron pores are ideal for simultaneously capture of CAMLs and CTCs. If only CAMLs are of interest, not CTCs, then the pore size can be larger to approximately 15-20 microns. The larger pore sizes will eliminate most of the WBC contamination on the filter.

Immunocapture use ferrofluids, magnetic beads, microfluidic chips, etc, coated with antibody for selection of CAMLs, or elimination of other cells.

Red blood cell lysis can also be used for collecting CAMLs. The resultant sample volume requires plating on multiple glass slides.

White blood cell depletion.

FICOLL® (a hydrophilic polysaccharide).

Electrophoresis.

Dielectrophoresis.

Flow cytometry.

Microfluidic chips technologies that sort, select, group, trapping, concentrates large cells or eliminate small cells by size, utilization a variety of biological and physical principles are also suitable.

Filtration is the best method to identify WBC bond to a CTC. Because both the WBC and CTCs lose their markers and lose cytoplasm, immunocapture and flow cytometry are less suitable methods to isolate them.

In the relevant aspects and embodiments of the invention, CTCs and WBCs bond to CTCs may be detected alone or in conjunction with the detection of CAMLs. Such detection may be simultaneously or sequential detection, and can utilize the same or different means. For example, simultaneous detection using a microfilter having a pore size that selects for both cell types may be used. Suitable microfilters can have a variety of pore sizes and shapes. Microfilters having pores of about 7-8 microns in size are acceptable, and include round, rectangular and race track pore shapes. Microfilters having round pores of about 7-8 microns in size are especially optimal when polymeric microfilters are used. In a preferred aspect, the microfilter has precision pore geometry and uniform pore distribution.

CAML Isolation and Identification for Poor Economy

Methods for isolating CAMLs and/or CTCs from a biological sample and counting the isolated cells using a camera, such as a cell phone camera, are embodiments of the present invention. Methods that utilize cameras, such as those on cell phones, may be used in those circumstances where equipment and reagents required for detailed analysis of CAMLs and/or CTCs via marker staining and visualization are not available. The ability to count CAMLs and/or CTCs based on colorimetric staining may be sufficient for some applications. When there is a lack of resources in a community, cancer tends to be diagnosed in late stages which translates to limited treatment options and dim outcomes. A method to provide a low cost diagnostic based on the counts of CAMLs and/or CTCs in a sample can adopt one or more of the following concepts.

(i) Utilize low cost filters with pore size ~15-20 microns.
(ii) Filter the blood sample by manual draw or low cost pump.
(iii) Use colorimetric stain to visualize the CAMLs and/or CTCs.
(iv) Image cells using a cell phone camera with/without a portable small lens, or a variety of white light microscope with 10× or lower magnification.

The large pore size in the filters will reduce the WBC contamination. Manual draw will reduce the cost. Colorimetric stain is low cost. Cell phone cameras can visualize CAMLs due to the large size of the cells.

Embodiments of Inventions

As suggested above, the unique characteristics of the CAMLs and CTCs described herein make them well-suited for use in clinical methodology including methods of screening and diagnosis diseases such as cancer, monitoring treatment, monitoring of disease progression and recurrence.

The invention is thus directed, in a first embodiment, to methods of screening a subject for cancer, comprising detecting CAMLs in a biological sample from a subject. In particular aspects, when CAMLs are detected in the biological sample, the subject is identified as potentially having a carcinoma, sarcoma, neuroblastoma, melanoma or other solid tumor. In other aspects, when CAMLs are detected in the biological sample, the subject is identified as having a carcinoma, sarcoma, neuroblastoma, melanoma or other solid tumor. In certain aspects, the methods encompassed by this embodiment also include detecting circulating tumor cells (CTCs) and T-cells bound to tumor cells in the biological sample. In particular aspects of this first embodiment, the subject is a subject suspected of having cancer.

After CAMLs, CTCs or T-cells bound to tumor cells are found, it may be possible to identify the type of tumor by staining, and in some instances, re-staining these cells with markers associated with the type of tumor. The National Cancer Institute tumor marker FactSheet lists many cancer markers (see the NCI web site having the URL ending in "cancer.gov/cancertopics/factsheet/detection/tumor-markers" and "cancer.gov/about-cancer/diagnosis-staging/diagnosis/tumor-markers-fact-sheet#q5"). Cancer markers are not limited to this list. A few examples of markers listed below can be used to stain CAMLs and CTCs to provide initial indications of the cancer type:
  BRAF mutation V600E: Cancer types: Cutaneous melanoma and colorectal cancer
  CA15-3/CA27.29: Cancer type: Breast cancer
  CA19-9: Cancer types: Pancreatic cancer, gallbladder cancer, bile duct cancer, and gastric cancer
  CA-125: Cancer type: Ovarian cancer
  Carcinoembryonic antigen (CEA): Cancer types: Colorectal cancer and breast cancer
  Cytokeratin fragments 21-1: Lung cancer
  Estrogen receptor (ER)/progesterone receptor (PR): Cancer type: Breast cancer
  HE4: Cancer type: Ovarian cancer
  HER2/neu: Cancer types: Breast cancer, gastric cancer, and esophageal cancer
  KIT: Cancer types: Gastrointestinal stromal tumor and mucosal melanoma
  Prostate-specific antigen (PSA) and PSMA: Cancer type: Prostate cancer
  Thyroglobulin: Cancer type: Thyroid cancer
  5-Protein signature (Oval): Cancer type: ovarian cancer
The choice of markers is not limited to this list.

To identify one type of cancer, one marker may be sufficient for some types of cancer. To screen for more than one type of cancer in the same blood sample, such as prostate, colorectal and lung cancers for man, re-staining of the CAMLs and CTCs with cancer markers specific for those types of cancers is required after identifying the CAMLs and CTCs of interest. The following is an illustration of analyzing CAMLs and CTCs for cancer screening up to four types of epithelial cancers using microfiltration method:
  Collect blood.
  Isolate CTCs and CAMLs on the microfilter.
  Stain the cells by DAPI, CK 8, 18, 19, CD14/CD45, and one marker for one type of cancer.
  Image the cells using fluorescent microscopes and identify CAMLs and CTCs.
  Quench the fluorescent dyes in the CAML and CTCs.
  Re-stain the cells with DAPI and three additional markers of interest.
  Re-image the new markers in same CTCs and CAMLs previously imaged.
  Determine the type of cancer based on the markers.

CT scans for lung can show unusual findings as small as 4 mm in size. It is now a recommended screening method for lung cancer. To verify that an initial finding is lung cancer, tissue biopsy is needed. Tissue biopsy for lung is very challenging and it is associated with higher risk of causing undesirable effects. Presence of CAMLs with associated lung cancer markers such as cytokeratin fragments 21-1, and other markers can be used to provide a non-invasive step towards determine lung cancer.

For people carrying BRAC1 and BRAC2 mutations, they have a high probability of getting breast and/or ovarian cancers. A blood test for CAMLs including the markers of CA125, Oval for ovarian cancer, and CEA, CA15-3/CA27.29, ER, PR and HER2 for breast cancer can be performed.

To screen top four types of cancer for man, one possible set of choices for markers can be PSMA for prostate cancer, CEA for colorectal cancer, cytokeratin fragments 21-1 for lung cancer and PDX-1 for pancreatic cancer.

The procedure and markers can vary depending on the CAML and CTC isolation method, the microscope, cancer types of interest, etc. In summary, it is possible to screen for one specific cancer, a few cancers, or any solid tumors in the category of carcinomas, sarcomas, neuroblastomas and melanomas. The markers do not need to be limited to the ones describe here.

In a second embodiment, the invention is directed to methods for diagnosing cancer in a subject, comprising detecting CAMLs in a biological sample from a subject, wherein when CAMLs are detected in the biological sample, the subject is diagnosed with cancer. The identification of the specific type of cancer can be performed by standard methods, such as staining for cancer markers. The identification of the specific type of cancer can also be performed by staining for cancer markers and then re-staining the same cells for additional markers. In certain aspects, the methods encompassed by this embodiment also include detecting CTCs in the biological sample, wherein when CAMLs and CTCs are detected in the biological sample, the subject is diagnosed with cancer. In certain aspects, the methods encompassed by this embodiment also include detecting CTCs bound to a WBC and/or detecting an apoptotic CTC bound to a WBC in the biological sample, wherein when CTCs bound to a WBC and/or an apoptotic CTC bound to a WBC are detected in the biological sample, the subject is diagnosed with cancer.

In a third embodiment, the invention is directed to methods for detecting recurrence of cancer in a subject, comprising detecting CAMLs in a biological sample from a subject previously treated for cancer, wherein when CAMLs are detected in the biological sample, recurrence of cancer is detected. The identification of the specific type of cancer can be performed by standard methods, such as staining for cancer markers. The identification of the specific type of cancer can also be performed by staining for cancer markers and then re-staining the same cells for additional markers. In certain aspects, the methods encompassed by this embodiment also include detecting CTCs and/or WBCs bound to CTCs in the biological sample, wherein when CAMLs, CTCs and WBCs bound to CTCs are detected in the biological sample, recurrence of cancer is detected. To identify the recurrence of the specific cancer, the stains should specifically include markers associated with the cancer in remission.

In a fourth embodiment, the invention is directed to methods for confirming a diagnosis of cancer in a subject, comprising detecting CAMLs in a biological sample from a subject diagnosed with cancer, wherein when CAMLs are detected in the biological sample, a diagnosis of cancer is confirmed in the subject. The invasive confirmation by tissue biopsy may be avoided by most patients; the tissue biopsy would be necessary only when CAMLs are present. In certain aspects, the methods encompassed by this embodiment also include detecting CTCs and/or WBCs bound to CTCs in the biological sample, wherein when one or more of CAMLs, CTCs and WBCs bound to CTCs are detected in the biological sample, a diagnosis of cancer is confirmed in the subject. In particular aspects, the initial cancer diagnosis is via mammography, PSA test, presence of CA125, CT, MRI or PET imaging. In a particular aspect, the subject is suspected of having cancer. The identification of the specific type of cancer can be performed by standard methods, such as staining for cancer markers. The identification of the specific type of cancer can also be performed by staining for cancer markers and then re-staining the same cells for additional markers.

In a fifth embodiment, the invention is directed to methods for determining cancer stage in a subject, comprising characterizing CAMLs in a biological sample from a subject having a cancer, wherein selected characteristics of the CAMLs indicate cancer stage in the subject. The identification of the specific type of cancer can be performed by standard methods, such as staining for cancer markers. The identification of the specific type of cancer can also be performed by staining for cancer markers and then re-staining the same cells for additional markers. In certain aspects, the methods encompassed by this embodiment also include characterizing CTCs in the biological sample, wherein selected characteristics of the CAMLs and CTCs indicate cancer stage in the subject. In certain aspects, the CAMLs and/or CTCs are collected from the biological sample prior to characterization. The number of CAMLs in stage III and IV cancer are typically 5 or more in a sample of peripheral blood in a volume of 7.5 ml. The percentage of CAMLs larger than 40 microns in size by diameter is about 70% for Stage III and about 80% for Stage IV patients.

In a sixth embodiment, the invention is directed to methods for monitoring efficacy of a cancer treatment, comprising (a) assaying one or more selected characteristics of CAMLs in a biological sample from a subject undergoing cancer treatment, and (b) comparing assay values for the one or more selected characteristics determined in (a) to assay values for the same characteristics assayed in a similar biological sample from the same subject at one or more time points before, during or after completion of treatment, wherein a change in one or more assay values indicates efficacy of the cancer treatment in the subject. In certain aspects, the methods encompassed by this embodiment also include (a) assaying one or more selected characteristics of CTCs in the biological sample, and (b) comparing assay values for the one or more selected characteristics determined in (a) to assay values for the same characteristics assayed in a similar biological sample from the same subject at one or more time points before, during or after completion of treatment. In certain aspects, the CAMLs and/or CTCs are collected from the biological sample prior to characterization.

In certain aspects, the selected characteristics of the CAMLs are one or more of: (i) change of the number of CAMLs from the same subject at different time points after treatments; (ii) change in average size of CAMLs at the different time points; (iii) change in intensity of markers in the CAMLs at the different time points; and (iv) change of location of markers from nucleus to cytoplasm or vice versa in the CAMLs.

In certain aspects, the selected characteristics of the CTCs are one or more of: (i) change of the number of CTCs in the biological samples at different time points after treatment; (ii) change in intensity of markers in the CTCs at the different time points; (iii) change of location of markers from nucleus to cytoplasm or vice versa; (iv) change in number of WBCs bound to CTCs in the biological sample; and (v) change in number of WBCs bound to CTCs in the biological samples at different time points after treatments.

The skilled artisan will understand that a change in the number of CAMLs and/or CTCs and/or WBCs bound to CTCs will be an indication of treatment efficacy, where the change may be an increase or a decrease in the number of CAMLs and/or CTCs and/or WBCs bound to CTCs. The information gathered on CAMLs, CTCs and CTC bound to WBC can be used independent of each other. The information gathered on CAMLs, CTCs and CTC bound to WBC can also be used together.

The skilled artisan will understand that a change in the size of CAMLs and/or CTCs can be an indication of treatment efficacy, where the change in the size may be an increase or a decrease in size of CAMLs and/or CTCs and/or WBCs bound to CTCs. The information gathered on CAMLs and CTCs can be used independently or together.

The capability of tracking CAMLs provides a novel opportunity to routinely monitor necrosis and chemotherapy or radiation therapy response. If the chemotherapy is not working, the CAMLs number will not increase. This can be used in parallel with CTC detection. If the treatment is working, the number of pathologically-definable CTCs will decrease and number of apoptotic CTCs will increase. However, CTCs cannot always be detected. If CTCs are detected at the same time as CAMLs, the sensitivity and specificity can be improved. For many cancers there are large array of chemotherapy agents. If the patient is not responding to one type of chemotherapy, the patient can quickly switch to another.

The invention is also directed to methods for isolating CAMLs and/or CTCs from a biological sample and counting the isolated cells using a camera, such as a cell phone camera, or white light microscope, or a camera attached to a white light microscope. Thus, and in a seventh embodiment, the present invention is directed to methods for detecting CAMLs and/or CTCs in a biological sample, comprising obtaining a biological sample from a subject, and detecting CAMLs and/or CTCs in the sample, wherein the detecting is via a camera, a white light microscope or a camera attached to a white light microscope. In certain aspects, the camera is a cell phone camera. In certain aspects, the white light microscope has a magnification power of 10× or less. In other aspects, the cells are collected from the biological sample via low cost filters and/or the biological sample is the obtained by manual draw from the subject or low cost pump. In further aspects, colorimetric staining is used to visualize the CAMLs and/or CTCs.

In an eighth embodiment, the invention is directed to a companion diagnostic method for screening selected drug target markers in CAMLs and/or CTCs comprising collecting CAMLs and/or CTCs from a biological sample from a subject and determining whether the CAMLs and/or CTCs express or possess a selected drug target marker. In certain aspects, the drug target marker is cell surface marker, and the determining may be, for example, via staining for the marker. As an example, PD-L1 can be used as a cell surface marker for immunotherapeutics. In other aspects, the drug target marker is a polynucleotide. In further aspects, the drug target marker is a genetic mutation, amplification or translocation and the determining may be, for example, via FISH.

In a ninth embodiment, the invention is directed to methods for diagnosing a viral infection in a subject, comprising collecting CAMLs from a biological sample obtained from a subject and screening the collected CAMLs for a virus. In certain aspects, the screening is via staining CAMLs for a viral marker. In further aspects, the screening is via molecular analysis of DNA or RNA from the CAML.

Traditional methods of detection of viruses are based on presence of antibodies or viral particles in the blood. Because CAMLs engulf viral debris, cells infected by virus, and cell debris that contains virus, the use of CAMLs in the manner can provide a useful tool in detecting and diagnosing viral infections. The source of the viral infection that can be diagnosed using these methods is not limited and includes, for example Human Immunodeficiency Virus (HIV), Hepatitis B Virus (HBV), Epstein-Barr Virus (EBV), among others.

Some viral infections, such as HIV and HBV, can lead to cancer. CAMLs found in the blood of subjects having such infections can be caused either by the viral infection or by cancer itself. Staining for cancer markers or for viral markers can be used to provide diagnostic information. This may be a useful method for early detection of virus-caused cancers.

In the relevant aspects and embodiments of the invention, the therapies comprise vaccination, chemotherapy, radiation therapy, immunotherapy, targeted therapy, and combinations thereof.

In the relevant aspects and embodiments of the invention, the biological sample may be any suspected of containing CTCs, WBCs bound to CTCs, and/or CAMLs. In certain aspects, the biological sample is one or more selected from the group consisting of peripheral blood, blood, lymph nodes, bone marrow, cerebral spinal fluid, tissue, and urine. The sample may be a fresh sample or a cryo-preserved sample that is thawed. In a preferred aspect, the biological sample is peripheral blood. In other aspects, the blood is antecubital-vein blood, inferior-vena-cava blood or jugular-vein blood.

Circulating monocytes have the ability to enter any tissue compartment of the body, including lymph nodes, bone marrow, most organs, and even cross the blood brain barrier. The detection of CAMLs is therefore not limited to blood, and the cells can also be found in lymph nodes, bone marrow, cerebral spinal fluid, most organs, and urine.

In the relevant aspects and embodiments of the invention, the cancer is one or more of a solid tumor, Stage I cancer, Stage II cancer, Stage III cancer, Stage IV cancer, carcinoma, sarcoma, neuroblastoma, melanoma, epithelial cell cancer, breast cancer, prostate cancer, lung cancer, pancreatic cancer, colorectal cancer, and other solid tumor cancers. The skilled artisan will appreciate that the methods of the invention are not limited to particular forms or types of cancer and that they may be practiced in association with a wide variety of cancers.

Since CAMLs can be found in stage I and II of cancer, CAMLs can be used as screening for early detection of carcinomas, sarcomas, neuroblastomas and melanomas. Carcinomas are cancer of epithelial origin especially for high risk patients for breast, prostate, lung, pancreatic, colorectal and other cancers. Specificity of the type of cancer can be determined by re-staining for various cancer site specific markers on the same cells captured on the microfilter. Some examples are (i) use antibody against PSMA to specifically identifying prostate cancer, (ii) use antibody against PDX-1 to specifically identifying lung cancer, (iii) antibody against CA125 for ovarian cancer, and (iv) clorotoxin to identify glioma.

Similarly CAMLs can be used to determine early recurrence of cancer when the cancer was under remission. Currently CT, MM and PET imaging are used to monitor the patient's tumor, requiring the tumor to change in size substantially to notice the difference. Patients can therefore lose valuable time in beginning treatment when only subtle size changes occur. CAMLs, alone or in combination with CTCs, can provide early detection of return of cancer. Non-invasive blood test of CAMLs and CTCs is much lower in cost than CT, MM and PET imaging.

The CAMLs can also potentially be used to determine cancer subtyping or gene mutations, translocations or amplification. There are a number of cancerous nuclei in each CAML. Thus, molecular analysis of the nucleus for genetic mutation, genetic defects, and gene translocations can provide information to determine treatments. There are drugs that specifically target certain gene mutations, translocation or amplifications. CAMLs can be used along or in parallel with CTCs for molecular analysis.

In the relevant aspects and embodiments of the invention, the volume of the biological sample will vary based on the source and/or identity of the sample. However, in the case of peripheral blood, the volume of blood may range from about 0.5 ml to about 50 ml, about 1 ml to about 40 ml, about 2 ml to about 30 ml, about 3 ml to about 25 ml, about 4 ml to about 20 ml, about 5 ml to about 15 ml, about 6 ml to about 10 ml, or about 7 ml to about 8 ml. A suitable volume also includes about 1, 1.5, 2, 2.5, 3, 3.5, 4, 4.5, 5, 5.5, 6, 6.5, 7, 7.5, 8, 8.5, 9, 9.5 or 10 ml. Blood volume typically used for detection of CTCs is 7.5 mL. Larger volumes of blood will provide more sensitivity and consistency, but smaller volumes such as 3.5 mL may be sufficient. For many CTC detection methods, larger volumes of blood are not practical for a variety of reasons. However, microfiltration of blood to capture CTCs and/or CAMLs allows more flexibility to increase the sample size. Blood volumes of 50 mL have been shown to be successfully screened using CellSieve™ microfilters with 160,000 pores. The suitable volume of blood to capture CAMLs would be 7.5 ml.

In the relevant aspects and embodiments of the invention, the anti-cancer therapeutic may be one or more of chemotherapy, radiation therapy, immunotherapy, vaccine therapy, targeted therapy, and/or a combination of therapies.

In the relevant aspects and embodiments of the invention, CAMLs are detected and/or collected using one or more means selected from the group consisting of size exclusion methodology, immunocapture, red blood cell lysis, white blood cell depletion, FICOLL® (a hydrophilic polysaccharide), electrophoresis, dielectrophoresis, flow cytometry and microfluidic chip, or a combination thereof. In a particular aspect, the size exclusion methodology comprises use of a microfilter. Suitable microfilters can have a variety of pore sizes and shapes. When CAMLs alone are being detected and/or collected, the pore sizes can range from about 15 microns to about 20 microns. When both CAMLs and CTCs are being detected and/or collected, the pore sizes can range from about 5 microns to about 10 microns, preferably 7-8 microns. The larger pore sizes will eliminate most of the WBC contamination on the filter. The pores may have a round, race-track shaped, oval, square and rectangular pore shape. In a preferred aspect, the microfilter has precision pore geometry and uniform pore distribution. In a particular aspect, CAMLs are detected and/or collected using a microfluidic chip based on physical size-based sorting, hydrodynamic size-based sorting, grouping, trapping, immunocapture, concentrating large cells, or eliminating small cells based on size. In a particular aspect, the CAMLs are detected and/or collected using a CellSieve™ low-pressure microfiltration assay.

The results reported herein support the idea that CAMLs provide a robust indicator of cancer presence. The sensitivity and specificity of the utility of CAMLs can be further improved in combination with simultaneous detection of CTCs and CTCs bond to WBCs. Cancer screening is a strategy used in a population to identify an unrecognized disease in individuals without signs or symptoms, with pre-symptomatic or unrecognized symptomatic disease. As such, screening tests are somewhat unique in that they are performed on persons apparently in good health. A screening test is not a diagnostic test. Diagnostic testing is a procedure performed to confirm, or determine the presence of disease in an individual suspected of having the disease. CAMLs can be used as a cancer diagnostic to provide additional non-invasive diagnostics to confirm other screening techniques, such as mammography, PSA test, presence of CA125, CT, MRI or PET imaging.

We claim:

1. A method for confirming a diagnosis of cancer in a subject diagnosed with cancer, comprising detecting Cancer Associated Macrophage-Like cells (CAMLs) in a biological sample from the subject diagnosed with cancer, wherein said detecting comprises:
   (a) isolating intact cells of between about 20 microns to about 300 microns from the biological sample obtained from the subject using a microfilter having pores of about 15-20 microns in size, wherein the biological sample is one or more of peripheral blood, blood, lymph nodes, bone marrow, cerebral spinal fluid, tissue, or urine; and
   (b) selecting cells isolated in (a) having the following characteristics:
      (i) multiple individual nuclei and/or large fused nucleoli having a size of about 14-64 pm diameter;
      (ii) morphological shape selected from the group consisting of spindle, tadpole, round, oblong, and amorphous; and
      (iii) expression of one or more of the following markers: cytokeratin (CK) 8, CK18, CK19, vimentin, Cluster of differentiation (CD) 45, CD11c, CD 14, CD 146, CD202b, or CD31, wherein antibodies are used to select cells expressing the one or more markers, thereby detecting CAMLs in a biological sample from a subject,
   wherein when CAMLs are detected in the biological sample, the diagnosis of cancer is confirmed in the subject.

2. The method of claim 1, wherein the initial cancer diagnosis was via mammography, prostate-specific antigen (PSA) test, the presence of Cancer Antigen 125 (CA125), computed tomography (CT), magnetic resonance imaging (MRI) or positron-emission tomography (PET) imaging.

3. The method of claim 1, further comprising administering an anti-cancer therapeutic to the subject when diagnosis of cancer is confirmed in the subject.

4. The method of claim 1, wherein the microfilter has precision pore geometry and uniform pore distribution.

5. The method of claim 1, wherein CAMLs are detected using a microfiltration assay.

6. The method of claim 1, wherein the cancer is a solid tumor.

7. The method of claim 1, wherein the cancer is Stage I, Stage II, Stage III, or Stage IV cancer.

8. The method of claim 1, further comprising visualizing CAMLs by immuno-fluorescent staining.

9. The method of claim 1, further comprising visualizing CAMLs by colorimetric staining.

10. The method of claim 1, wherein molecular analysis of CAMLs is performed after diagnosis of cancer.

11. The method of claim 1, wherein the CAML size and number supports cancer staging.

12. The method of claim 1, further comprising detecting circulating tumor cells (CTCs) and/or white blood cells (WBCs) bound to CTCs in the biological sample, wherein CTCs and/or WBCs bound to CTCs are detected using a microfilter having a pore size of about 5-10 microns, and wherein when CTCs and/or WBCs bound to CTCs are detected in the biological sample, the diagnosis of cancer is further confirmed in the subject.

13. The method of claim 12, wherein the microfilter for use in detecting CTCs and/or WBCs bound to CTCs has a pore size of about 7-8 microns.

14. The method of claim 1, further comprising determining the identity of the cancer via staining said CAMLs for selected cancer markers.

15. The method of claim 14, wherein the staining further comprises quenching and re-staining the same cells for additional cancer markers.

* * * * *